(12) United States Patent
Cho et al.

(10) Patent No.: US 6,683,184 B2
(45) Date of Patent: Jan. 27, 2004

(54) PIPERAZINE DERIVATIVES AND PROCESS FOR THE PREPARATION THEREOF

(75) Inventors: Eui-Hwan Cho, Seoul (KR); Sun-Gan Chung, Kyungki-do (KR); Sun-Hwan Lee, Kyungki-do (KR); Ho-Seok Kwon, Kyungki-do (KR); Dong-Wook Kang, Kyungki-do (KR); Jeong-Ho Joo, Kyungki-do (KR); Young-Hee Lee, Kyungki-do (KR)

(73) Assignee: Samjin Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 10/105,936

(22) Filed: Mar. 26, 2002

(65) Prior Publication Data

US 2003/0092910 A1 May 15, 2003

Related U.S. Application Data

(63) Continuation of application No. 09/674,686, filed as application No. PCT/KR00/00164 on Mar. 3, 2000, now abandoned.

(30) Foreign Application Priority Data

| Mar. 3, 1999 | (KR) | 1999-6890 |
| Mar. 5, 1999 | (KR) | 1999-7266 |
| Mar. 11, 1999 | (KR) | 1999-8088 |
| Mar. 31, 1999 | (KR) | 1999-11254 |

(51) Int. Cl.$^7$ .................. C07D 401/12; C07D 403/12
(52) U.S. Cl. .................. 544/354; 544/356; 544/360; 544/363; 544/390; 544/357; 544/392
(58) Field of Search .................. 544/354, 356, 544/360, 363, 392, 390, 357

(56) References Cited

U.S. PATENT DOCUMENTS 6,028,195 A  *  2/2000  Cho et al. .................. 544/360

* cited by examiner

Primary Examiner—Emily Bernhardt
(74) Attorney, Agent, or Firm—Birch, Stewart, Kolasch & Birch, LLP

(57) ABSTRACT

The present invention relates to a novel compound of formula (I) and its pharmaceutically acceptable acid addition salt, and process for the preparation thereof, which have strong antitumor activities and very low toxicity:

(I)

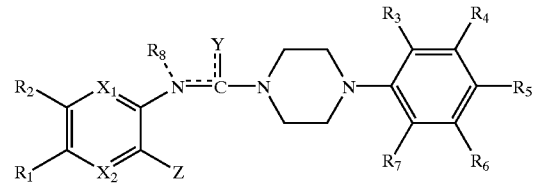

wherein $R_1$ and $R_2$ are independently hydrogen, $C_1$–$C_4$ alkyl, $C_1$–$C_4$ alkylcarboxyl, $C_1$–$C_4$ alkylcarbonyl, $C_1$–$C_4$ alkoxy, $C_1$–$C_4$ hydroxyalkyl, $C_1$–$C_4$ aminoalkyl or $C_1$–$C_4$ hydroxyiminoalkyl, or $R_1$ and $R_2$ are fused to form $C_3$–$C_4$ unsaturated ring;

$R_3$, $R_4$, $R_5$, $R_6$ and $R_7$ are independently hydrogen, halogen, hydroxy, nitro, amino, $C_1$–$C_4$ alkyl, $C_1$–$C_4$ alkylcarboxyl, $C_1$–$C_4$ alkylcarbonyl, $C_1$–$C_4$ alkoxy, $C_1$–$C_4$ thioalkoxy; $R_8$ is $C_1$–$C_4$ alkyl;

Y is oxygen, sulphur, amino, subsitituted amino or $C_1$–$C_4$ thioalkyl; Z is $C_1$–$C_4$ alkoxy, $C_1$–$C_4$ alkyl, $C_1$–$C_4$ alkylamino or $C_1$–$C_4$ thioalkoxy;

$X_1$ and $X_2$ are independently CH or nitrogen; and

—N═C— and —C═Y— may form a single bond or a double bond provided that if —N═C— forms a single bond, —C═Y— forms a double bond, and if —C═Y— forms a single bond, —N═C— forms a double bond and $R_8$ is nonexistent.

3 Claims, No Drawings

PIPERAZINE DERIVATIVES AND PROCESS FOR THE PREPARATION THEREOF

This application is a continuation of U.S. patent application Ser. No. 09/674,686, filed May 30, 2001, now abandoned which is a 371 application of PCT application PCT/KR00/00164, filed Mar. 3, 2000, which claims priority based on Korean patent application Nos. 1999-6890, filed Mar. 3, 1999, and 1999-8088, filed Mar. 11, 1999.

The present invention relates to a new piperazine derivative of the general formula (I) or its pharmaceutically acceptable acid addition salt, and process for the preparation thereof.

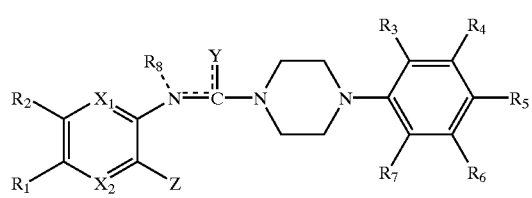

(I)

wherein $R_1$ and $R_2$ are independently hydrogen, $C_1$–$C_4$ alkyl, $C_1$–$C_4$ alkylcarboxyl, $C_1$–$C_4$ alkylcarbonyl, $C_1$–$C_4$ alkoxy, $C_1$–$C_4$ hydroxyalkyl, $C_1$–$C_4$ aminoalkyl or $C_1$–$C_4$ hydroxyiminoalkyl, or $R_1$ and $R_2$ are fused to form $C_3$–$C_4$ unsaturated ring;

$R_3$, $R_4$, $R_5$, $R_6$, and $R_7$ are independently hydrogen, halogen, hydroxy, nitro, amino, $C_1$–$C_4$ alkyl, $C_1$–$C_4$ alkylcarboxyl, $C_1$–$C_4$ alkylcarbonyl, $C_1$–$C_4$ alkoxy or $C_1$–$C_4$ thioalkoxy; $R_8$ is $C_1$–$C_4$ alkyl;

Y is oxygen, sulphur, amino, subsitituted amino or $C_1$–$C_4$ thioalkyl;

Z is $C_1$–$C_4$ alkoxy, $C_1$–$C_4$ alkyl, $C_1$–$C_4$ alkylamino or $C_1$–$C_4$ thioalkoxy;

$X_1$ and $X_2$ are independently CH or nitrogen; and

—N═C— and —C═Y— may form a single bond or a double bond provided that if —N═C— forms a single bond, —C═Y— forms a double bond, and if —C═Y— forms a single bond, —N═C— forms a double bond and $R_8$ is nonexistent.

In the above definitions, $C_1$–$C_4$ alkyl means methyl, ethyl, propyl, isopropyl, n-butyl, isobutyl or tert-butyl.

$C_1$–$C_4$ alkylcarboxyl means carboxyl esterified with a lower alkyl such as methylcarboxyl and ethylcarboxyl.

$C_1$–$C_4$ alkylcarbonyl means carbonyl ketonized with a lower alkyl such as methylcarbonyl and ethylcarbonyl.

$C_1$–$C_4$ alkoxy means methoxy, ethoxy, propoxy, isopropoxy, butoxy, isobutoxy or tert-butoxy.

$C_1$–$C_4$ thioalkoxy means methylthio, ethylthio, propylthio, isopropylthio, butylthio, isobutylthio or tert-butylthio.

$C_1$–$C_4$ aminoalkyl means aminomethyl, aminoethyl, aminopropyl, aminobutyl or the like.

$C_1$–$C_4$ kydroxyalkyl means hydroxymethyl, hydroxyethyl, hydroxypropyl, hydroxybutyl or the like.

$C_1$–$C_4$ hydroxyiminoalkyl means $C_1$–$C_4$ alkyl substituted with hydroxyimino such as hydroxyiminoethyl.

Substituted amino means hydroxyamino, $C_1$–$C_4$ alkylamino, $C_1$–$C_4$ alkoxyamino or the like.

The present inventors had studied for a long time to find compounds having intensive antitumor activity. As a result, now we have finally found out the facts that the present compounds of the general formula (I) and acid addition salts thereof have not only prominent antitumor activities but very low toxicities.

Accordingly, the one object of the present invention is to provide the novel compounds of the general formula (I) and acid addition salts thereof having not only prominent antitumor activities but very low toxicities.

The other object of the present invention is to provide a process for the preparation of the compounds of general formula (I) and acid addition salts thereof.

The compounds of the present invention can be mixed with pharmaceutically acceptable vehicles by a known method to give pharmaceutical compositions and thus the pharmaceutical compositions can be used to prevent or treat with various kinds of tumors of human beings or mammals.

Therefore, another object of the present invention is to provide pharmaceutical compositions containing the compound of the general formula (I) or an acid addition salt thereof as an active ingredient.

Acids which can be reacted with the compounds of the general formula (I) to form acid addition salts are pharmaceutically acceptable inorganic or organic acids; for example, inorganic acids such as hydrochloric acid, bromic acid, sulfuric acid, phosphoric acid, nitric acid; organic acids such as formic acid, acetic acid, propionic acid, succinic acid, citric acid, maleic acid, malonic acid, glycolic acid, lactic acid; amino acids such as glycine, alanine, valine, leucine, isoleucine, serine, cysteine, cystine, asparaginic acid, glutamic acid, lysine, arginine, tyrosine, proline; sulfonic acids such as methane sulfonic acid, ethane sulfonic acid, benzene sulfonic acid, toluene sulfonic acid; or the like.

Vehicles which can be used in the preparation of pharmaceutical compositions containing the compound of the general formula (I) as the active ingredient may include a sweetening agent, binding agent, dissolving agent, aids for dissolution, wetting agent, emulsifying agent, isotonic agent, adsorbent, degrading agent, antioxident, antiseptics, lubricating agent, filler, perfume or the like; such as lactose, dextrose, sucrose, mannitol, sorbitol, cellulose, glycine, silica, talc, stearic acid, stearin, magnesium stearate, calcium stearate, magnesium aluminum silicate, starch, gelatine, tragacanth gum, glycine, silica, alginic acid, sodium alginate, methyl cellulose, sodium carboxy methyl cellulose, agar, water, ethanol, polyethylenglycol, polyvinyl pyrrolidone, sodium chloride, potassium chloride, orange essence, strawberry essence, vanilla aroma or the like.

Daily dosage of the compound of the general formula (I) may be varied depending on age, sex of a patient, degree of disease, etc. and generally 1.0 mg to 5,000 mg per day may be administered one to several times.

The compounds of the general formula (I) according to the present invention wherein —N═C— forms a single bond and —C═Y— forms a double bond, may be prepared by the following scheme I.

Scheme I

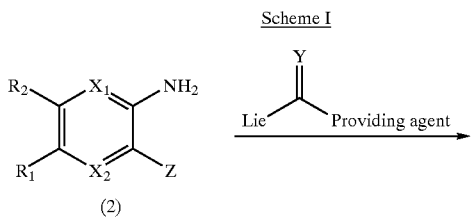

(2)

3

-continued

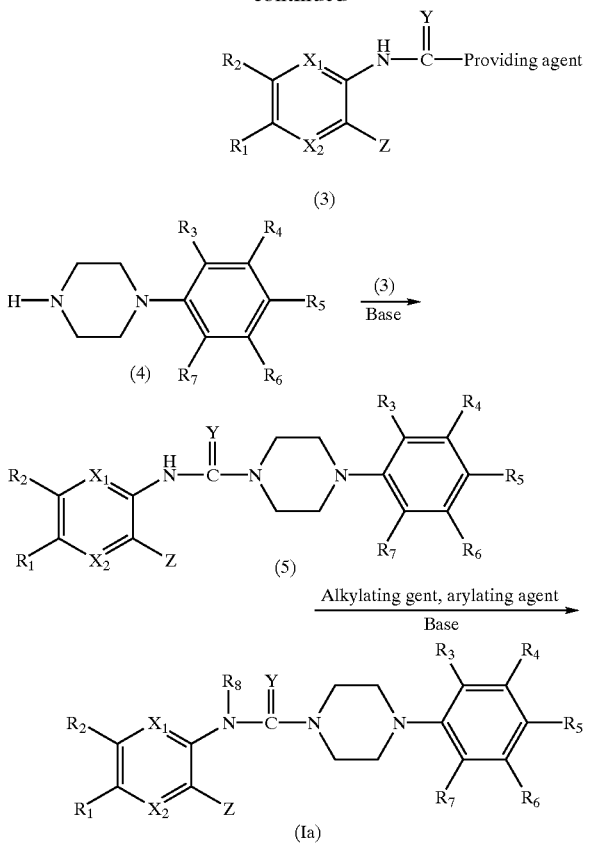

wherein $R_1$, $R_2$, $R_3$, $R_4$, $R_5$, $R_6$, $R_7$, $R_8$, $X_1$, $X_2$, Y and Z are as defined above, and Lie is a conventional leaving group such as halogen, sulfonyl or the like.

The above process comprises reacting a compound of the general formula (2) with a —C(=Y)— group-providing agent in an organic solvent to obtain a compound of the general formula (3) and successively reacting the compound of the formula (3) with a compound of the general formula (4) to give the compound of the general formula (5). Then, the compound of the formula (5) may be reacted with an alkylating agent or an arylating agent in the presence of a base to give a compound of the general formula (Ia).

The —C(=Y)— group-providing agent used in the above reaction may include 1,1-carbonyldiimidazole, 1,1-carbonylthiodiimidazole, phosgene, thiophosgene, carbonyldiphenoxide and phenylchloroformate, and it may be used in an amount of 1–1.5 equivalent, preferably 1–1.1 equivalent to the starting compound.

organic solvent such as, for example, tetrahydrofuran, dichloromethane, acetonitrile, chloroform and dimethylformamide.

And also the reaction is preferably carried out in the presence of a coupling agent such as a conventional inorganic or an organic base. Such conventional inorganic or organic bases used in the reaction may include sodium hydride, potassium hydride, sodium hydroxide, potassium hydroxide, sodium carbonate, potassium carbonate, cesium carbonate, sodium bicarbonate, potassium bicarbonate, triethylamine, pyridine and DBU.

The reaction may be carried out at a temperature between 3° C. and boiling point of the solvent used, preferably at 50° C.–100° C. and for 5–48 hours, preferably for 10–24 hours.

The reaction of the compound (3) with the compound (4) to give the compound (5) may be carried out in the presence of a conventional organic solvent at the temperature of 50–100° C. for 5–48 hours. The compound (4) may be used by 1–1.5 equivalent.

And also the reaction is preferably carried out in the presence of a conventional inorganic or organic base, such as sodium hydride, potassium hydride, sodium hydroxide, potassium hydroxide, sodium carbonate, potassium carbonate, cesium carbonate, sodium bicarbonate, potassium bicarbonate, triethylamine, pyridine, DBU or the like.

Then, the compound of the formula (5) may be reacted with an alkylating agent or an arylating agent in the presence of a conventional organic or inorganic base to give a compound of the general formula (Ia).

The alkylating agent and arylating agent used in the above step may include $C_1$–$C_8$ alkylhalide, $C_1$–$C_8$ alkylsulfonate, substituted or unsubstituted $C_3$–$C_8$ cycloalkyl halide, arylhalide, and substituted or unsubstituted $C_3$–$C_8$ cycloalkyl sulfonate.

$C_1$–$C_8$ alkyl halide means methyl chloride, methyl bromide, methyl iodide, ethyl chloride, ethyl bromide, ethyl iodide, propyl chloride, propyl bromide, propyl iodide, butyl chloride, butyl bromide, butyl iodide, pentyl chloride, pentyl bromide, pentyl iodide, bromo ehtylacetate or the like.

$C_1$–$C_8$ alkylsulfonate means methyl sulfonate, ethyl sulfonate, propyl sulfonate, butyl sulfonate, pentyl sulfonate or the like.

Substituted or unsubstituted $C_3$–$C_8$ cycloalkyl halides mean cyclopropyl chloride, cyclopropyl bromide, cyclopropyl iodide, cyclobutyl chloride, cyclobutyl bromide, cyclobutyl iodide, cyclopentyl chloride, cyclopentyl bromide, cyclopentyl iodide, cyclohexyl chloride, cyclohexyl bromide, cyclohexyl iodide, cyclopropyl methyl chloride, cyclopropyl methyl bromide, cyclopropyl methyl iodide, cyclobutyl methyl chloride, cyclobutyl methyl bromide, cyclobutyl methyl iodide, cyclopentyl methyl chloride, cyclopentyl methyl bromide, cyclopentyl methyl iodide, cyclohexyl methyl chloride, cyclohexyl methyl bromide, cyclohexyl methyl iodide, or the like.

Aryl halides may include benzyl chloride, benzyl bromide, benzyl iodide, benzoyl chloride, benzoyl bromide, benzoyl iodide, toluyl chloride, toluyl bromide and toluyl iodide.

Substituted or unsubstituted $C_3$–$C_8$ cycloalkyl sulfonate may include cyclopropyl sulfonate, cyclobutyl sulfonate, cyclopentyl sulfonate, cyclohexyl sulfonate, cyclopropyl methyl sulfonate, cyclobutyl methyl sulfonate, cyclopentyl methyl sulfonate and cyclohexyl methyl sulfonate.

Aryl sulfonate may include benzyl sulfonate, benzoyl sulfonate, toluyl sulfonate, or the like.

The reaction may be carried out in a conventional organic solvent as such as, for example, tetrahydrofuran, dichloromethane, chloroform, dimethyl sulfoxide, acetonitrile and dimethylformamide.

The conventional inorganic or organic base used in above step may include sodium hydride, potassium hydride, sodium hydroxide, potassium hydroxide, sodium carbonate, potassium carbonate, cesium carbonate, sodium bicarbonate, potassium bicarbonate, triethylamine, pyridine and DBU.

In the above reaction process, if any acid material is formed, a basic material may be added as a scavenger in order to eliminate the acid material from the reaction phase. Such basic material may be alkali metal hydroxide, alkali earth metal hydroxide, alkali metal oxide, alkali earth metal oxide, alkali metal carbonate, alkali earth metal carbonate, alkali metal hydrogen carbonate, alkali earth metal hydrogen carbonate such as for example, sodium hydroxide, potassium hydroxide, calcium hydroxide, magnesium hydroxide, magnesium oxide, calcium oxide, potassium carbonate, sodium carbonate, calcium carbonate, magnesium carbonate, magnesium bicarbonate, sodium bicarbonate, calcium bicarbonate or the like, and organic amines.

The compounds of the general formula (2) and the formula (4) are known compounds, or may be prepared by a known method described in, for example, Farmaco(pavia) Ed, Sci., 18(8), 557–65(1963) or by a similar method thereto.

A compound of the general formula (I) wherein —C=Y— forms a single bond and —N=C— forms a double bond may be prepared by the following scheme II

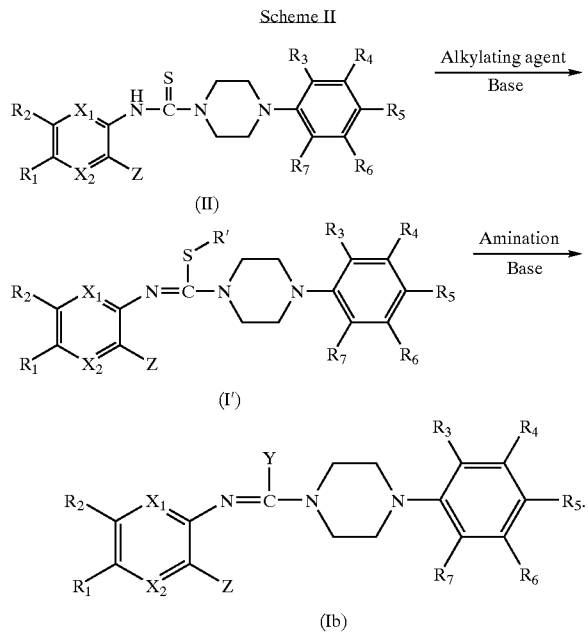

wherein $R_1$, $R_2$, $R_3$, $R_4$, $R_5$, $R_6$, $R_7$, $X_1$, $X_2$, Y and Z are as defined above, and R' is lower alkyl such as methyl and ethyl.

A compound of the general formula (II), which may be prepared by a known method, is reacted with an alkylating agent in the presence of a base to give a compound of the general formula (I'). Then, the compound of the formula (I') is reacted with a substituted or unsubstitued amine in the presence of a base to give a compound of the general formula (Ib).

The reaction may be carried out at a temperature between 3° C. and boiling point of the solvent used, preferably at 50° C.–100° C. for 5–48 hours, preferably for 10–24 hours.

The alkylating agent may be used in an amount of 1–1.5 equivalent to the compound (II). The alkylating agent may include $C_1$–$C_8$ alkyl halide, $C_1$–$C_8$ alkylsulfonate, substituted or unsubstituted $C_3$–$C_8$ cycloalkyl halide, aryl halide and substituted or unsubstituted $C_3$–$C_8$ cycloalkyl sulfonate.

The reaction may be carried out in a conventional organic solvent as described above.

The conventional inorganic or organic base as described above may be used in the above process.

The compound of the formula (I') is reacted with a substituted or unsubstitued amine in the presence of a conventional base to give a compound of the general formula (Ib).

The reaction also may be preferably carried out in a conventional organic solvent as described above.

The conventional inorganic or organic base described above may be used in the above reaction step.

In the above reactions, if any acid material is formed, any basic material may be preferably added as a scavenger in order to eliminate the acid material from the reaction phase. Such basic material may be the organic or inorganic bases as described in the scheme I above.

The compound of the general formula (II) is a known compound, or may be prepared by a known method described in, for example, U.S. Pat. No. 5,780,472, PCT/KR97/00128 or by a similar method thereto.

Hereinafter the present invention will be described in more details with reference to following examples but it is not intended to limit the scope of the invention thereinto.

Compounds of the general formula (Ia) were prepared in following examples according to the above-mentioned process.

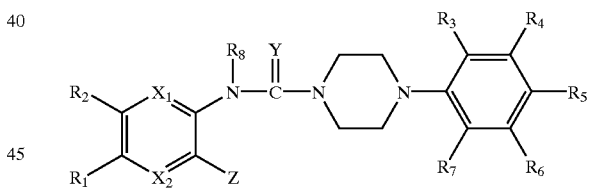

wherein $R_1$, $R_2$, $R_3$, $R_4$, $R_5$, $R_6$, $R_7$, $R_8$, $X_1$, $X_2$, Y and Z are as defined above.

| Ex | $R_1$ | $R_2$ | $R_3$ | $R_4$ | $R_5$ | $R_6$ | $R_7$ | $R_8$ | $X_1$ | $X_2$ | Y | Z |
|----|-------|-------|-------|-------|-------|-------|-------|-------|-------|-------|---|---|
| 1  | $CH_3$ | $CH_3$ | H | H | H | H | H | H | N | N | O | $OCH_3$ |
| 2  | $CH_3$ | $CH_3$ | $OCH_3$ | H | H | H | H | H | N | N | O | $OCH_3$ |
| 3  | $CH_3$ | $CH_3$ | H | $OCH_3$ | H | $OCH_3$ | H | H | N | N | O | $OCH_3$ |
| 4  | $CH_3$ | $CH_3$ | Et | H | H | H | H | H | N | N | O | $OCH_3$ |
| 5  | $CH_3$ | $CH_3$ | H | H | n-Bu | H | H | H | N | N | O | $OCH_3$ |
| 6  | $CH_3$ | $CH_3$ | iPr | H | H | H | H | H | N | N | O | $OCH_3$ |
| 7  | $CH_3$ | $CH_3$ | H | $CH_3$ | H | $CH_3$ | H | H | N | N | O | $OCH_3$ |
| 8  | $CH_3$ | $CH_3$ | $CH_3$ | $CH_3$ | H | $CH_3$ | $CH_3$ | H | N | N | O | $OCH_3$ |
| 9  | $CH_3$ | $CH_3$ | F | H | H | H | H | H | N | N | O | $OCH_3$ |
| 10 | $CH_3$ | $CH_3$ | H | Br | H | H | H | H | N | N | O | $OCH_3$ |
| 11 | $CH_3$ | $CH_3$ | H | Cl | H | Cl | H | H | N | N | O | $OCH_3$ |
| 12 | $CH_3$ | $CH_3$ | H | F | H | F | H | H | N | N | O | $OCH_3$ |
| 13 | $CH_3$ | $CH_3$ | H | $CF_3$ | H | H | H | H | N | N | O | $OCH_3$ |
| 14 | $CH_3$ | $CH_3$ | $SCH_3$ | H | H | H | H | H | N | N | O | $OCH_3$ |

-continued

| Ex | R₁ | R₂ | R₃ | R₄ | R₅ | R₆ | R₇ | R₈ | X₁ | X₂ | Y | Z |
|---|---|---|---|---|---|---|---|---|---|---|---|---|
| 15 | CH₃ | CH₃ | H | NO₂ | H | NO₂ | H | H | N | N | O | OCH₃ |
| 16 | CH₃ | CH₃ | H | NH₂ | H | NH₂ | H | H | N | N | O | OCH₃ |
| 17 | CH₃ | CH₃ | H | H | Ac | H | H | H | N | N | O | OCH₃ |
| 18 | CH₃ | CH₃ | OCH₃ | H | H | H | H | CH₃ | N | N | O | OCH₃ |
| 19 | CH₃ | CH₃ | H | OCH₃ | H | OCH₃ | H | CH₃ | N | N | O | OCH₃ |
| 20 | CH₃ | CH₃ | H | CH₃ | H | CH₃ | H | CH₃ | N | N | O | OCH₃ |
| 21 | CH₃ | CH₃ | H | Cl | H | Cl | H | CH₃ | N | N | O | OCH₃ |
| 22 | CH₃ | CH₃ | H | F | H | F | H | CH₃ | N | N | O | OCH₃ |
| 23 | CH₃ | CH₃ | SCH₃ | H | H | H | H | CH₃ | N | N | O | OCH₃ |
| 24 | CH₃ | CH₃ | H | NO₂ | H | NO₂ | H | CH₃ | N | N | O | OCH₃ |
| 25 | CH₃ | CH₃ | H | NH₂ | H | NH₂ | H | CH₃ | N | N | O | OCH₃ |
| 26 | CH₃ | CH₃ | H | OCH₃ | H | OCH₃ | H | Et | N | N | O | OCH₃ |
| 27 | CH₃ | CH₃ | H | CH₃ | H | CH₃ | H | Et | N | N | O | OCH₃ |
| 28 | CH₃ | CH₃ | H | OCH₃ | H | OCH₃ | H | H | N | N | S | OCH₃ |
| 29 | CH₃ | CH₃ | Et | H | H | H | H | H | N | N | S | OCH₃ |
| 30 | CH₃ | CH₃ | H | CH₃ | H | CH₃ | H | H | N | N | S | OCH₃ |
| 31 | CH₃ | CH₃ | H | Br | H | H | H | H | N | N | S | OCH₃ |
| 32 | CH₃ | CH₃ | H | Cl | H | Cl | H | H | N | N | S | OCH₃ |
| 33 | CH₃ | CH₃ | SCH₃ | H | H | H | H | H | N | N | S | OCH₃ |
| 34 | Et | Et | H | CH₃ | H | CH₃ | H | H | N | N | O | OCH₃ |
| 35 | Et | Et | H | OCH₃ | H | OCH₃ | H | H | N | N | O | OCH₃ |
| 36 | CH=CH—CH=CH | | H | H | H | H | H | H | N | N | O | OCH₃ |
| 37 | CH=CH—CH=CH | | OCH₃ | H | H | H | H | H | N | N | O | OCH₃ |
| 38 | CH=CH—CH=CH | | H | OCH₃ | H | OCH₃ | H | H | N | N | O | OCH₃ |
| 39 | CH=CH—CH=CH | | Et | H | H | H | H | H | N | N | O | OCH₃ |
| 40 | CH=CH—CH=CH | | iPr | H | H | H | H | H | N | N | O | OCH₃ |
| 41 | CH=CH—CH=CH | | H | H | nBu | H | H | H | N | N | O | OCH₃ |
| 42 | CH=CH—CH=CH | | H | CH₃ | H | CH₃ | H | H | N | N | O | OCH₃ |
| 43 | CH=CH—CH=CH | | CH₃ | CH₃ | H | CH₃ | CH₃ | H | N | N | O | OCH₃ |
| 44 | CH=CH—CH=CH | | F | H | H | H | H | H | N | N | O | OCH₃ |
| 45 | CH=CH—CH=CH | | H | Br | H | H | H | H | N | N | O | OCH₃ |
| 46 | CH=CH—CH=CH | | H | F | H | F | H | H | N | N | O | OCH₃ |
| 47 | CH=CH—CH=CH | | H | CF₃ | H | H | H | H | N | N | O | OCH₃ |
| 48 | CH=CH—CH=CH | | H | NO₂ | H | NO₂ | H | H | N | N | O | OCH₃ |
| 49 | CH=CH—CH=CH | | H | NH₂ | H | NH₂ | H | H | N | N | O | OCH₃ |
| 50 | CH=CH—CH=CH | | H | H | Ac | H | H | H | N | N | O | OCH₃ |
| 51 | CH=CH—CH=CH | | SCH₃ | H | H | H | H | H | N | N | O | OCH₃ |
| 52 | CH=CH—CH=CH | | Ph | H | H | H | H | H | N | N | O | OCH₃ |
| 53 | CH=CH—CH=CH | | H | OCH₃ | H | OCH₃ | H | CH₃ | N | N | O | OCH₃ |
| 54 | CH=CH—CH=CH | | OCH₃ | H | H | H | H | CH₃ | N | N | O | OCH₃ |
| 55 | CH=CH—CH=CH | | H | CH₃ | H | CH₃ | H | CH₃ | N | N | O | OCH₃ |
| 56 | CH=CH—CH=CH | | H | F | H | F | H | CH₃ | N | N | O | OCH₃ |
| 57 | CH=CH—CH=CH | | H | NO₂ | H | NO₂ | H | CH₃ | N | N | O | OCH₃ |
| 58 | CH=CH—CH=CH | | H | NH₂ | H | NH₂ | H | CH₃ | N | N | O | OCH₃ |
| 59 | CH=CH—CH=CH | | H | OCH₃ | H | OCH₃ | H | Et | N | N | O | OCH₃ |
| 60 | CH=CH—CH=CH | | H | CH₃ | H | CH₃ | H | Et | N | N | O | OCH₃ |
| 61 | CH=CH—CH=CH | | H | Cl | H | Cl | H | Et | N | N | O | OCH₃ |
| 62 | CH=CH—CH=CH | | H | OCH₃ | H | OCH₃ | H | iPr | N | N | O | OCH₃ |
| 63 | CH=CH—CH=CH | | OCH₃ | H | H | H | H | H | N | N | S | OCH₃ |
| 64 | CH=CH—CH=CH | | F | OCH₃ | H | OCH₃ | H | H | N | N | S | OCH₃ |
| 65 | CH=CH—CH=CH | | Et | H | H | H | H | H | N | N | S | OCH₃ |
| 66 | CH=CH—CH=CH | | H | CH₃ | H | CH₃ | H | H | N | N | S | OCH₃ |
| 67 | CH=CH—CH=CH | | H | Br | H | H | H | H | N | N | S | OCH₃ |
| 68 | CH=CH—CH=CH | | H | F | H | F | H | H | N | N | S | OCH₃ |
| 69 | CH=CH—CH=CH | | SCH₃ | H | H | H | H | H | N | N | S | OCH₃ |
| 70 | CH=CH—CH=CH | | H | H | Ac | H | H | H | N | N | S | OCH₃ |
| 71 | CH=CH—CH=CH | | H | H | nBu | H | H | H | N | N | S | OCH₃ |
| 72 | CH=CH—CH=CH | | H | OCH₃ | H | OCH₃ | H | H | N | N | O | OEt |
| 73 | CH=CH—CH=CH | | OEt | H | H | H | H | H | N | N | O | OEt |
| 74 | CH=CH—CH=CH | | H | CH₃ | H | CH₃ | H | H | N | N | O | OEt |
| 75 | CH=CH—CH=CH | | CH₃ | CH₃ | H | H | H | H | N | N | O | OEt |
| 76 | CH=CH—CH=CH | | Et | H | H | H | H | H | N | N | O | OEt |
| 77 | CH=CH—CH=CH | | H | Cl | H | Cl | H | H | N | N | O | OEt |
| 78 | CH=CH—CH=CH | | H | Br | H | H | H | H | N | N | O | OEt |
| 79 | CH=CH—CH=CH | | H | F | H | F | H | H | N | N | O | OEt |
| 80 | CH=CH—CH=CH | | SCH₃ | H | H | H | H | H | N | N | O | OEt |
| 81 | CH=CH—CH=CH | | H | OCH₃ | H | OCH₃ | H | CH₃ | N | N | O | OEt |
| 82 | CH=CH—CH=CH | | H | Cl | H | Cl | H | CH₃ | N | N | O | OEt |
| 83 | CH=CH—CH=CH | | H | OCH₃ | H | OCH₃ | H | Et | N | N | O | OEt |
| 84 | CH=CH—CH=CH | | H | Cl | H | Cl | H | Et | N | N | O | OEt |
| 85 | CH=CH—CH=CH | | H | CH₃ | H | CH₃ | H | Et | N | N | O | OEt |
| 86 | CH=CH—CH=CH | | H | CH₃ | H | CH₃ | H | H | C | C | O | OCH₃ |
| 87 | CH=CH—CH=CH | | H | OCH₃ | H | OCH₃ | H | H | C | C | O | OCH₃ |
| 88 | CH=CH—CH=CH | | H | F | H | F | H | H | C | C | O | OCH₃ |
| 89 | CH=CH—CH=CH | | H | Cl | H | Cl | H | H | C | C | O | OCH₃ |
| 90 | CH=CH—CH=CH | | H | CH₃ | H | CH₃ | H | CH₃ | C | C | O | OCH₃ |
| 91 | CH=CH—CH=CH | | H | F | H | F | H | CH₃ | C | C | O | OCH₃ |

-continued

| Ex | R₁ | R₂ | R₃ | R₄ | R₅ | R₆ | R₇ | R₈ | X₁ | X₂ | Y | Z |
|---|---|---|---|---|---|---|---|---|---|---|---|---|
| 92 | CH=CH—CH=CH | | H | Cl | H | Cl | H | CH₃ | C | C | O | OCH₃ |
| 93 | CH=CH—CH=CH | | H | OCH₃ | H | OCH₃ | H | CH₃ | C | C | O | OCH₃ |
| 94 | CH=CH—CH=CH | | H | OCH₃ | H | OCH₃ | H | Et | C | C | O | OCH₃ |
| 95 | CH=CH—CH=CH | | H | CH₃ | H | CH₃ | H | Et | C | C | O | OCH₃ |

The compounds of the general formula (Ib) were prepared in the following examples according to the above-described process.

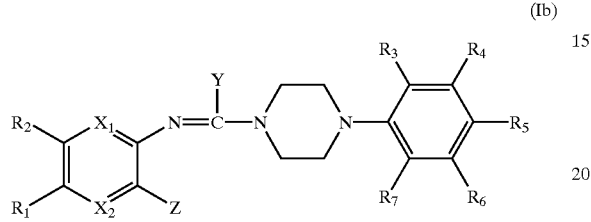

(Ib)

wherein, R₁, R₂, R₃, R₄, R₅, R₆, R₇, X, Y and Z are as defined above.

| Ex. | R₁ | R₂ | R₃ | R₄ | R₅ | R₆ | R₇ | X₁ | X₂ | Y | Z |
|---|---|---|---|---|---|---|---|---|---|---|---|
| 96 | CH₃ | CH₃ | H | H | H | H | H | C | N | NHOH | OCH₃ |
| 97 | CH₃ | CH₃ | H | H | CH₃ | H | H | C | N | NHOH | OCH₃ |
| 98 | CH₃ | CH₃ | H | H | nBu | H | H | C | N | NHOH | OCH₃ |
| 99 | CH₃ | CH₃ | H | CH₃ | H | CH₃ | H | C | N | NHOH | OCH₃ |
| 100 | CH₃ | CH₃ | OCH₃ | H | H | H | H | C | N | NHOH | OCH₃ |
| 104 | CH₃ | CH₃ | H | OCH₃ | H | OCH₃ | H | C | N | NHOH | OCH₃ |
| 102 | CH₃ | CH₃ | H | F | H | F | H | C | N | NHOH | OCH₃ |
| 103 | CH₃ | CH₃ | H | Cl | H | Cl | H | C | N | NHOH | OCH₃ |
| 104 | CH₃ | CH₃ | H | Br | H | H | H | C | N | NHOH | OCH₃ |
| 105 | CH₃ | CH₃ | H | NO₂ | H | NO₂ | H | C | N | NHOH | OCH₃ |
| 106 | CH₃ | CH₃ | H | C(=O)OEt | H | C(=O)OEt | H | C | N | NHOH | OCH₃ |
| 107 | CH₃ | CH₃ | H | CH₂CH₂OH | H | CH₂CH₂OH | H | C | N | NHOH | OCH₃ |
| 108 | CH₃ | Et | OCH₃ | H | H | H | H | C | N | NHOH | OCH₃ |
| 109 | CH₃ | Et | H | OCH₃ | H | OCH₃ | H | C | N | NHOH | OCH₃ |
| 110 | CH₃ | Et | Et | H | H | H | H | C | N | NHOH | OCH₃ |
| 111 | CH₃ | Et | H | H | H | H | H | C | N | NHOH | OCH₃ |
| 112 | CH₃ | Et | SCH₃ | H | H | H | H | C | N | NHOH | OCH₃ |
| 113 | CH₃ | Et | H | CH₃ | H | CH₃ | H | C | N | NHOH | OCH₃ |
| 114 | CH₃ | Et | H | F | H | F | H | C | N | NHOH | OCH₃ |
| 115 | CH₃ | Et | H | Cl | H | Cl | H | C | N | NHOH | OCH₃ |
| 116 | CH₃ | Et | Ph | H | H | H | H | C | N | NHOH | OCH₃ |
| 117 | CH₃ | Et | H | NO₂ | H | NO₂ | H | C | N | NHOH | OCH₃ |
| 118 | CH₃ | C(=O)OCH₃ | H | OCH₃ | H | OCH₃ | H | C | N | NHOH | OCH₃ |
| 119 | CH₃ | C(=O)OCH₃ | H | CH₃ | H | CH₃ | H | C | N | NHOH | OCH₃ |
| 120 | CH₃ | C(=O)OCH₃ | H | F | H | F | H | C | N | NHOH | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 121 | CH₃ | CH₂C(O)OCH₃ | OCH₃ | H | H | H | H | C | N | NHOH | OCH₃ |
| 122 | CH₃ | CH₂C(O)OCH₃ | H | H | H | H | H | C | N | NHOH | OCH₃ |
| 123 | CH₃ | CH₂C(O)OCH₃ | H | H | CH₃ | H | H | C | N | NHOH | OCH₃ |
| 124 | CH₃ | CH₂C(O)OCH₃ | H | Cl | H | H | H | C | N | NHOH | OCH₃ |
| 125 | CH₃ | CH₂CH₂OH | H | OCH₃ | H | OCH₃ | H | C | N | NHOH | OCH₃ |
| 126 | CH₃ | CH₂CH₂OH | H | CH₃ | H | CH₃ | H | C | N | NHOH | OCH₃ |
| 127 | CH₃ | CH₂CH₂OH | H | F | H | F | H | C | N | NHOH | OCH₃ |
| 128 | CH₃ | CH₂CH₂OH | OCH₃ | H | H | H | H | C | N | NHOH | OCH₃ |
| 129 | CH₃ | CH₂CH₂OH | H | H | H | H | H | C | N | NHOH | OCH₃ |
| 130 | CH₃ | CH₂CH₂OH | H | H | CH₃ | H | H | C | N | NHOH | OCH₃ |
| 131 | CH₃ | CH₂CH₂OH | H | Cl | H | H | H | C | N | NHOH | OCH₃ |
| 132 | CH₃ | C(O)CH₃ | H | CH₃ | H | CH₃ | H | C | N | NHOH | OCH₃ |
| 133 | CH₃ | C(O)CH₃ | H | OCH₃ | H | OCH₃ | H | C | N | NHOH | OCH₃ |
| 134 | CH₃ | C(O)CH₃ | H | H | H | H | H | C | N | NHOH | OCH₃ |
| 135 | CH₃ | C(O)CH₃ | H | H | CH₃ | H | H | C | N | NHOH | OCH₃ |
| 136 | CH₃ | C(O)CH₃ | H | F | H | F | H | C | N | NHOH | OCH₃ |
| 137 | CH₃ | C(O)CH₃ | SCH₃ | H | H | H | H | C | N | NHOH | OCH₃ |
| 138 | CH₃ | CH(OH)CH₃ | H | CH₃ | H | CH₃ | H | C | N | NHOH | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 139 | CH₃ | isopropyl-OH | H | OCH₃ | H | OCH₃ | H | C | N | NHOH | OCH₃ |
| 140 | CH₃ | isopropyl-OH | H | H | H | H | H | C | N | NHOH | OCH₃ |
| 141 | CH₃ | isopropyl-OH | H | H | CH₃ | H | H | C | N | NHOH | OCH₃ |
| 142 | CH₃ | isopropyl-OH | H | F | H | F | H | C | N | NHOH | OCH₃ |
| 143 | CH₃ | isopropyl-OH | SCH₃ | H | H | H | H | C | N | NHOH | OCH₃ |
| 144 | CH₃ | =NOH (isopropylidene) | H | CH₃ | H | CH₃ | H | C | N | NHOH | OCH₃ |
| 145 | CH₃ | =NOH (isopropylidene) | H | F | H | F | H | C | N | NHOH | OCH₃ |
| 146 | CH₃ | =NOH (isopropylidene) | H | F | H | F | H | C | N | NHOH | OCH₃ |
| 147 | CH₃ | =NOH (isopropylidene) | SCH₃ | H | H | H | H | C | N | NHOH | OCH₃ |
| 148 | CH₃ | =NOH (isopropylidene) | H | NO₂ | H | NO₂ | H | C | N | NHOH | OCH₃ |
| 149 | CH₃ | =NOH (isopropylidene) | H | H | CH₃ | H | H | C | N | NHOH | OCH₃ |
| 150 | CH₃ | isopropyl-NH₂ | H | CH₃ | H | CH₃ | H | C | N | NHOH | OCH₃ |
| 151 | CH₃ | isopropyl-NH₂ | H | OCH₃ | H | OCH₃ | H | C | N | NHOH | OCH₃ |
| 152 | CH₃ | isopropyl-NH₂ | H | F | H | F | H | C | N | NHOH | OCH₃ |
| 153 | CH₃ | isopropyl-NH₂ | SCH₃ | H | H | H | H | C | N | NHOH | OCH₃ |
| 154 | CH₃ | isopropyl-NH₂ | H | NO₂ | H | NO₂ | H | C | N | NHOH | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 155 | CH₃ |  | H | Cl | H | Cl | H | C | N | NHOH | OCH₃ |
| 156 | Et | 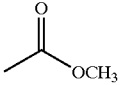 | H | H | CH₃ | H | H | C | N | NHOH | OCH₃ |
| 157 | Et | 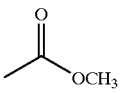 | Et | H | H | H | H | C | N | NHOH | OCH₃ |
| 158 | Et | 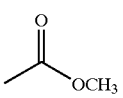 | H | CH₃ | H | CH₃ | H | C | N | NHOH | OCH₃ |
| 159 | Et | 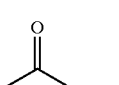 | H | OCH₃ | H | OCH₃ | H | C | N | NHOH | OCH₃ |
| 160 | Et | 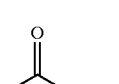 | H | Cl | H | Cl | H | C | N | NHOH | OCH₃ |
| 161 | Et | 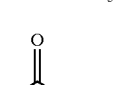 | SCH₃ | H | H | H | H | C | N | NHOH | OCH₃ |
| 162 | Et | 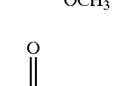 | H | 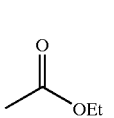 | H | 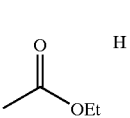 | H | C | N | NHOH | OCH₃ |
| 163 | Et | 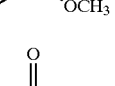 | H | F | H | F | H | C | N | NHOH | OCH₃ |
| 164 | Et | 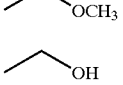 | H | H | CH₃ | H | H | C | N | NHOH | OCH₃ |
| 165 | Et | 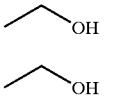 | Et | H | H | H | H | C | N | NHOH | OCH₃ |
| 166 | Et | 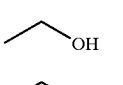 | H | CH₃ | H | CH₃ | H | C | N | NHOH | OCH₃ |
| 167 | Et | 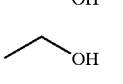 | H | OCH₃ | H | OCH₃ | H | C | N | NHOH | OCH₃ |
| 168 | Et | 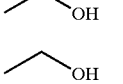 | H | Cl | H | Cl | H | C | N | NHOH | OCH₃ |
| 169 | Et | 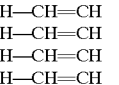 | SCH₃ | H | H | H | H | C | N | NHOH | OCH₃ |
| 170 | Et | 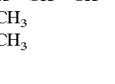 | H | 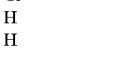 | H |  | H | C | N | NHOH | OCH₃ |
| 171 | Et |  | H | F | H | F | H | C | N | NHOH | OCH₃ |
| 172 | CH=CH—CH=CH | | H | OCH₃ | H | OCH₃ | H | C | N | NHOH | OCH₃ |
| 173 | CH=CH—CH=CH | | H | CH₃ | H | CH₃ | H | C | N | NHOH | OCH₃ |
| 174 | CH=CH—CH=CH | | H | F | H | F | H | C | N | NHOH | OCH₃ |
| 175 | CH=CH—CH=CH | | OCH₃ | H | H | H | H | C | N | NHOH | OCH₃ |
| 176 | CH=CH—CH=CH | | H | Cl | H | H | H | C | N | NHOH | OCH₃ |
| 177 | CH₃ | CH₃ | H | H | H | H | H | C | C | NHOH | OCH₃ |
| 178 | CH₃ | CH₃ | H | H | CH₃ | H | H | C | C | NHOH | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 179 | CH₃ | CH₃ | Et | H | H | H | H | C | C | NHOH | OCH₃ |
| 180 | CH₃ | CH₃ | H | CH₃ | H | CH₃ | H | C | C | NHOH | OCH₃ |
| 181 | CH₃ | CH₃ | H | OCH₃ | H | OCH₃ | H | C | C | NHOH | OCH₃ |
| 182 | CH₃ | CH₃ | H | F | H | F | H | C | C | NHOH | OCH₃ |
| 183 | CH₃ | CH₃ | H | Cl | H | H | H | C | C | NHOH | OCH₃ |
| 184 | CH₃ | CH₃ | H | Br | H | H | H | C | C | NHOH | OCH₃ |
| 185 | CH₃ | CH₃ | SCH₃ | H | H | H | H | C | C | NHOH | OCH₃ |
| 186 | CH₃ | CH₃ | H | H | H | H | H | C | N | NHOCH₃ | OCH₃ |
| 187 | CH₃ | CH₃ | H | H | CH₃ | H | H | C | N | NHOCH₃ | OCH₃ |
| 188 | CH₃ | CH₃ | H | CH₃ | H | CH₃ | H | C | N | NHOCH₃ | OCH₃ |
| 189 | CH₃ | CH₃ | H | OCH₃ | H | OCH₃ | H | C | N | NHOCH₃ | OCH₃ |
| 190 | CH₃ | CH₃ | H | F | H | F | H | C | N | NHOCH₃ | OCH₃ |
| 191 | CH₃ | CH₃ | SCH₃ | H | H | H | H | C | N | NHOCH₃ | OCH₃ |
| 192 | CH₃ | CH₃ | H | NO₂ | H | NO₂ | H | C | N | NHOCH₃ | OCH₃ |
| 193 | CH₃ | Et | H | Cl | H | Cl | H | C | N | NHOCH₃ | OCH₃ |
| 194 | Et | —C(=O)OCH₃ | H | F | H | F | H | C | N | NHOCH₃ | OCH₃ |
| 195 | Et | —C(=O)OCH₃ | H | —C(=O)OEt | H | —C(=O)OEt | H | C | N | NHOCH₃ | OCH₃ |
| 196 | Et | —CH₂CH₂OH | H | —CH₂CH₂OH | H | —CH₂CH₂OH | H | C | N | NHOCH₃ | OCH₃ |
| 197 | CH₃ | CH₃ | H | H | CH₃ | H | H | C | C | NHOCH₃ | OCH₃ |
| 198 | CH₃ | CH₃ | H | CH₃ | H | CH₃ | H | C | C | NHOCH₃ | OCH₃ |
| 199 | CH₃ | CH₃ | H | H | H | H | H | C | N | SCH₃ | OCH₃ |
| 200 | CH₃ | CH₃ | H | H | CH₃ | H | H | C | N | SCH₃ | OCH₃ |
| 201 | CH₃ | CH₃ | H | H | nBu | H | H | C | N | SCH₃ | OCH₃ |
| 202 | CH₃ | CH₃ | H | CH₃ | H | CH₃ | H | C | N | SCH₃ | OCH₃ |
| 203 | CH₃ | CH₃ | OCH₃ | H | H | H | H | C | N | SCH₃ | OCH₃ |
| 204 | CH₃ | CH₃ | H | OCH₃ | H | OCH₃ | H | C | N | SCH₃ | OCH₃ |
| 205 | CH₃ | CH₃ | H | F | H | F | H | C | N | SCH₃ | OCH₃ |
| 206 | CH₃ | CH₃ | H | Cl | H | Cl | H | C | N | SCH₃ | OCH₃ |
| 207 | CH₃ | CH₃ | H | Br | H | H | H | C | N | SCH₃ | OCH₃ |
| 208 | CH₃ | CH₃ | H | NO₂ | H | NO₂ | H | C | N | SCH₃ | OCH₃ |
| 209 | CH₃ | CH₃ | H | —C(=O)OEt | H | —C(=O)OEt | H | C | N | SCH₃ | OCH₃ |
| 210 | CH₃ | Et | H | H | H | H | H | C | N | SCH₃ | OCH₃ |
| 211 | CH₃ | Et | OCH₃ | H | H | H | H | C | N | SCH₃ | OCH₃ |
| 212 | CH₃ | Et | H | OCH₃ | H | OCH₃ | H | C | N | SCH₃ | OCH₃ |
| 213 | CH₃ | Et | Et | H | H | H | H | C | N | SCH₃ | OCH₃ |
| 214 | CH₃ | Et | H | CH₃ | H | CH₃ | H | C | N | SCH₃ | OCH₃ |
| 215 | CH₃ | Et | H | F | H | F | H | C | N | SCH₃ | OCH₃ |
| 216 | CH₃ | Et | H | Cl | H | Cl | H | C | N | SCH₃ | OCH₃ |
| 217 | CH₃ | Et | Ph | H | H | H | H | C | N | SCH₃ | OCH₃ |
| 218 | CH₃ | Et | H | NO₂ | H | NO₂ | H | C | N | SCH₃ | OCH₃ |
| 219 | CH₃ | Et | SCH₃ | H | H | H | H | C | N | SCH₃ | OCH₃ |
| 220 | CH₃ | —C(=O)OCH₃ | H | OCH₃ | H | OCH₃ | H | C | N | SCH₃ | OCH₃ |
| 221 | CH₃ | —C(=O)OCH₃ | H | CH₃ | H | CH₃ | H | C | N | SCH₃ | OCH₃ |
| 222 | CH₃ | —C(=O)OCH₃ | H | F | H | F | H | C | N | SCH₃ | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 223 | CH₃ | 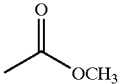 | OCH₃ | H | H | H | H | C | N | SCH₃ | OCH₃ |
| 224 | CH₃ | 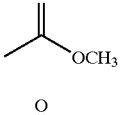 | H | H | H | H | H | C | N | SCH₃ | OCH₃ |
| 225 | CH₃ | 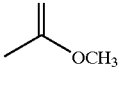 | H | H | CH₃ | H | H | C | N | SCH₃ | OCH₃ |
| 226 | CH₃ | 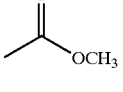 | H | Cl | H | H | H | C | N | SCH₃ | OCH₃ |
| 227 | CH₃ | 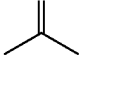 | H | CH₃ | H | CH₃ | H | C | N | SCH₃ | OCH₃ |
| 228 | CH₃ | 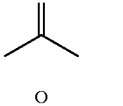 | H | OCH₃ | H | OCH₃ | H | C | N | SCH₃ | OCH₃ |
| 229 | CH₃ | 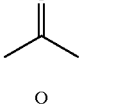 | H | H | H | H | H | C | N | SCH₃ | OCH₃ |
| 230 | CH₃ | 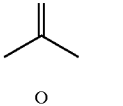 | H | H | CH₃ | H | H | C | N | SCH₃ | OCH₃ |
| 231 | CH₃ | 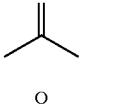 | H | F | H | F | H | C | N | SCH₃ | OCH₃ |
| 232 | CH₃ | 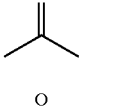 | SCH₃ | H | H | H | H | C | N | SCH₃ | OCH₃ |
| 233 | Et | 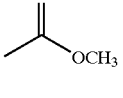 | H | H | CH₃ | H | H | C | N | SCH₃ | OCH₃ |
| 234 | Et | 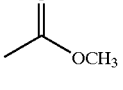 | Et | H | H | H | H | C | N | SCH₃ | OCH₃ |
| 235 | Et | 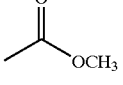 | H | CH₃ | H | CH₃ | H | C | N | SCH₃ | OCH₃ |
| 236 | Et | 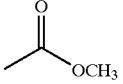 | H | OCH₃ | H | OCH₃ | H | C | N | SCH₃ | OCH₃ |
| 237 | Et | 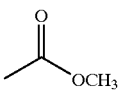 | H | Cl | H | Cl | H | C | N | SCH₃ | OCH₃ |

-continued

| Ex. | R₁ | R₂ | R₃ | R₄ | R₅ | R₆ | R₇ | X₁ | X₂ | Y | Z |
|---|---|---|---|---|---|---|---|---|---|---|---|
| 238 | Et | –C(=O)OCH₃ | SCH₃ | H | H | H | H | C | N | SCH₃ | OCH₃ |
| 239 | Et | –C(=O)OCH₃ | H | –C(=O)OEt | H | –C(=O)OEt | H | C | N | SCH₃ | OCH₃ |
| 240 | Et | –C(=O)OCH₃ | H | F | H | F | H | C | N | SCH₃ | OCH₃ |
| 241 | CH=CH—CH=CH | | H | OCH₃ | H | OCH₃ | H | C | N | SCH₃ | OCH₃ |
| 242 | CH=CH—CH=CH | | H | CH₃ | H | CH₃ | H | C | N | SCH₃ | OCH₃ |
| 243 | CH=CH—CH=CH | | H | F | H | F | H | C | N | SCH₃ | OCH₃ |
| 244 | CH=CH—CH=CH | | OCH₃ | H | H | H | H | C | N | SCH₃ | OCH₃ |
| 245 | CH=CH—CH=CH | | H | Cl | H | H | H | C | N | SCH₃ | OCH₃ |
| 246 | CH₃ | CH₃ | H | H | H | H | H | C | C | SCH₃ | OCH₃ |
| 247 | CH₃ | CH₃ | H | H | CH₃ | H | H | C | C | SCH₃ | OCH₃ |
| 248 | CH₃ | CH₃ | Et | H | H | H | H | C | C | SCH₃ | OCH₃ |
| 249 | CH₃ | CH₃ | H | CH₃ | H | CH₃ | H | C | C | SCH₃ | OCH₃ |
| 250 | CH₃ | CH₃ | H | OCH₃ | H | OCH₃ | H | C | C | SCH₃ | OCH₃ |
| 251 | CH₃ | CH₃ | H | F | H | F | H | C | C | SCH₃ | OCH₃ |
| 252 | CH₃ | CH₃ | H | Cl | H | H | H | C | C | SCH₃ | OCH₃ |
| 253 | CH₃ | CH₃ | H | Br | H | H | H | C | C | SCH₃ | OCH₃ |
| 254 | CH₃ | CH₃ | SCH₃ | H | H | H | H | C | C | SCH₃ | OCH₃ |

EXAMPLE 1)

1-[(5,6-Dimethyl-2-methoxypyrazin-3-yl) aminocarbonyl]-4-phenylpiperazine a) Phenyl N-(5,6-dimethyl-2-methoxypyrazin-3-yl) carbamate:

3-Amino-5,6-dimethyl-2-methoxypyrazine (1.00 g, 6.53 mmol) and phenylchloroformate (1.02 g, 6.53 mmol) were dissolved in dichloromethane and stirred at room temperature for 2 hours. The resulting mixture was concentrated under the reduced pressure to remove the solvent and purified by column chromatography to obtain the titled compound.

yield: 98%
m.p.: 101~103° C.

b) 1-[(5,6-Dimethyl-2-methoxypyrazin-3-yl) aminocarbonyl]-4-phenyl piperazine:

Phenyl N-(5,6-dimethyl-2-methoxypyrazin-3-yl) carbamate (350 mg, 1.28 mmol) and 1-phenylpiperazine (208 mg, 1.28 mmol) were dissolved in anhydrous tetrahydrofuran and thereto DBU (195 mg, 1.28 mmol) was added. The resulting mixture was stirred at room temperature for 2 hours and concentrated under the reduced pressure to remove the solvent, and purified by column chromatography to obtain the titled compound.

yield: 78.5%
m.p.: 185~187° C.

EXAMPLE 2)

1-[(5,6-Dimethyl-2-methoxypyrazin-3-yl) aminocarbonyl]-4-(2-methoxyphenyl)piperazine Phenyl N-(5,6-dimethyl-2-methoxypyrazin-3-yl) carbamate and 1-(2-methoxyphenyl)piperazine were reacted by the same way with the example 1 to obtain the titled compound.

yield: 82.0%
m.p.: 184~185° C.

EXAMPLE 3)

1-[(5,6-Dimethyl-2-methoxypyrazin-3-yl) aminocarbonyl]-4-(3,5-dimethoxyphenyl)piperazine Phenyl N-(5,6-dimethyl-2-methoxypyrazin-3-yl) carbamate and 1-(3,5-dimethoxyphenyl)piperazine were reacted by the same way with the example 1 to obtain the titled compound.

yield: 85.0%
m.p.: 136~137° C.

EXAMPLE 4)

1-[(5,6-Dimethyl-2-methoxypyrazin-3-yl) aminocarbonyl]-4-(2-ethylphenyl)piperazine Phenyl N-(5,6-dimethyl-2-methoxypyrazin-3-yl) carbamate and 1-(2-ethylphenyl)piperazine were reacted by the same way with the example 1 to obtain the titled compound.

yield: 70.4%
m.p.: 197~199° C.

EXAMPLE 5)

1-[(5,6-Dimethyl-2-methoxypyrazin-3-yl) aminocarbonyl]-4-(4-butylphenyl)piperazine Phenyl N-(5,6-dimethyl-2-methoxypyrazin-3-yl) carbamate and 1-)4-butylphenyl)piperazine were reacted by the same way with the example 1 to obtain the titled compound.

yield: 68.5%
m.p.: 121~123° C.

EXAMPLE 6)

1-[(5,6-Dimethyl-2-methoxypyrazin-3-yl) aminocarbonyl]-4-(2-isopropylphenyl)piperazine Phenyl N-(5,6-dimethyl-2-methoxypyrazin-3-yl) carbamate and 1-(2-isopropylphenyl)piperazine were reacted by the same way with the example 1 to obtain the titled compound.

yield: 73.0% m.p.: 165~167° C.

EXAMPLE 7)

1-[(5,6-Dimethyl-2-methoxypyrazin-3-yl)aminocarbonyl]-4-(3,5-dimethylphenyl)piperazine Phenyl N-(5,6-dimethyl-2-methoxypyrazin-3-yl)carbamate and 1-(3,5-dimethylphenyl)piperazine were reacted by the same way with the example 1 to obtain the titled compound.

yield: 84.0% m.p.: 162~164° C.

EXAMPLE 8)

1-[(5,6-Dimethyl-2-methoxypyrazin-3-yl)aminocarbonyl]-4-(2,3,5,6-tetramethylphenyl)piperazine Phenyl N-(5,6-dimethyl-2-methoxypyrazin-3-yl)carbamate and 1-(2,3,5,6,-tetramethylphenyl)piperazine were reacted by the same way with the example 1 to obtain the titled compound.

yield: 65.5% m.p.: 202~204° C.

EXAMPLE 9)

1-[(5,6-Dimethyl-2-methoxypyrazin-3-yl)aminocarbonyl]-4-(2-fluorophenyl)piperazine Phenyl N-(5,6-dimethyl-2-methoxypyrazin-3-yl)carbamate and 1-(2-fluorophenyl)piperazine were reacted by the same way with the example 1 to obtain the titled compound.

yield: 74.5% m.p.: 170~172° C.

EXAMPLE 10)

1-[(5,6-Dimethyl-2-methoxypyrazin-3-yl)aminocarbonyl]-4-(3-bromophenyl)piperazine Phenyl N-(5,6-dimethyl-2-methoxypyrazin-3-yl)carbamate and 1-(3-bromophenyl)piperazine were reacted by the same way with the example 1 to obtain the titled compound.

yield: 70.0% m.p.: 158~160° C.

EXAMPLE 11)

1-[(5,6-Dimethyl-2-methoxypyrazin-3-yl)aminocarbonyl]-4-(3,5-dichlorophenyl)piperazine Phenyl N-(5,6-dimethyl-2-methoxypyrazin-3-yl)carbamate and 1-(3,5-dichlorophenyl)piperazine were reacted by the same way with the example 1 to obtain the titled compound.

yield: 80.5% m.p.: 180~181° C.

EXAMPLE 12)

1-[(5,6-Dimethyl-2-methoxypyrazin-3-yl)aminocarbonyl]-4-(3,5-difluorophenyl)piperazine Phenyl N-(5,6-dimethyl-2-methoxypyrazin-3-yl)carbamate and 1-(3,5-difluorophenyl)piperazine were reacted by the same way with the example 1 to obtain the titled compound.

yield: 78.0% m.p.: 153~154° C.

EXAMPLE 13)

1-[(5,6-Dimethyl-2-methoxypyrazin-3-yl)aminocarbonyl]-4-(3-trifluorotolyl)piperazine Phenyl N-(5,6-dimethyl-2-methoxypyrazin-3-yl)carbamate and 1-(3-trifluorotolyl)piperazine were reacted by the same way with the example 1 to obtain the titled compound.

yield: 69.5% m.p.: 168~170° C.

EXAMPLE 14)

1-[(5,6-Dimethyl-2-methoxypyrazin-3-yl)aminocarbonyl]-4-(2-methylthiophenyl)piperazine Phenyl N-(5,6-dimethyl-2-methoxypyrazin-3-yl)carbamate and 1-(2-methylthiophenyl)piperazine were reacted by the same way with the example 1 to obtain the titled compound.

yield: 71.0% m.p.: 202~204° C.

EXAMPLE 15)

1-[(5,6-Dimethyl-2-methoxypyrazin-3-yl)aminocarbonyl]-4-(3,5-dinitrophenyl)piperazine Phenyl N-(5,6-dimethyl-2-methoxypyrazin-3-yl)carbamate and 1-(3,5-dinitrophenyl)piperazine were reacted by the same way with the example 1 to obtain the titled compound.

yield: 64.5% m.p.: 192~194° C.

EXAMPLE 16)

1-[(5,6-Dimethyl-2-methoxypyrazin-3-yl)aminocarbonyl]-4-(3,5-diaminophenyl)piperazine 1-[(5,6-Dimethyl-2-methoxypyrazin-3-yl)aminocarbonyl]-4-(3,5-dinitrophenyl)piperazine was dissolved in ethanol (30 ml) and thereto 10% palladium/carbon (10 mg) was added. The resulting mixture was hydrogenated for 4 hours, and then filtered to remove the 10% palladium/carbon. The filtrate was concentrated and purified by column chromatography to obtain the titled compound.

yield: 45.0% m.p.: >100° C. (decomposed)

EXAMPLE 17)

1-[(5,6-Dimethyl-2-methoxypyrazin-3-yl)aminocarbonyl]-4-(4-acetylphenyl)piperazine Phenyl N-(5,6-dimethyl-2-methoxypyrazin-3-yl)carbamate and 1-(4-acetylphenyl)piperazine were reacted by the same way with the example 1 to obtain the titled compound.

yield : 71.5% m.p.: 166~168° C.

EXAMPLE 18)

1-[(5,6-Dimethyl-2-methoxypyrazin-3-yl)N-methylaminocarbonyl]-4-(2-methoxyphenyl)piperazine 1-[(5,6-Dimethyl-2-methoxypyrazin-3-yl)aminocarbonyl]-4-(2-methoxyphenyl)piperazine (200 mg, 0.54 mmol) was dissolved in dimethylformamide (15 ml) and thereto 60% sodium hydride (21.5 mg, 0.54 mmol) was added. The resulting mixture was stirred at room temperature for 15 minutes, and thereto methyl iodide (76.6 mg, 0.54 mmol) was added. The resulting mixture was stirred at room temperature for 6 hours, concentrated under the reduced pressure to remove the solvent, and purified by column chromatography to obtain the titled compound.

yield: 92.5% m.p.: 140~142° C.

EXAMPLE 19)

1-[(5,6-Dimethyl-2-methoxypyrazin-3-yl)N-methylaminocarbonyl]-4-(3,5-dimethoxyphenyl)piperazine 1-[(5,6-Dimethyl-2-methoxypyrazin-3-yl)aminocarbonyl]-4-(3,5-dimethoxyphenyl)piperazine was reacted by the same way with the example 18 to obtain the titled compound.

yield: 90.5% m.p.: 80~82° C.

EXAMPLE 20)

1-[(5,6-Dimethyl-2-methoxypyrazin-3-yl)N-methylaminocarbonyl]-4-(3,5-dimethylphenyl)piperazine 1-[(5,6-Dimethyl-2-methoxypyrazin-3-yl)aminocarbonyl]-4-(3,5-dimethylphenyl)piperazine was reacted by the same way with the example 18 to obtain the titled compound.

yield: 88.4% m.p.: 94~96° C.

EXAMPLE 21)

1-[(5,6-Dimethyl-2-methoxypyrazin-3-yl)N-methylaminocarbonyl]-4-(3,5-dichlorophenyl)piperazine 1-[(5,6-Dimethyl-2-methoxypyrazin-3-yl)aminocarbonyl]-4-(3,5-dichlorophenyl)piperazine was reacted by the same way with the example 18 to obtain the titled compound.

yield: 95.2% m.p.: 97~99° C.

EXAMPLE 22)

1-[(5,6-Dimethyl-2-methoxypyrazin-3-yl)N-methylaminocarbonyl]-4-(3,5-difluorophenyl)piperazine 1-[(5,6-Dimethyl-2-methoxypyrazin-3-yl)aminocarbonyl]-4-(3,5-difluorophenyl)piperazine was reacted by the same way with the example 18 to obtain the titled compound.

yield: 94.0% m.p.: 104~106° C.

EXAMPLE 23)

1-[(5,6-Dimethyl-2-methoxypyrazin-3-yl)N-methylaminocarbonyl]-4-(2-methylthiophenyl)piperazine 1-[(5,6-Dimethyl-2-methoxypyrazin-3-yl)aminocarbonyl]-4-(2-methylthiophenyl)piperazine was reacted by the same way with the example 18 to obtain the titled compound.

yield: 89.5% m.p.: 133~134° C.

EXAMPLE 24)

1-[(5,6-Dimethyl-2-methoxypyrazin-3-yl)N-methylaminocarbonyl]-4-(3,5-dinitrophenyl)piperazine 1-[(5,6-Dimethyl-2-methoxypyrazin-3-yl)aminocarbonyl]-4-(3,5-dinitrophenyl)piperazine was reacted by the same way with the example 18 to obtain the titled compound.

yield: 80.0% m.p.: 133~135° C.

EXAMPLE 25)

1-[(5,6-Dimethyl-2-methoxypyrazin-3-yl)N-methylaminocarbonyl]-4-(3,5-diaminophenyl)piperazine 1-[(5,6-Dimethyl-2-methoxypyrazin-3-yl)N-methylaminocarbonyl]-4-(3,5-dinitrophenyl)piperazine was reacted by the same way with the example 18 to obtain the titled compound.

yield: 58.5% m.p.: >100° C. (decomposed)

EXAMPLE 26)

1-[(5,6-Dimethyl-2-methoxypyrazin-3-yl)N-ethylaminocarbonyl]-4-(3,5-dimethoxyphenyl)piperazine 1-[(5,6-Dimethyl-2-methoxypyrazin-3-yl)aminocarbonyl]-4-(3,5-dimethoxyphenyl)piperazine (250 mg, 0.62 mmol) was dissolved in dimethylformamide (20 ml) and thereto 60% sodium hydride (24.9 mg, 0.62 mmol) was added. The mixture was stirred at room temperature for 15 minutes, and thereto methyl iodide (96.7 mg, 0.62 mmol) was added. The resulting mixture was stirred at room temperature for 6 hours, concentrated under the reduced pressure to remove the solvent used, and purified by column chromatography to obtain the titled compound.

yield: 89.5% m.p.: 78~80° C.

EXAMPLE 27)

1-[(5,6-Dimethyl-2-methoxypyrazin-3-yl)N-ethylaminocarbonyl]-4-(3,5-dimethylphenyl)piperazine 1-[(5,6-Dimethyl-2-methoxypyrazin -3-yl)aminocarbonyl]-4-(3,5-dimethylphenyl)piperazine was reacted by the same way with the example 26 to obtain the titled compound.

yield: 92.0% m.p.: 68~70° C.

EXAMPLE 28)

1-[(5,6-Dimethyl-2-methoxypyrazin-3-yl)aminothiocarbonyl]-4-(3,5-dimethoxyphenyl)piperazine a) Phenyl N-(5,6-dimethyl-2-methoxypyrazin-3-yl)thiocarbamate:

3-Amino-5,6-dimethyl-2-methoxypyrazine (500 mg, 3.26 mmol) was dissolved in dichloromethane and thereto phenyl thiochloroformate (564 mg, 3.26 mmol) was slowly added. The mixture was stirred at room temperature for 24 hours, concentrated under the reduced pressure to remove the solvent, and purified by column chromatography to obtain the titled compound.

yield: 78.5%
m.p.: 71~73° C.

b) 1-[(5,6-Dimethyl-2-methoxypyrazin-3-yl)aminothiocarbonyl]-4-(3,5-dimethoxyphenyl)piperazine:

Phenyl N-(5,6-dimethyl-2-methoxypyrazin-3-yl)thiocarbamate (200 mg, 0.69 mmol) and 1-(3,5-dimethoxyphenyl)piperazine (154 mg, 0.69 mmol) were dissolved in anhydrous tetrahydrofuran (25 ml) and thereto DBU (105 mg, 0.69 mmol) was added. The mixture was stirred at room temperature for 2 hours, concentrated under the reduced pressure to remove the solvent and purified by column chromatography to obtain the titled compound.

yield: 71.5%
m.p.: 183~184° C.

EXAMPLE 29)

1-[(5,6-Dimethyl-2-methoxypyrazin-3-yl)aminothiocarbonyl]-4-(2-ethylphenyl)piperazine Phenyl N-(5,6-dimethyl-2-methoxypyrazin-3-yl)thiocarbamate and 1-(2-ethylphenyl)piperazine were reacted by the same way with the example 28 to obtain the titled compound.

yield: 64.0%
m.p.: 197~199° C.

EXAMPLE 30)

1-[(5,6-Dimethyl-2-methoxypyrazin-3-yl)aminothiocarbonyl]-4-(3,5-dimethylphenyl)piperazine Phenyl N-(5,6-dimethyl-2-methoxypyrazin-3-yl)thiocarbamate and 1-(3,5-dimethylphenyl)piperazine were reacted by the same way with the example 28 to obtain the titled compound.

yield: 68.4%
m.p.: 160~162° C.

EXAMPLE 31)

1-[(5,6-Dimethyl-2-methoxypyrazin-3-yl)aminothiocarbonyl]-4-(3-bromophenyl)piperazine Phenyl N-(5,6-dimethyl-2-methoxypyrazin-3-yl)thiocarbamate and 1-(3-bromophenyl)piperazine were reacted by the same way with the example 28 to obtain the titled compound.

yield: 62.5%
m.p.: 136~138° C.

EXAMPLE 32)

1-[(5,6-Dimethyl-2-methoxypyrazin-3-yl)aminothiocarbonyl]-4-(3,5-dichlorophenyl)piperazine Phenyl N-(5,6-dimethyl-2-methoxypyrazin-3-yl)thiocarbamate and 1-(3,5-dichlorophenyl)piperazine were reacted by the same way with the example 28 to obtain the titled compound.

yield: 70.8%
m.p.: 182~184° C.

EXAMPLE 33)

1-[(5,6-Dimethyl-2-methoxypyrazin-3-yl)aminothiocarbonyl]-4-(2-methylthiophenyl)piperazine Phenyl N-(5,6-dimethyl-2-methoxypyrazin-3-yl)thiocarbamate and 1-(2-methylthiophenyl)piperazine were reacted by the same way with the example 28 to obtain the titled compound.

yield: 61.4%
m.p.: 181~183° C.

EXAMPLE 34)

1-[(5,6-Dichloroethyl-2-methoxypyrazin-3-yl)aminocarbonyl]-4-(3,5-dimethylphenyl)piperazine Phenyl N-(5,6-diethyl-2-methoxypyrazin-3-yl)carbamate and 1-(3,5-dimethylphenyl)piperazine were reacted by the same way with the example 1 to obtain the titled compound.

yield: 77.5%
m.p.: 118~120° C.

EXAMPLE 35)

1-[(5,6-Dichloroethyl-2-methoxypyrazin-3-yl)aminocarbonyl]-4-(3,5-dimethoxyphenyl)piperazine Phenyl N-(5,6-diethyl-2-methoxypyrazin-3-yl)carbamate and 1-(3,5-dimethoxyphenyl)piperazine were reacted by the same way with the example 1 to obtain the titled compound.

yield: 78.9%
m.p.: 90~92° C.

EXAMPLE 36)

1-[(2-Methoxyquinoxalin-3-yl)aminocarbonyl]-4-phenylpiperazine a) Phenyl N-(2-methoxyquinoxalin-3-yl)carbamate:

3-Amino-2-methoxyquinoxaline (1.00 g, 6.53 mmol) and phenylchloroformate (1.02 g, 6.53 mmol) were dissolved in dichloromethane and stirred at room temperature for 2 hours. The resulting mixture was concentrated under the reduced pressure to remove the solvent, and purified by column chromatography to obtain the titled compound.

yield: 75.5%
m.p.: 147~149° C.

b) 1-[(2-Methoxyquinoxalin-3-yl)aminocarbonyl]-4-phenylpiperazine:

Phenyl N-(2-methoxyquinoxalin-3-yl)carbamate (378 mg, 1.28 mmol) and 1-phenylpiperazine (208 mg, 1.28 mmol) were dissolved in anhydrous tetrahydrofuran and thereto DBU (195 mg, 1.28 mmol) was added. The mixture was stirred at room temperature for 2 hours, concentrated under the reduced pressure to remove the solvent, and purified by column chromatography to obtain the titled compound.

yield: 76.5%
m.p.: 156~158° C.

EXAMPLE 37)

1-[(2-Methoxyquinoxalin-3-yl)aminocarbonyl]-4-(2-methoxyphenyl)-piperazine

Phenyl N-(2-Methoxyquinoxalin-3-yl)carbamate and 1-(2-methoxyphenyl)piperazine were reacted by the same way with the example 36 to obtain the titled compound.

yield: 72.4%
m.p.: 177~178° C.

EXAMPLE 38)

1-[(2-Methoxyquinoxalin-3-yl)aminocarbonyl]-4-(3,5-dimethoxyphenyl)piperazine

Phenyl N-(2-methoxyquinoxalin-3-yl)carbamate and 1-(3,5-dimethoxy-phenyl)piperazine were reacted by the same way with the example 36 to obtain the titled compound.

yield: 81.2%
m.p.: 140~141° C.

EXAMPLE 39)

1-[(2-Methoxyquinoxalin-3-yl)aminocarbonyl]-4-(2-ethylphenyl)piperazine

Phenyl N-(2-methoxyquinoxalin-3-yl)carbamate and 1-(2-ethylphenyl)piperazine were reacted by the same way with the example 36 to obtain the titled compound.
yield: 75.0%
m.p.: 191~193° C.

EXAMPLE 40)

1-[(2-Methoxyquinoxalin-3-yl)aminocarbonyl]-4-(2-isoprop-ylphenyl)piperazine

Phenyl N-(2-methoxyquinoxalin-3-yl)carbamate and 1-(2-isopropylphenyl)piperazine were reacted by the same way with the example 36 to obtain the titled compound.
yield: 77.5%
m.p.: 147~149° C.

EXAMPLE 41)

1-[(2-Methoxyquinoxalin-3-yl)aminocarbonyl]-4-(4-butylph-enyl)-piperazine

Phenyl N-(2-methoxyquinoxalin-3-yl)carbamate and 1-(4-butylphenyl)-piperazine were reacted by the same way with the example 36 to obtain the titled compound.
yield: 65.4%
m.p.: 124~126° C.

EXAMPLE 42)

1-[(2-Methoxyquinoxalin-3-yl)aminocarbonyl]-4-(3,5-dimethylphenyl)piperazine

Phenyl N-(2-methoxyquinoxalin-3-yl)carbamate and 1-(3,5-dimethylphenyl)piperazine were reacted by the same way with the example 36 to obtain the titled compound.
yield: 79.3%
m.p.: 155~157° C.

EXAMPLE 43)

1-[(2-Methoxyquinoxalin-3-yl)aminocarbonyl]-4-(2,3,5,6-tetramethylphenyl)piperazine Phenyl N-(2-methoxyquinoxalin-3-yl)carbamate and 1-(2,3,5,6-tetramethylphenyl)piperazine were reacted by the same way with the example 36 to obtain the titled compound.
yield: 64.0%
m.p.: 237~239° C.

EXAMPLE 44)

1-[(2-Methoxyquinoxalin-3-yl)aminocarbonyl]-4-(2-fluorop-henyl)piperazine

Phenyl N-(2-methoxyquinoxalin-3-yl)carbamate and 1-(2-fluorophenyl)-piperazine were reacted by the same way with the example 36 to obtain the titled compound.
yield: 67.5%
m.p.: 142~144° C.

EXAMPLE 45)

1-[(2-Methoxyquinoxalin-3-yl)aminocarbonyl]-4-(3-bromop-henyl)piperazine

Phenyl N-(2-methoxyquinoxalin-3-yl)carbamate and 1-(3-bromophenyl)-piperazine were reacted by the same way with the example 36 to obtain the titled compound.
yield: 69.5%
m.p.: 148~150° C.

EXAMPLE 46)

1-[(2-Methoxyquinoxalin-3-yl)aminocarbonyl]-4-(3,5-difluo-rophenyl)piperazine

Phenyl N-(2-methoxyquinoxalin-3-yl)carbamate and 1-(3,5-difluorophenyl)piperazine were reacted by the same way with the example 36 to obtain the titled compound.
yield: 74.5%
m.p.: 172~173° C.

EXAMPLE 47)

1-[(2-Methoxyquinoxalin-3-yl)aminocarbonyl]-4-(2-trifluorotolyl)piperazine

Phenyl N-(2-methoxyquinoxalin-3-yl)carbamate and 1-(2-trifluorotolyl)-piperazine were reacted by the same way with the example 36 to obtain the titled compound.
yield: 70.7%
m.p.: 132~134° C.

EXAMPLE 48)

1-[(2-Methoxyquinoxalin-3-yl)aminocarbonyl]-4-(3,5-dinitrophenyl)piperazine

Phenyl N-(2-methoxyquinoxalin-3-yl)carbamate and 1-(3,5-dinitrophenyl)piperazine were reacted by the same way with the example 36 to obtain the titled compound.
yield: 54.5%
m.p.: 216~218° C.

EXAMPLE 49)

1-[(2-Methoxyquinoxalin-3-yl)aminocarbonyl]-4-(3,5-diami-nophenyl)piperazine

1-[(2-Methoxyquinoxalin-3-yl)aminocarbonyl]-4-(3,5-dinitrophenyl)piperazine (200 mg, 0.44 mmol) was dissolved in ethanol (30 ml) and thereto 10% palladium/carbon (10 mg) was added. The mixture was hydrogenated for 4 hours, and then filtered to remove the 10% palladium/carbon. The filtrate was concentrated and purified by column chromatography to obtain the titled compound.
yield : 42.5%
m.p.: >100° C. (decomposed)

EXAMPLE 50)

1-[(2-Methoxyquinoxalin-3-yl)aminocarbonyl]-4-(4-acetylp-henyl)piperazine

Phenyl N-(2-methoxyquinoxalin-3-yl)carbamate and 1-(4-acetylphenyl)-piperazine were reacted by the same way with the example 36 to obtain the titled compound.
yield: 71.0%
m.p.: 198~200° C.

EXAMPLE 51)

1-[(2-Methoxyquinoxalin-3-yl)aminocarbonyl]-4-(2-methylt-hiophenyl)piperazine

Phenyl N-(2-methoxyquinoxalin-3-yl)carbamate and 1-(2-methylthiophenyl)piperazine were reacted by the same way with the example 36 to obtain the titled compound.

yield: 69.8%
m.p.: 180~182° C.

EXAMPLE 52)

1-[(2-Methoxyquinoxalin-3-yl)aminocarbonyl]-4-(2-biphen-yl)piperazine

Phenyl N-(2-methoxyquinoxalin-3-yl)carbamate and 1-(2-biphenyl)piperazine were reacted by the same way with the example 36 to obtain the titled compound.

yield: 59.0%
m.p.:162~165° C.

EXAMPLE 53)

1-[(2-Methoxyquinoxalin-3-yl) N-methylaminocarbonyl]-4-(3,5-dimethoxyphenyl)piperazine 1-[(2-Methoxyquinoxalin-3-yl)aminocarbonyl]-4-(2-methoxyphenyl) piperazine (229 mg, 0.54 mmol) was dissolved in dimethylformamide (15 ml) and thereto 60% sodium hydride (21.5 mg, 0.54 mmol) was added. The mixture was stirred at room temperature for 15 minutes, and thereto ehtyl iodide (76.6 mg, 0.54 mmol) was, added. The mixture was stirred at room temperature for 6 hours, concentrated under the reduced pressure to remove the solvent and purified by column chromatography to obtain the titled compound.

yield: 92.5%
m.p.: 143~144° C.

EXAMPLE 54)

1-[(2-Methoxyquinoxalin-3-yl)N-methylaminocarbonyl]-4-(2-methoxyphenyl)piperazine 1-[(2-Methoxyquinoxalin-3-yl)aminocarbonyl]-4-(2-methoxyphenyl)piperazine was reacted by the same way with the example 53 to obtain the titled compound.

yield: 83.8%
m.p.: 128~130° C.

EXAMPLE 55)

1-[(2-Methoxyquinoxalin-3-yl)N-methylaminocarbonyl]-4-(3,5-dimethylphenyl)piperazine 1-[(2-Methoxyquinoxalin-3-yl)aminocarbonyl]-4-(3,5-dimethylphenyl)piperazine was reacted by the same way with the example 53 to obtain the titled compound.

yield: 86.5%
m.p.: 142~144° C.

EXAMPLE 56)

1-[(2-Methoxyquinoxalin-3-yl)N-methylaminocarbonyl]-4-(3,5-difluorophenyl)piperazine 1-[(2-Methoxyquinoxalin-3-yl)aminocarbonyl]-4-(3,5-difluorophenyl) piperazine was reacted by the same way with the example 53 to obtain the titled compound.

yield: 84.7%
m.p.: 197~199° C.

EXAMPLE 57)

1-[(2-Methoxyquinoxalin-3-yl)N-methylaminocarbonyl]-4-(3,5-dinitrophenyl)piperazine 1-[(2-Methoxyquinoxalin-3-yl)aminocarbonyl]-4-(3,5-dinitrophenyl)piperazine was reacted by the same way with the example 53 to obtain the titled compound.

yield: 56.5%
m.p.: 197~199° C.

EXAMPLE 58)

1-[(2-Methoxyquinoxalin-3-yl)N-methylaminocarbonyl]-4-(3,5-diaminophenyl)piperazine To 1-[(2-methoxyquinoxalin-3-yl)N-methylaminocarbonyl]-4-(3,5-dinitrophenyl)piperazine dissolved in ethanol (30 ml), 10% palladium/carbon (10 mg) was added. The mixture was hydrogenated for 4 hours, and then filtered to remove the 10% palladium/carbon. The filtrate was concentrated and purified by column chromatography to obtain the titled compound.

yield: 44.5%
m.p.: >100° C. (decomposed)

EXAMPLE 59)

1-[(2-Methoxyquinoxalin-3-yl)N-ethylaminocarbonyl]-4-(3,5-dimethoxyphenyl)piperazine To 1-[(2-methoxyquinoxalin-3-yl)aminocarbonyl]-4-(3,5-dimethoxyphenyl)piperazine (263 mg, 0.62 mmol) dissolved in dimethylformamide (20 ml), 60% sodium hydride (24.9 mg, 0.62 mmol) was added and stirred at room temperature for 15 minutes, and thereto methyl iodide (96.7 mg, 0.62 mmol) was added. The resulting mixture was stirred at room temperature for 6 hours, concentrated under the reduced pressure to remove the solvent and purified by column chromatography to obtain the titled compound.

yield: 85.4%
m.p.: 129~130° C.

EXAMPLE 60)

1-[(2-Methoxyquinoxalin-3-yl)N-ethylaminocarbonyl]-4-(3,5-dimethylphenyl)piperazine 1-[(2-Methoxyquinoxalin-3-yl)aminocarbonyl]-4-(3,5-dimethylphenyl)piperazine was reacted by the same way with the example 59 to obtain the titled compound.

yield: 87.6%
m.p.: 145~147° C.

EXAMPLE 61)

1-[(2-Methoxyquinoxalin-3-yl)N-ethylaminocarbonyl]-4-(3,5-dichlorophenyl)piperazine 1-[(2-Methoxyquinoxalin-3-yl)aminocarbonyl]-4-(3,5-dichlorophenyl)piperazine were reacted by the same way with the example 59 to obtain the titled compound.

EXAMPLE 62)

1-[(2-Methoxyquinoxalin-3-yl)N-isopropylaminocarbonyl]-4-(3,5-dimethoxyphenyl)piperazine To 1-[(2-methoxyquinoxalin-3-yl)aminocarbonyl]-4-(3,5-dimethoxyphenyl)piperazine (216 mg, 0.51 mmol) dissolved in dimethylformamide (20 ml), 60% sodium hydride (20.4 mg, 0.51 mmol) was added and stirred at room temperature for 15 minutes, and thereto propyl iodide (86.7 mg, 0.51 mmol) was added. The resulting mixture was stirred at room temperature for 6 hours, concentrated under the reduced pressure to remove the solvent and purified by column chromatography to obtain the titled compound.

yield: 82.0%
m.p.: 110~112° C.

EXAMPLE 63)

1-[(2-Methoxyquinoxalin-3-yl)aminothiocarbonyl]-4-(2-met-hoxyphenyl)piperazine a) Phenyl N-(2-Methoxyquinoxalin-3-yl)thiocarbamate:

To 3-Amino-2-Methoxyquinoxaline (571 mg, 3.26 mmol) dissolved in dichloromethane, phenylthiochloroformate (564 mg, 3.26 mmol) were added slowly and stirred at room temperature for 24 hours. The resulting mixture was concentrated under the reduced pressure to remove the solvent and purified by column chromatography to obtain the titled compound.

yield: 60.5%
m.p.: 160~162° C.

b) 1-[(2-Methoxyquinoxalin-3-yl)aminothiocarbonyl]-4-(2-methoxyphenyl)piperazine:

Phenyl N-(2-methoxyquinoxalin-3-yl)thiocarbamate (215 mg, 0.69 mmol) and 1-(2-methoxyphenyl)piperazine (154 mg, 0.69 mmol) were dissolved in anhydrous tetrahydrofuran (25 ml) and thereto DBU (105 mg, 0.69 mmol) was added. The mixture was stirred at room temperature for 2 hours, concentrated under the reduced pressure to remove the solvent and purified by column chromatography to obtain the titled compound.

yield: 62.4%
m.p.: 177~179° C.

EXAMPLE 64)

1-[(2-Methoxyquinoxalin-3-yl)aminothiocarbonyl]-4-(3,5-dimethoxyphenyl)piperazine Phenyl N-(2-methoxyquinoxalin-3-yl)thiocarbamate and 1-(3,5-dimethoxyphenyl)piperazine were reacted by the same way with the example 63 to obtain the titled compound.

yield: 64.5%
m.p.: 141~143° C.

EXAMPLE 65)

1-[(2-Methoxyquinoxalin-3-yl)aminothiocarbonyl]-4-(2-ethylphenyl)piperazine

Phenyl N-(2-methoxyquinoxalin-3-yl)thiocarbamate and 1-(2-ethylphenyl)piperazine were reacted by the same way with the example 63 to obtain the titled compound.

yield: 60.7%
m.p.: 141~143° C.

EXAMPLE 66)

1-[(2-Methoxyquinoxalin-3-yl)aminothiocarbonyl]-4-(3,5-di-methylphenyl)piperazine Phenyl N-(2-methoxyquinoxalin-3-yl)thiocarbamate and 1-(3,5-dimethylphenyl)piperazine were reacted by the same way with the example 63 to obtain the titled compound.

yield: 65.0%
m.p.: 193~195° C.

EXAMPLE 67)

1-[(2-Methoxyquinoxalin-3-yl)aminothiocarbonyl]-4-(3-bro-mophenyl)piperazine

Phenyl N-(2-methoxyquinoxalin-3-yl)thiocarbamate and 1-(3-bromophenyl)piperazine were reacted by the same way with the example 63 to obtain the titled compound.

yield: 57.5%
m.p.: 195~197° C.

EXAMPLE 68)

1-[(2-Methoxyquinoxalin-3-yl)aminothiocarbonyl]-4-(3,5-difluorophenyl)piperazine Phenyl N-(2-methoxyquinoxalin-3-yl)thiocarbamate and 1-(3,5-difluorophenyl)piperazine were reacted by the same way with the example 63 to obtain the titled compound.

yield: 59.0%
m.p.: 280~281° C.

EXAMPLE 69)

1-[(2-Methoxyquinoxalin-3-yl)aminothiocarbonyl]-4-(2-methylthiophenyl)piperazine Phenyl N-(2-methoxyquinoxalin-3-yl)thiocarbamate and 1-(2-methylthiophenyl)piperazine were reacted by the same way with the example 63 to obtain the titled compound.

yield: 64.5%
m.p.: 148~150° C.

EXAMPLE 70)

1-[(2-Methoxyquinoxalin-3-yl)aminothiocarbonyl]-4-(4-acetylphenyl)piperazine

Phenyl N-(2-methoxyquinoxalin-3-yl)thiocarbamate and 1-(4-acetylphenyl)piperazine were reacted by the same way with the example 63 to obtain the titled compound.

yield: 56.9%
m.p.: 235~237° C.

EXAMPLE 71)

1-[(2-Methoxyquinoxalin-3-yl)aminothiocarbonyl]-4-(4-but-ylphenyl)piperazine

Phenyl N-(2-methoxyquinoxalin-3-yl)thiocarbamate and 1-(4-butylphenyl)piperazine were reacted by the same way with the example 63 to obtain the titled compound.

yield: 62.5%
m.p.: 163~165° C.

EXAMPLE 72)

1-[(2-Ethoxyquinoxalin-3-yl)aminocarbonyl]-4-(3,5-dimethoxyphenyl)piperazine

Phenyl N-(2-ethoxyquinoxalin-3-yl)carbamate and 1-(3,5-dimethoxyphenyl)piperazine were reacted by the same way with the example 36 to obtain the titled compound.
yield: 74.7%
m.p.: 149~150° C.

EXAMPLE 73)

1-[(2-Ethoxyquinoxalin-3-yl)aminocarbonyl]-4-(2-ethoxyphenyl)piperazine

Phenyl N-(2-ethoxyquinoxalin-3-yl)carbamate and 1-(2-ethoxyphenyl)-piperazine were reacted by the same way with the example 36 to obtain the titled compound.
yield: 76.5%
m.p.: 120~122° C.

EXAMPLE 74)

1-[(2-Ethoxyquinoxalin-3-yl)aminocarbonyl]-4-(3,5-dimethylphenyl)piperazine

Phenyl N-(2-ethoxyquinoxalin-3-yl)carbamate and 1-(3,5-dimethylphenyl)piperazine were reacted by the same way with the example 36 to obtain the titled compound.
yield: 82.0%
m.p.: 152~154° C.

EXAMPLE 75)

1-[(2-Ethoxyquinoxalin-3-yl)aminocarbonyl]-4-(2,3-dimethylphenyl)piperazine

Phenyl N-(2-ethoxyquinoxalin-3-yl)carbamate and 1-(2,3-dimethylphenyl)piperazine were reacted by the same way with the example 36 to obtain the titled compound.
yield: 78.7%
m.p.: 108~110° C.

EXAMPLE 76)

1-[(2-Ethoxyquinoxalin-3-yl)aminocarbonyl]-4-(2-ethylphenyl)piperazine

Phenyl N-(2-ethoxyquinoxalin-3-yl)carbamate and 1-(2-ethylphenyl)piperazine were reacted by the same way with the example 36 to obtain the titled compound.
yield: 77.5%
m.p.: 152~154° C.

EXAMPLE 77)

1-[(2-Ethoxyquinoxalin-3-yl)aminocarbonyl]-4-(3,5-dichlorophenyl)piperazine

Phenyl N-(2-ethoxyquinoxalin-3-yl)carbamate and 1-(3,5-dichlorophenyl)piperazine were reacted by the same way with the example 36 to obtain the titled compound.
yield: 81.3%
m.p.: 157~159° C.

EXAMPLE 78)

1-[(2-Ethoxyquinoxalin-3-yl)aminocarbonyl]-4-(3-bromophenyl)piperazine

Phenyl N-(2-ethoxyquinoxalin-3-yl)carbamate and 1-(3-bromophenyl)-piperazine were reacted by the same way with the example 36 to obtain the titled compound.
yield: 80.6%
m.p.: 164~166° C.

EXAMPLE 79)

1-[(2-Ethoxyquinoxalin-3-yl)aminocarbonyl]-4-(3,5-difluorophenyl)piperazine

Phenyl N-(2-ethoxyquinoxalin-3-yl)carbamate and 1-(3,5-difluorophenyl)piperazine were reacted by the same way with the example 36 to obtain the titled compound.
yield: 78.6%
m.p.: 146~148° C.

EXAMPLE 80)

1-[(2-Ethoxyquinoxalin-3-yl)aminocarbonyl]-4-(2-methylthiophenyl)piperazine

Phenyl N-(2-ethoxyquinoxalin-3-yl)carbamate and 1-(2-methylthiophenyl)piperazine were reacted by the same way with the example 36 to obtain the titled compound.
yield: 71.4%
m.p.: 139~141° C.

EXAMPLE 81)

1-[(2-Ethoxyquinoxalin-3-yl)N-methylaminocarbonyl]-4-(3,5-dimethoxyphenyl)piperazine 1-[(2-Ethoxyquinoxalin-3-yl)aminocarbonyl]-4-(3,5-dimethoxyphenyl)piperazine was reacted by the same way with the example 53 to obtain the titled compound.
yield: 92.8%
m.p.: 159~161° C.

EXAMPLE 82)

1-[(2-Ethoxyquinoxalin-3-yl)N-methylaminocarbonyl]-4-(3,5-dichlorophenyl)piperazine 1-[(2-Ethoxyquinoxalin-3-yl)aminocarbonyl]-4-(3,5-dichlorophenyl) piperazine was reacted by the same way with the example 53 to obtain the titled compound.
yield: 94.5%
m.p.: 129~131° C.

EXAMPLE 83)

1-[(2-Ethoxyquinoxalin-3-yl)N-ethylaminocarbonyl]-4-(3,5-dimethoxyphenyl)piperazine 1-[(2-Ethoxyquinoxalin-3-yl)aminocarbonyl]-4-(3,5-dimethoxyphenyl)piperazine was reacted by the same way with the example 61 to obtain the titled compound.
yield: 82.8%
m.p.: 144~146° C.

EXAMPLE 84)

1-[(2-Ethoxyquinoxalin-3-yl)N-ethylaminocarbonyl]-4-(3,5-dichlorophenyl)piperazine 1-[(2-Ethoxyquinoxalin-3-yl)aminocarbonyl]-4-(3,5-dichlorophenyl)piperazine was reacted by the same way with the example 61 to obtain the titled compound.

yield: 80.7%
m.p.: 115~117° C.

EXAMPLE 85)

1-[(2-Ethoxyquinoxalin-3-yl)N-ethylaminocarbonyl]-4-(3,5-dimethylphenyl)piperazine 1-[(2-Ethoxyquinoxalin-3-yl)aminocarbonyl]-4-(3,5-dimethylphenyl)piperazine was reacted by the same way with the example 61 to obtain the titled compound.
yield: 78.8%
m.p.: 142~144° C.

EXAMPLE 86)

1-[(2-Methoxynaphth-3-yl)aminocarbonyl]-4-(3,5-dimethylphenyl)piperazine a) Phenyl N-(2-methoxynaphth-3-yl)carbamate:
3-Amino-2-methoxynaphthalene (1.13 g, 6.53 mmol) and phenylchloroformate (1.02 g, 6.53 mmol) were dissolved in dichloromethane. The mixture was stirred at room temperature for 2 hours, concentrated under the reduced pressure to remove the solvent and purified by column chromatography to obtain the titled compound.
yield: 75.0%
m.p.: 105~107° C.

b) 1-[(2-Methoxynaphth-3-yl)aminothiocarbonyl]-4-(3,5-dimethylphenyl-piperazine:
Phenyl N-(2-methoxynaphth-3-yl)carbamate (375 mg, 1.28 mmol) and 1-(3,5-dimethylphenyl)piperazine (208 mg, 1.28 mmol) were dissolved in anhydrous tetrahydrofuran (25 ml) and thereto DBU (195 mg, 1.28 mmol) was added, and then stirred at room temperature for 2 hours, concentrated under the reduced pressure to remove the solvent and purified by column chromatography to obtain the titled compound.
yield: 72.0%
m.p.: 117~119° C.

EXAMPLE 87)

1-[(2-Methoxynaphth-3-yl)aminocarbonyl]-4-(3,5-dimethoxyphenyl)piperazine

Phenyl N-(2-methoxynaphth-3-yl)carbamate and 1-(3,5-dimethoxyphenyl)piperazine were reacted by the same way with the example 86 to obtain the titled compound.
yield: 74.5%
m.p.: 191~193° C.

EXAMPLE 88)

1-[(2-Methoxynaphth-3-yl)aminocarbonyl]-4-(3,5-difluorophenyl)piperazine

Phenyl N-(2-methoxynaphth-3-yl)carbamate and 1-(3,5-difluorophenyl)piperazine were reacted by the same way with the example 86 to obtain the titled compound.
yield: 78.5%
m.p.: 160~161° C.

EXAMPLE 89)

1-[(2-Methoxynaphth-3-yl)aminocarbonyl]-4-(3,5-dichlorophenyl)piperazine

Phenyl N-(2-methoxynaphth-3-yl)carbamate and 1-(3,5-dichlorophenyl)piperazine were reacted by the same way with the example 86 to obtain the titled compound.

yield: 76.7%
m.p.: 182~184 ° C.

EXAMPLE 90)

1-[(2-Methoxynaphth-3-yl)-N-methylaminocarbonyl]-4-(3,5-dimethylphenyl)piperazine To 1-[(2-methoxynaphth-3-yl)aminocarbonyl]-4-(3,5-dimethylphenyl)piperazine (210 mg, 0.54 mmol) dissolved in dimethylformamide (15 ml), 60% sodium hydride (21.5 mg, 0.54 mmol) was added, stirred at room temperature for 15 minutes, and thereto methyl iodide (76.6 mg, 0.54 mmol) was added. The resulting mixture was stirred at room temperature for 6 hours, concentrated under the reduced pressure to remove the solvent and purified by column chromatography to obtain the titled compound.
yield: 86.4%
m.p.: 134~136° C.

EXAMPLE 91)

1-[(2-Methoxynaphth-3-yl)-N-methylaminocarbonyl]-4-(3,5-difluorophenyl)piperazine 1-[(2-Methoxynaphth-3-yl)aminocarbonyl]-4-(3,5-difluorophenyl)piperazine was reacted by the same way with the example 90 to obtain the titled compound.
yield: 85.0%
m.p.: 115~117° C.

EXAMPLE 92)

1-[(2-Methoxynaphth-3-yl)-N-methylaminocarbonyl]-4-(3,5-dichlorophenyl)piperazine 1-[(2-Methoxynaphth-3-yl)aminocarbonyl]-4-(3,5-dichlorophenyl)piperazine was reacted by the same way with the example 90 to obtain the titled compound.
yield: 89.8%
m.p.: 165~167° C.

EXAMPLE 93)

1-[(2-Methoxynaphth-3-yl)-N-methylaminocarbonyl]-4-(3,5-dimethoxyphenyl)piperazine 1-[(2-Methoxynaphth-3-yl)aminocarbonyl]-4-(3,5-dimethoxyphenyl)piperazine was reacted by the same way with the example 90 to obtain the titled compound.
yield: 92.5%
m.p.: 83~85° C.

EXAMPLE 94)

1-[(2-Methoxynaphth-3-yl)-N-ethylaminocarbonyl]-4-(3,5-dimethylphenyl)piperazine To 1-[(2-methoxynaphth-3-yl)aminocarbonyl]-4-(3,5-dimethylphenyl)piperazine (210 mg, 0.54 mmol) dissolved in dimethylformamide (15 ml), 60% sodium hydride (21.5 mg, 0.54 mmol) was added, stirred at room temperature for 15 minutes, and thereto methyl iodide (84.2 mg, 0.54 mmol) was added. The mixture was stirred at room temperature for 6 hours, concentrated under the reduced pressure to remove the solvent and purified by column chromatography to obtain the titled compound.

yield: 70.2%

EXAMPLE 95)

1-[(2-Methoxynaphth-3-yl)-N-ethylaminocarbonyl]-4-(3,5-dimethoxyphenyl)piperazine 1-[(2-Methoxynaphth-3-yl)aminocarbonyl]-4-(3,5-dimethoxyphenyl)piperazine was reacted by the same way with the example 94 to obtain the titled compound.

yield: 85.0%

EXAMPLE 96)

N-Hydroxy-N'-(5,6-dimethyl-2-methoxypyridin-3-yl)-(4-phenylpiperazin-1-yl)carboxyimidamide To methyl N-(5,6-dimethyl-2-methoxypyridin-3-yl)-(4-phenylpiperazin-1-yl)iminothiorate (0.50 g, 1.35 mmol) dissolved in chloroform (30 ml), hydroxylamine hydrochlroride (0.25 g, 3.60 mmol) and triethylamine (0.41 g, 4.05 mmol) were added and stirred at room temperature for 15 hours, and then thereto water (30 ml) was added to stop reaction. The resulting mixture was extracted with methylene chloride. The organic layer was concentrated under the reduced pressure to remove the solvent and purified by column chromatography to obtain the titled compound.

yield: 64.5% m.p.: 173~175° C.

EXAMPLE 97)

N-Hydroxy-N'-(5,6-dimethyl-2-methoxypyridin-3-yl)-[4-(4-methylphenyl)piperazin-1-yl]carboxyimidamide Methyl N-(5,6-dimethyl-2-methoxypyridin-3-yl)-[4-(4-methylphenyl)piperazin-1-yl]iminothiolate was reacted by the same way with the example 96 to obtain the titled compound.

yield: 55.2% m.p.: 187~189° C.

EXAMPLE 98)

N-Hydroxy-N'-(5,6-dimethyl-2-methoxypyridin-3-yl)-[4-(4-n-butylphenyl)piperazin-1-yl]carboxyimidamide Methyl N-(5,6-dimethyl-2-methoxypyridin-3-yl)-[4-(4-n-butylphenyl)-piperazin-1-yl]iminothiolate was reacted by the same way with the example 96 to obtain the titled compound.

yield: 60.1% m.p.: 153~155° C.

EXAMPLE 99)

N-Hydroxy-N'-(5,6-dimethyl-2-methoxypyridin-3-yl)-[4-(3,5-dimethylphenyl)piperazin-1-yl]carboxyimidamide Methyl N-(5,6-dimethyl-2-methoxypyridin-3-yl)-[4-(3,5-dimethylphenyl)-piperazin-1-yl]iminothiolate was reacted by the same way with the example 96 to obtain the titled compound.

yield: 67.5% m.p.: 125~128° C.

EXAMPLE 100)

N-Hydroxy-N'-(5,6-dimethyl-2-methoxypyridin-3-yl)-[4-(2-methoxyphenyl)piperazin-1-yl]carboxyimidamide Methyl N-(5,6-dimethyl-2-methoxypyridin-3-yl)-[4-(2-methoxyphenyl)-piperazin-1-yl]iminothiolate was reacted by the same way with the example 96 to obtain the titled compound.

yield: 62.0% m.p.: 134~136° C.

EXAMPLE 101)

N-Hydroxy-N'-(5,6-dimethyl-2-methoxypyridin-3-yl)-[4-(3,5-dimethoxyphenyl)piperazin-1-yl]carboxyimidamide Methyl N-(5,6-dimethyl-2-methoxypyridin-3-yl)-[4-(3,5-dimethoxyphenyl)piperazin-1-yl]iminothiolate was reacted by the same way with the example 96 to obtain the titled compound.

yield: 57.2% m.p.: 188~190° C.

EXAMPLE 102)

N-Hydroxy-N'-(5,6-dimethyl-2-methoxypyridin-3-yl)-[4-(3,5-difluorophenyl)piperazin-1-yl]carboxyimidamide Methyl N-(5,6-dimethyl-2-methoxypyridin-3-yl)-[4-(3,5-difluorophenyl)piperazin-1-yl]iminothiolate was reacted by the same way with the example 96 to obtain the titled compound.

yield: 60.7% m.p.: 177~178° C.

EXAMPLE 103)

N-Hydroxy-N'-(5,6-dimethyl-2-methoxypyridin-3-yl)-[4-(3,5-dichlorophenyl)piperazin-1-yl]carboxyimidamide Methyl N-(5,6-dimethyl-2-methoxypyridin-3-yl)-[4-(3,5-dichlorophenyl)piperazin-1-yl]iminothiolate was reacted by the same way with the example 96 to obtain the titled compound.

yield: 65.4% m.p.: 185~187° C.

EXAMPLE 104)

N-Hydroxy-N'-(5,6-dimethyl-2-methoxypyridin-3-yl)-[4-(3-bromophenyl)piperazin-1-yl]carboxyimidamide Methyl N-(5,6-dimethyl-2-methoxypyridin-3-yl)-[4-(3-bromophenyl)-piperazine-1-yl]iminothiolate was reacted by the same way with the example 96 to obtain the titled compound.

yield: 68.1% m.p.: 174~176° C.

EXAMPLE 105)

N-Hydroxy-N'-(5,6-dimethyl-2-methoxypyridin-3-yl)-[4-(3,5-dinitrophenyl)piperazin-1-yl]carboxyimidamide Methyl N-(5,6-dimethyl-2-methoxypyridin-3-yl)-[4-(3,5-dinitrophenyl)piperazin-1-yl]iminothiolate was reacted by the same way with the example 96 to obtain the titled compound.

yield: 45.2%
m.p.: 193~195° C.

EXAMPLE 106)

N-Hydroxy-N'-(5,6-dimethyl-2-methoxypyridin-3-yl)-[4-(3,5-diethylisophthal-1-yl)piperazin-1-yl]carboxyimidamide Methyl N-(5-methoxycarbonyl-2-methoxy-6-methylpyridin-3-yl)-[4-(3,5-diethylisophthal-1-yl)piperazin-1-yl]iminothiolate was reacted by the same way with the example 96 to obtain the titled compound.
yield: 64.1%
m.p.: 166~168° C.

EXAMPLE 107)

N-Hydroxy-N'-(5,6-dimethyl-2-methoxypyridin-3-yl)-{4-[3,5-bis-(hydroxymethyl)phenyl]piperazin-1-yl}carboxyimidamide To N-hydroxy-N'-(5,6-dimethyl-2-methoxypyridin-3-yl)-[(4-(3,5-diethylisophthal-1-yl)piperazin-1-yl]carboxyimidamide (500 mg, 1.0 mmol) dissolved in tetrahydrofuran (20 ml), lithium aluminium hydride (57 mg, 1.5 mmol) were added slowly, and stirred at 20° C. for 1 hours, and then thereto water (0.5 ml) was added to stop reaction. The resulting mixture was concentrated under the reduced pressure to remove the solvent and extracted with methylene chloride with addition of water. The organic layer was dried with magnesium sulfate and purified by column chromatography to obtain the titled compound.
yield: 42.1%
m.p.: 184~186° C.

EXAMPLE 108)

N-Hydroxy-N'-(5-ethyl-2-methoxy-6-methylpyridin-3-yl)-[4-(2-methoxyphenyl)piperazin-1-yl]carboxyimidamide Methyl N-(5-ethyl-2-methoxy-6-methylpyridin-3-yl)-[4-(2-methoxyphenyl)piperazin-1-yl]iminothiolate was reacted by the same way with the example 96 to obtain the titled compound.
yield: 69.4%
m.p.: 134~135° C.

EXAMPLE 109)

N-Hydroxy-N'-(5-ethyl-2-methoxy-6-methylpyridin-3-yl)-[4-(3,5-dimethoxyphenyl)piperazin-1-yl]carboxyimidamide Methyl N-(5-ethyl-2-methoxy-6-methylpyridin-3-yl)-[4-(3,5-dimethoxyphenyl)piperazin-1-yl]iminothiolate was reacted by the same way with the example 96 to obtain the titled compound.
yield: 68.2%
m.p.: 140~142° C.

EXAMPLE 110)

N-Hydroxy-N'-(5-ethyl-2-methoxy-6-methylpyridin-3-yl)-[4-(2-ethylphenyl)piperazin-1-yl]carboxyimidamide Methyl N-(5-ethyl-2-methoxy-6-methylpyridin-3-yl)-[4-(2-ethylphen-yl)-piperazin-1-yl]iminothiolate was reacted by the same way with the example 96 to obtain the titled compound.
yield: 70.2%
m.p.: 157~160° C.

EXAMPLE 111)

N-Hydroxy-N'-(5-ethyl-2-methoxy-6-methylpyridin-3-yl)-(4-phenylpiperazin-1-yl)carboxyimidamide Methyl N-(5-ethyl-2-methoxy-6-methylpyridin-3-yl)-(4-phenylpiperazin-1-yl)iminothiolate was reacted by the same way with the example 96 to obtain the titled compound.
yield: 72.2%
m.p.: 178~180° C.

EXAMPLE 112)

N-Hydroxy-N'-(5-ethyl-2-methoxy-6-methylpyridin-3-yl)-[4-(2-methylthiophenyl)piperazin-1-yl]carboxyimidamide Methyl N-(5-ethyl-2-methoxy-6-methylpyridin-3-yl)-[4-(2-methylthiophenyl)piperazin-1-yl]iminothiolate was reacted by the same way with the example 96 to obtain the titled compound.
yield: 69.3%
m.p.: 178~179° C.

EXAMPLE 113)

N-Hydroxy-N'-(5-ethyl-2-methoxy-6-methylpyridin-3-yl)-[4-(3,5-dimethylphenyl)piperazin-1-yl]carboxyimidamide Methyl N-(5-ethyl-2-methoxy-6-methylpyridin-3-yl)-[4-(3,5-dimethylphenyl)piperazin-1-yl]iminothiolate was reacted by the same way with the example 96 to obtain the titled compound.
yield: 64.7%
m.p.: 155~157° C.

EXAMPLE 114)

N-Hydroxy-N'-(5-ethyl-2-methoxy-6-methylpyridin-3-yl)-[4-(3,5-difluorophenyl)piperazin-1-yl]carboxyimidamide Methyl N-(5-ethyl-2-methoxy-6-methylpyridin-3-yl)-[4-(3,5-difluorophenyl)piperazin-1-yl]iminothiolate was reacted by the same way with the example 96 to obtain the titled compound.
yield: 51.8%
m.p.: 150~152° C.

EXAMPLE 115)

N-Hydroxy-N'-(5-ethyl-2-methoxy-6-methylpyridin-3-yl)-[4-(3,5-dichlorophenyl)piperazin-1-yl]carboxyimidamide Methyl N-(5-ethyl-2-methoxy-6-methylpyridin-3-yl)-[4-(3,5-dichlorophenyl)piperazin-1-yl]iminothiolate was reacted by the same way with the example 96 to obtain the titled compound.
yield: 72.2%
m.p.: 172~174° C.

EXAMPLE 116)

N-Hydroxy-N'-(5-ethyl-2-methoxy-6-methylpyridin-3-yl)-[4-(2-biphenyl)piperazin-1-yl]carboxyimidamide Methyl N-(5-ethyl-2-methoxy-6-methylpyridin-3-yl)-[4-(2-biphenyl)-piperazin-1-yl]iminothiolate was reacted by the same way with the example 96 to obtain the titled compound.

yield: 53.4%
m.p.: 195~197° C.

EXAMPLE 117)

N-Hydroxy-N'-(5-ethyl-2-methoxy-6-methylpyridin-3-yl)-[4-(3,5-dinitrophenyl)piperazin-1-yl]carboxyimidamide Methyl N-(5-ethyl-2-methoxy-6-methylpyridin-3-yl)-[4-(3,5-dinitrophenyl)piperazin-1-yl]iminothiolate was reacted by the same way with the example 96 to obtain the titled compound.
yield: 44.3%
m.p.: 193~195° C.

EXAMPLE 118)

N-Hydroxy-N'-(5-methoxycarbonyl-2-methoxy-6-methylpyridin-3-yl)-[4-(3,5-dimethoxyphenyl)piperazin-1-yl]carboxyimidamide Methyl N-(5-methoxycarbonyl-2-methoxy-6-methylpyridin-3-yl)-[4-(3,5-dimethoxyphenyl)piperazin-1-yl]iminothiolate was reacted by the same way with the example 96 to obtain the titled compound.
yield: 61.6%
m.p.: 192~194° C.

EXAMPLE 119)

N-Hydroxy-N'-(5-methoxycarbonyl-2-methoxy-6-methylpyridin-3-yl)-[4-(3,5-dimethylphenyl)piperazin-1-yl]carboxyimidamide Methyl N-(5-methoxycarbonyl-2-methoxy-6-methylpyridin-3-yl)-[4-(3,5-dimethylphenyl)piperazin-1-yl]iminothiolate was reacted by the same way with the example 96 to obtain the titled compound.
yield: 63.0%
m.p.: 195~197° C.

EXAMPLE 120)

N-Hydroxy-N'-(5-methoxycarbonyl-2-methoxy-6-methylpyridin-3-yl)-[4-(3,5-difluorophenyl)piperazin-1-yl]carboxyimidamide Methyl N-(5-methoxycarbonyl-2-methoxy-6-methylpyridin-3-yl)-[4-(3,5-difluorophenyl)piperazin-1-yl]iminothiolate was reacted by the same way with the example 96 to obtain the titled compound.
yield: 57.4%
m.p.: 170~172° C.

EXAMPLE 121)

N-Hydroxy-N'-(5-methoxycarbonyl-2-methoxy-6-methylpyridine-3-yl)-[4-(2-methoxyphenyl)piperazin-1-yl]carboxyimidamide Methyl N-(5-methoxycarbonyl-2-methoxy-6-methylpyridin-3-yl)-[4-(2-methoxyphenyl)piperazin-1-yl]iminothiolate was reacted by the same way with the example 96 to obtain the titled compound.
yield: 65.1%
m.p.: 176~178° C.

EXAMPLE 122)

N-Hydroxy-N'-(5-methoxycarbonyl-2-methoxy-6-methylpyridin-3-yl)-(4-phenylpiperazin-1-yl)carboxyimidamide Methyl N-(5-methoxycarbonyl-2-methoxy-6-methylpyridin-3-yl)-(4-phenylpiperazin-1-yl)iminothiolate was reacted by the same way with the example 96 to obtain the titled compound.
yield: 69.5%
m.p.: 194~196° C.

EXAMPLE 123)

N-Hydroxy-N'-(5-methoxycarbonyl-2-methoxy-6-methylpyridin-3-yl)-[4-(4-methylphenyl)piperazin-1-yl]carboxyimidamide Methyl N-(5-methoxycarbonyl-2-methoxy-6-methylpyridin-3-yl)-[4-(4-methylphenyl)piperazin-1-yl]iminothiolate was reacted by the same way with the example 96 to obtain the titled compound.
yield: 73.2%
m.p.: 190~192° C.

EXAMPLE 124)

N-Hydroxy-N'-(5-methoxycarbonyl-2-methoxy-6-methylpyridine-3-yl)-[4-(3-chlorophenyl)piperazin-1-yl]carboxyimidamide Methyl N-(5-methoxycarbonyl-2-methoxy-6-methylpyridin-3-yl)-[4-(3-chlorophenyl)piperazin-1-yl]iminothiolate was reacted by the same way with the example 96 to obtain the titled compound.
yield: 60.2%
m.p.: 91~93° C.

EXAMPLE 125)

N-Hydroxy-N'-(5-hydroxymethyl-2-methoxy-6-methylpyridin-3-yl)-[4-(3,5-dimethoxyphenyl)piperazin-1-yl]carboxyimidamide To N-hydroxy-N'-(5-methoxycarbonyl-2-methoxy-6-methylpyridin-3-yl)-[(4-(3,5-dimethoxyphenyl)piperazin-1-yl]carboxyimidamide (300 mg, 0.65 mmol) dissolved in tetrahydrofuran (20 ml), lithium aluminium hydride (37 mg, 0.98 mmol) was added slowly and stirred at 20° C. for 1 hours. Then, water (0.5 ml) was added thereto to stop reaction. The resulting mixture was concentrated under the reduced pressure to remove the solvent, and extracted with methylene chloride with addition of water. The organic layer was dried with magnesium sulfate, and purified by column chromatography to obtain the titled compound.
yield: 45.8%
m.p.: 185~187° C.

EXAMPLE 126)

N-Hydroxy-N'-(5-hydroxymethyl-2-methoxy-6-methylpyridine-3-yl)-[4-(3,5-dimethylphenyl)piperazin-1-yl]carboxyimidamide Methyl N-(5-hydroxymethyl-2-methoxy-6-methylpyridin-3-yl)-[4-(3,5-dimethylphenyl)piperazin-1-yl]iminothiolate was reacted by the same way with the example 125 to obtain the titled compound.
yield: 47.3%
m.p.: 127~129° C.

EXAMPLE 127)

N-Hydroxy-N'-(5-hydroxymethyl-2-methoxy-6-methylpyridin-3-yl)-[4-(3,5-difluorophenyl)piperazin-1-yl]carboxyimidamide Methyl N-(5-hydroxymethyl-2-methoxy-6-methylpyridin-3-yl)-[4-(3,5-difluorophenyl)piperazin-1-yl]

iminothiolate was reacted by the same way with the example 125 to obtain the titled compound.
yield: 42.3%
m.p.: 179~181° C.

EXAMPLE 128)

N-Hydroxy-N'-(5-hydroxymethyl-2-methoxy-6-methylpyridin-3-yl)-[4-(2-methoxyphenyl)piperazin-1-yl]carboxyimid-amide Methyl N-(5-hydroxymethyl-2-methoxy-6-methylpyridin-3-yl)-[4-(2-methoxyphenyl)piperazin-1-yl] iminothiolate was reacted by the same way with the example 125 to obtain the titled compound.
yield: 57.5%
m.p.: 129~131° C.

EXAMPLE 129)

N-Hydroxy-N'-(5-hydroxymethyl-2-methoxy-6-methylpyr-idine-3-yl)-(4-phenylpiperazin-1-yl)carboxyimidamide Methyl N-(5-hydroxymethyl-2-methoxy-6-methylpyridin-3-yl)-(4-phenylpiperazin-1-yl)iminothiolate was reacted by the same way with the example 125 to obtain the titled compound.
yield: 61.6%
m.p.: 167~169° C.

EXAMPLE 130)

N-Hydroxy-N'-(5-hydroxymethyl-2-methoxy-6-methylpyridin-3-yl)-[4-(4-methylphenyl)piperazin-1-yl]carboxyimidamide Methyl N-(5-hydroxymethyl-2-methoxy-6-methylpyridin-3-yl)-[4-(4-methylphenyl)piperazin-1-yl]iminothiolate was reacted by the same way with the example 125 to obtain the titled compound.
yield: 66.7%
m.p.: 157~159° C.

EXAMPLE 131)

N-Hydroxy-N'-(5-hydroxymethyl-2-methoxy-6-methylpyridin-3-yl)-[4-(3-chlorophenyl)piperazin-1-yl]carboxyimidamide Methyl N-(5-hydroxymethyl-2-methoxy-6-methylpyridin-3-yl)-[4-(3-chlorophenyl)piperazin-1-yl] iminothiolate was reacted by the same way with the example 125 to obtain the titled compound.
yield: 56.2%
m.p.: 171~173° C.

EXAMPLE 132)

N-Hydroxy-N'-(5-acetyl-2-methoxy-6-methylpyridin-3-yl)-[4-(3,5-dimethylphenyl)piperazin-1-yl]carboxyimidamide Methyl N-(5-acetyl-2-methoxy-6-methylpyridin-3-yl)-[4-(3,5-dimethylphenyl)piperazin-1-yl]iminothiolate was reacted by the same way with the example 96 to obtain the titled compound.
yield: 35.1%
m.p.: 174~176° C.

EXAMPLE 133)

N-Hydroxy-N'-(5-acetyl-2-methoxy-6-methylpyridin-3-yl)-[4-(3,5-dimethoxyphenyl)piperazin-1-yl]carboxyimidamide Methyl N-(5-acetyl-2-methoxy-6-methylpyridin-3-yl)-[4-(3,5-dimethoxyphenyl)piperazin-1-yl]iminothiolate way with the example 96 to obtain the titled compound.
yield: 32.4%
m.p.: 143~145° C.

EXAMPLE 134)

N-Hydroxy-N'-(5-acetyl-2-methoxy-6-methylpyridin-3-yl)-(4-phenylpiperazin-1-yl)carboxyimidamide Methyl N-(5-acetyl-2-methoxy-6-methylpyridin-3-yl)-(4-phenylpiperazin-1-yl)iminothiolate was reacted by the same way with the example 96 to obtain the titled compound.
yield: 40.5%
m.p.: 169~170° C.

EXAMPLE 135)

N-Hydroxy-N'-(5-acetyl-2-methoxy-6-methylpyridin-3-yl)-[4-(4-methylphenyl)piperazin-1-yl]carboxyimidamide Methyl N-(5-acetyl-2-methoxy-6-methylpyridin-3-yl)-[4-(4-methylphenyl)piperazin-1-yl]iminothiolate was reacted by the same way with the example 96 to obtain the titled compound.
yield: 55.2%
m.p.: 164~166° C.

EXAMPLE 136)

N-Hydroxy-N'-(5-acetyl-2-methoxy-6-methylpyridin-3-yl)-[4-(3,5-difluorophenyl)piperazin-1-yl]carboxyimidamide Methyl N-(5-acetyl-2-methoxy-6-methylpyridin-3-yl)-[4-(3,5-difluorophenyl)piperazin-1-yl]iminothiolate was reacted by the same way with the example 96 to obtain the titled compound.
yield: 33.2%
m.p.: 184~185° C.

EXAMPLE 137)

N-Hydroxy-N'-(5-acetyl-2-methoxy-6-methylpyridin-3-yl)-[4-(2-methylthiophenyl)piperazin-1-yl]carboxyimidamide Methyl N-(5-acetyl-2-methoxy-6-methylpyridin-3-yl)-[4-(2-methylthiophenyl)piperazin-1-yl]iminothiolate was reacted by the same way with the example 96 to obtain the titled compound.
yield: 39.8%
m.p.: 178~179° C.

EXAMPLE 138)

N-Hydroxy-N'-[5-(1-hydroxyethyl)-2-methoxy-6-methylpyridin-3-yl]-[4-(3,5-dimethylphenyl)piperazin-1-yl]carboxyimidamide To N-hydroxy-N'-(5-acetyl-2-methoxy-6-methylpyridin-3-yl)-[(4-(3,5-dimethylphenyl)piperazin-1-yl] carboxyimidamide (150 mg, 0.36 mmol), ethanol (20 ml) and then sodium borohydride (17 mg, 0.45 mmol) were added slowly. The resulting mixture was stirred at 20° C. for 4 hours, concentrated under the reduced pressure to remove the solvent, and extracted with methylene chloride with addition of water. The organic layer was dried with magnesium sulfate and purified by column chromatography to obtain the titled compound.

yield: 75.6%
m.p.: 94~96° C.

EXAMPLE 139)

N-Hydroxy-N'-[5-(1-hydroxyethyl)-2-methoxy-6-methylpyridin-3-yl]-[4-(3,5-dimethoxyphenyl)piperazin-1-yl]carboxyimidamide Methyl N-[5-(1-hydroxyethyl)-2-methoxy-6-methylpyridin-3-yl]-[4-(3,5-dimethoxyphenyl)piperazin-1-yl]iminothiolate was reacted by the same way with the example 138 to obtain the titled compound.
yield: 65.6%
m.p.: 123~125° C.

EXAMPLE 140)

N-Hydroxy-N'-[5-(1-hydroxyethyl)-2-methoxy-6-methylpyridin-3-yl]-(4-phenylpiperazin-1-yl)carboxyimidamide Methyl N-[5-(1-hydroxyethyl)-2-methoxy-6-methylpyridin-3-yl]-(4-phenylpiperazin-1-yl)iminothiolate was reacted by the same way with the example 138 to obtain the titled compound.
yield: 72.3%
m.p.: 154~155° C.

EXAMPLE 141)

N-Hydroxy-N'-[5-(1-hydroxyethyl)-2-methoxy-6-methylpyridin-3-yl]-[4-(4-methylphenyl)piperazin-1-yl]carboxyimidamide Methyl N-[5-(1-hydroxyethyl)-2-methoxy-6-methylpyridin-3-yl]-[4-(4-methylphenyl)piperazin-1-yl]iminothiolate was reacted by the same way with the example 138 to obtain the titled compound.
yield: 62.1%
m.p.: 187~189° C.

EXAMPLE 142)

N-Hydroxy-N'-[5-(1-hydroxyethyl)-2-methoxy-6-methylpyridin-3-yl]-[4-(3,5-difluorophenyl)piperazin-1-yl]carboxyimidamide Methyl N-[5-(1-hydroxyethyl)-2-methoxy-6-methylpyridin-3-yl]-[4-(3,5-difluorophenyl)piperazin-1-yl]iminothiolate was reacted by the same way with the example 138 to obtain the titled compound.
yield: 63.8%
m.p.: 156~157° C.

EXAMPLE 143)

N-Hydroxy-N'-[5-(1-hydroxyethyl)-2-methoxy-6-methylpyridin-3-yl]-[4-(2-methylthiophenyl)piperazin-1-yl]carboxyimidamide Methyl N-[5-(1-hydroxyethyl)-2-methoxy-6-methylpyridin-3-yl]-[4-(2-methylthiophenyl)piperazin-1-yl]iminothiolate was reacted by the same way with the example 138 to obtain the titled compound.
yield: 70.2%
m.p.: 162~163° C.

EXAMPLE 144)

N-Hydroxy-N'-[5-(1-hydroxyiminoethyl)-2-methoxy-6-methylpyridin-3-yl]-[4-(3,5-dimethylphenyl)piperazin-1-yl]carboxyimidamide Methyl N-(5-acetyl-2-methoxy-6-methylpyridin-3-yl)-[4-(3,5-dimethylphenyl)piperazin-1-yl]iminothiolate was reacted by the same way with the example 96 to obtain the titled compound.
yield: 23.2%

EXAMPLE 145)

N-Hydroxy-N'-[5-(1-hydroxyiminoethyl)-2-methoxy-6-methylpyridin-3-yl]-[4-(3,5-dimethoxyphenyl)piperazin-1-yl]carboxyimidamide Methyl N-(5-acetyl-2-methoxy-6-methylpyridin-3-yl)-[4-(3,5-dimethoxyphenyl)piperazin-1-yl]iminothiolate was reacted by the same way with the example 96 to obtain the titled compound.
yield: 35.6%

EXAMPLE 146)

N-Hydroxy-N'-[5-(1-hydroxyiminoethyl)-2-methoxy-6-methylpyridin-3-yl]-[4-(3,5-difluorophenyl)piperazin-1-yl]carboxyimidamide Methyl N-(5-acetyl-2-methoxy-6-methylpyridin-3-yl)-[4-(3,5-difluorophenyl)piperazin-1-yl]iminothiolate was reacted by the same way with the example 96 to obtain the titled compound.
yield: 33.3%

EXAMPLE 147)

N-Hydroxy-N'-[5-(1-hydroxyiminoethyl)-2-methoxy-6-methylpyridin-3-yl]-[4-(2-methylthiophenyl)piperzin-1-yl]carboxyimidamide Methyl N-(5-acetyl-2-methoxy-6-methylpyridin-3-yl)-[4-(2-methylthiophenyl)piperazin-1-yl]iminothiolate was reacted by the same way with the example 96 to obtain the titled compound.
yield: 30.2%

EXAMPLE 148)

N-Hydroxy-N'-[5-(1-hydroxyiminoethyl)-2-methoxy-6-methylpyridin-3-yl]-[4-(3,5-dinitrophenyl)piperazin-1-yl]carboxyimidamide Methyl N-(5-acetyl-2-methoxy-6-methylpyridin-3-yl)-[4-(3,5-dinitrophenyl)piperazin-1-yl]iminothiolate was reacted by the same way with the example 96 to obtain the titled compound.
yield: 29.5%

EXAMPLE 149)

N-Hydroxy-N'-[5-(1-hydroxyiminoethyl)-2-methoxy-6-me-thylpyridin-3-yl]-[4-(4-methylphenyl)piperazin-1-yl]carboxyimidamide Methyl N-(5-acetyl-2-methoxy-6-methylpyridin-3-yl)-[4-(4-methylphenyl)piperazin-1-yl]iminothiolate was reacted by the same way with the example 96 to obtain the titled compound.
yield: 25.0%

EXAMPLE 150)

N-Hydroxy-N'-[5-(1-aminoethyl)-2-methoxy-6-methylpyridin-3-yl]-[4-(3,5-dimethylphenyl)piperazin-1-yl]carboxyimidamide Methyl N-[5-(1-aminoethyl)-2-methoxy-6-methylpyridin-3-yl]-[4-(3,5-dimethylphenyl)piperazin-1-yl]

iminothiolate was reacted by the same way with the example 96 to obtain the titled compound.

yield: 45.6%

EXAMPLE 151)

N-Hydroxy-N'-[5-(1-aminoethyl)-2-methoxy-6-methylpyridin-3-yl]-[4-(3,5-dimethoxyphenyl)piperazin-1-yl]carboxyimidamide Methyl N-[5-(1-aminoethyl)-2-methoxy-6-methylpyridin-3-yl]-[4-(3,5-dimethoxyphenyl)piperazin-1-yl]iminothiolate was reacted by the same way with the example 96 to obtain the titled compound.

yield: 42.2%

EXAMPLE 152)

N-Hydroxy-N'-[5-(1-aminoethyl)-2-methoxy-6-methylpyridin-3-yl]-[4-(3,5-difluorophenyl)piperazin-1-yl]carboxyimidamide Methyl N-[5-(1-aminoethyl)-2-methoxy-6-methylpyridin-3-yl]-[4-(3,5-difluorophenyl)piperazin-1-yl]iminothiolate was reacted by the same way with the example 96 to obtain the titled compound.

yield: 53.1%

EXAMPLE 153)

N-Hydroxy-N'-[5-(1-aminoethyl)-2-methoxy-6-methylpyridin-3-yl]-[4-(2-methylthiophenyl)piperazin-1-yl]carboxyimidamide Methyl N-[5-(1-aminoethyl)-2-methoxy-6-methylpyridin-3-yl]-[4-(2-methylthiophenyl)piperazin-1-yl]iminothiolate was reacted by the same way with the example 96 to obtain the titled compound.

yield: 44.7%

EXAMPLE 154)

N-Hydroxy-N'-[5-(1-aminoethyl)-2-methoxy-6-methylpyridin-3-yl]-[4-(3,5-dinitrophenyl)piperazin-1-yl]carboxyimidamide Methyl N-[5-(1-aminoethyl)-2-methoxy-6-methylpyridin-3-yl]-[4-(3,5-dinitrophenyl)piperazin-1-yl] iminothiolate was reacted by the same way with the example 96 to obtain the titled compound.

yield: 52.1%

EXAMPLE 155)

N-Hydroxy-N'-[5-(1-aminoethyl)-2-methoxy-6-methylpyridin-3-yl]-[4-(3,5-chlorophenyl)piperazin-1-yl]carboxyimidamide Methyl N-[5-(1-aminoethyl)-2-methoxy-6-methylpyridin-3-yl]-[4-(3,5-chlorophenyl)piperazin-1-yl] iminothiolate was reacted by the same way with the example 96 to obtain the titled compound.

yield: 47.6%

EXAMPLE 156)

N-Hydroxy-N'-(6-ethyl-5-methoxycarbonyl-2-methoxypyridin-3-yl)-[4-(4-methylphenyl)piperazin-1-yl]carboxyimidamide Methyl N-(6-ethyl-5-methoxycarbonyl-2-methoxypyridin-3-yl)-[4-(4-methylphenyl)piperazin-1-yl] iminothiolate was reacted by the same way with the example 96 to obtain the titled compound.

yield: 71.2% m.p.: 176~178° C.

EXAMPLE 157)

N-Hydroxy-N'-(6-ethyl-5-methoxycarbonyl-2-methoxypyridin-3-yl)-[4-(2-ethylphenyl)piperazin-1-yl]carboxyimidamide Methyl N-(6-ethyl-5-methoxycarbonyl-2-methoxypyridin-3-yl)-[4-(2-ethylphenyl)piperazin-1-yl] iminothiolate was reacted by the same way with the example 96 to obtain the titled compound.

yield: 65.0% m.p.: 182~184° C.

EXAMPLE 158)

N-Hydroxy-N'-(6-ethyl-5-methoxycarbonyl-2-methoxypyridin-3-yl)-[4-(3,5-dimethylphenyl)piperazin-1-yl]carboxyimidamide Methyl N-(6-ethyl-5-methoxycarbonyl-2-methoxypyridin-3-yl)-[4-(3,5-dimethylphenyl)piperazin-1-yl]iminothiolate was reacted by the same way with the example 96 to obtain the titled compound.

yield: 59.1% m.p.: 152~155° C.

EXAMPLE 159)

N-Hydroxy-N'-(6-ethyl-5-methoxycarbonyl-2-methoxypyridin-3-yl)-[4-(3,5-dimethoxyphenyl)piperazin-1-yl]carboxyimidamide Methyl N-(6-ethyl-5-methoxycarbonyl-2-methoxypyridin-3-yl)-[4-(3,5-dimethoxyphenyl)piperazin-1-yl]iminothiolate was reacted by the same way with the example 96 to obtain the titled compound.

yield: 55.6% m.p.: 156~157° C.

EXAMPLE 160)

N-Hydroxy-N'-(6-ethyl-5-methoxycarbonyl-2-methoxypyridin-3-yl)-[4-(3,5-dichlorophenyl)piperazin-1-yl]carboxyimidamide Methyl N-(6-ethyl-5-methoxycarbonyl-2-methoxypyridin-3-yl)-[4-(3,5-dichlorophenyl)piperazin-1-yl]iminothiolate was reacted by the same way with the example 96 to obtain the titled compound.

yield: 54.4% m.p.: 158~160° C.

EXAMPLE 161)

N-Hydroxy-N'-(6-ethyl-5-methoxycarbonyl-2-methoxypyridin-3-yl)-[4-(2-methylthiophenyl)piperazin-1-yl]carboxyimidamide Methyl N-(6-ethyl-5-methoxycarbonyl-2-methoxypyridin-3-yl)-[4-(2-methylthiophenyl)piperazin-1-yl]iminothiolate was reacted by the same way with the example 96 to obtain the titled compound.

yield: 50.1% m.p.: 168~170° C.

EXAMPLE 162)

N-Hydroxy-N'-(6-ethyl-5-methoxycarbonyl-2-methoxypyridin-3-yl)-[4-(3,5-diethylisophthalate-1-yl)piperazin-1-yl]carboxyimidamide Methyl N-(6-ethyl-5-methoxycarbonyl-2-methoxypyridin -3-yl)-[4-(3,5-diethylisophthal-1-yl)

piperazin-1-yl]iminothiolate was reacted by the same way with the example 96 to obtain the titled compound.

yield: 57.3% m.p.: 101~103° C.

EXAMPLE 163)

N-Hydroxy-N'-(6-ethyl-5-methoxycarbonyl-2-methoxypyridin-3-yl)-[4-(3,5-difluorophenyl)piperazin-1-yl]carboxyimidamide Methyl N-(6-ethyl-5-methoxycarbonyl-2-methoxypyridin-3-yl)-[4-(3,5-difluorophenyl)piperazin-1-yl]iminothiolate was reacted by the same way with the example 96 to obtain the titled compound.

yield: 45.0% m.p.: 143~145° C.

EXAMPLE 164)

N-Hydroxy-N'-(6-ethyl-5-hydroxymethyl-2-methoxypyridin-3-yl)-[4-(4-methylphenyl)piperazin-1-yl]carboxyimidamide Methyl N-(6-ethyl-5-hydroxymethyl-2-methoxypyridin-3-yl)-[4-(4-methylphenyl)piperazin-1-yl]iminothiolate was reacted by the same way with the example 125 to obtain the titled compound.

yield: 66.6% m.p.: 170~172° C.

EXAMPLE 165)

N-Hydroxy-N'-(6-ethyl-5-hydroxymethyl-2-methoxypyridin -3-yl)-[4-(2-ethylphenyl)piperazin-1-yl]carboxyimidamide Methyl N-(5-ethyl-2-methoxy-6-methylpyridin-3-yl)-[4-(2-ethylphenyl)piperazin-1-yl]iminothiolate was reacted by the same way with the example 125 to obtain the titled compound.

yield: 60.4% m.p.: 185~187° C.

EXAMPLE 166)

N-Hydroxy-N'-(6-ethyl-5-hydroxymethyl-2-methoxypyridin-3-yl)-[4-(3,5-dimethylphenyl)piperazin-1-yl]carboxyimidamide Methyl N-(6-ethyl-5-hydroxymethyl-2-methoxypyridin-3-yl)-[4-(3,5-dimethylphenyl)piperazin-1-yl]iminothiolate was reacted by the same way with the example 125 to obtain the titled compound.

yield: 65.1% m.p.: 75~77° C.

EXAMPLE 167)

N-Hydroxy-N'-(6-ethyl-5-hydroxymethyl-2-methoxypyridin-3-yl)-[4-(3,5-dimethoxyphenyl)piperazin-1-yl]carboxyimidamide Methyl N-(6-ethyl-5-hydroxymethyl-2-methoxypyridin-3-yl)-[4-(3,5-dimethoxyphenyl)piperazin-1-yl]iminothiolate was reacted by the same way with the example 125 to obtain the titled compound.

yield: 61.2% m.p.: 67~69° C.

EXAMPLE 168)

N-Hydroxy-N'-(6-ethyl-5-hydroxymethyl-2-methoxypyridin-3-yl)-[4-(3,5-dichlorophenyl)piperazin-1-yl]carboxyimidamide Methyl N-(6-ethyl-5-hydroxymethyl-2-methoxypyridin-3-yl)-[4-(3,5-dichlorophenyl)piperazin-1-yl]iminothiolate was reacted by the same way with the example 125 to obtain the titled compound.

yield: 70.1% m.p.: 75~77° C.

EXAMPLE 169)

N-Hydroxy-N'-(6-ethyl-5-hydroxymethyl-2-methoxypyridin-3-yl)-[4-(2-methylthiophenyl)piperazin-1-yl]carboxyimidamide Methyl N-(6-ethyl-5-hydroxymethyl-2-methoxypyridin-3-yl)-[4-(2-methylthiophenyl)piperazin-1-yl]iminothiolate was reacted by the same way with the example 125 to obtain the titled compound.

yield: 67.2% m.p.: 163~165° C.

EXAMPLE 170)

N-Hydroxy-N'-(6-ethyl-5-hydroxymethyl-2-methoxypyridin-3-yl)-{4-[3,5-bis(hydroxymethyl)phenyl]piperazin-1-yl}carboxyimidamide Methyl N-(6-ethyl-5-hydroxymethyl-2-methoxypyridin-3-yl)-{4-[3,5-bis(hydroxymethyl)phenyl]piperazin-1-yl}iminothiolate was reacted by the same way with the example 125 to obtain the titled compound yield: 59.4%

EXAMPLE 171)

N-Hydroxy-N'-(6-ethyl-5-hydroxymethyl-2-methoxypyridin-3-yl)-[4-(3,5-difluorophenyl)piperazin-1-yl]carboxyimidamide Methyl N-(6-ethyl-5-hydroxymethyl-2-methoxypyridin-3-yl)-[4-(3,5-difluorophenyl)piperazin-1-yl]iminothiolate was reacted by the same way with the example 125 to obtain the titled compound.

yield: 48.7% m.p.: 68~70° C.

EXAMPLE 172)

N-Hydroxy-N'-(2-methoxyquinolin-3-yl)-[4-(3,5-dimethoxyphenyl)-piperazin-1-yl]carboxyimidamide Methyl N-(2-methoxyquinolin-3-yl)-[4-(3,5-dimethoxyphenyl)-piperazin-1-yl]iminothiolate was reacted by the same way with the example 96 to obtain the titled compound.

yield: 41.0% m.p.: 215~217° C.

EXAMPLE 173)

N-Hydroxy-N'-(2-methoxyquinolin-3-yl)-[4-(3,5-dimethylphenyl)-piperazin-1-yl]carboxyimidamide Methyl N-(2-methoxyquinolin-3-yl)-[4-(3,5-dimethylphenyl)-piperazin-1-yl]iminothiolate was reacted by the same way with the example 96 to obtain the titled compound.

yield: 44.2%
m.p.: 182~184° C.

EXAMPLE 174)

N-Hydroxy-N'-(2-methoxyquinolin-3-yl)-[4-(3,5-difluoro-phenyl)-piperazin-1-yl]carboxyimidamide Methyl N-(2-methoxyquinolin-3-yl)-[4-(3,5-difluorophenyl)-piperazin-1-yl]iminothiolate was reacted by the same way with the example 96 to obtain the titled compound.
yield: 38.1%
m.p.: 163~165° C.

EXAMPLE 175)

N-Hydroxy-N'-(2-methoxyquinolin-3-yl)-[4-(2-methoxyphenyl)-piperazin-1-yl]carboxyimidamide Methyl N-(2-methoxyquinolin-3-yl)-[4-(2-methoxyphenyl)-piperazin-1-yl]iminothiolate was reacted by the same way with the example 96 to obtain the titled compound.
yield: 43.2%
m.p.: 210~212° C.

EXAMPLE 176)

N-Hydroxy-N'-(2-methoxyquinolin-3-yl)-[4-(3-chlorophenyl)-piperazin-1-yl]carboxyimidamide Methyl N-(2-methoxyquinolin-3-yl)-[4-(3-chlorophenyl)piperazin-1-yl]iminothiolate was reacted by the same way with the example 96 to obtain the titled compound.
yield: 45.2%
m.p.: 162~164° C.

EXAMPLE 177)

N-Hydroxy-N'-(4,5-dimethyl-2-methoxyphenyl-1-yl)-(4-phenylpiperazin-1-yl)carboxyimidamide Methyl N-(4,5-dimethyl-2-methoxyphenyl-1-yl)-(4-phenylpiperazin-1-yl)iminothiolate was reacted by the same way with the example 96 to obtain the titled compound.
yield: 62.7%
m.p.: 160~162° C.

EXAMPLE 178)

N-Hydroxy-N'-(4,5-dimethyl-2-methoxyphenyl-1-yl)-[4-(4-methylphenyl)piperazin-1-yl]carboxyimidamide Methyl N-(4,5-dimethyl-2-methoxyphenyl-1-yl)-[4-(4-methylphenyl)-piperazin-1-yl]iminothiolate was reacted by the same way with the example 96 to obtain the titled compound.
yield: 60.1%
m.p.: 181~183° C.

EXAMPLE 179)

N-Hydroxy-N'-(4,5-dimethyl-2-methoxyphenyl-1-yl)-[4-(2-ethylphenyl)piperazin-1-yl] carboxyimidamide Methyl N-(4,5-dimethyl-2-methoxyphenyl-1-yl)-[4-(2-ethylphenyl)-piperazin-1-yl]iminothiolate was reacted by the same way with the example 96 to obtain the titled compound.
yield: 65.4%
m.p.: 194~196° C.

EXAMPLE 180)

N-Hydroxy-N'-(4,5-dimethyl-2-methoxyphenyl-1-yl)-[4-(3,5-dimethylphenyl)piperazin-1-yl] carboxyimidamide Methyl N-(4,5-dimethyl-2-methoxyphenyl-1-yl)-[4-(3,5-dimethylphenyl)-piperazin-1-yl]iminothiolate was reacted by the same way with the example 96 to obtain the titled compound.
yield: 64.1%
m.p.: 184~186° C.

EXAMPLE 181)

N-Hydroxy-N'-(4,5-dimethyl-2-methoxyphenyl-1-yl)-[4-(3,5-dimethoxyphenyl)piperazin-1-yl] carboxyimidamide Methyl N-(4,5-dimethyl-2-methoxyphenyl-1-yl)-[4-(3,5-dimethoxyphenyl)piperazin-1-yl]iminothiolate was reacted by the same way with the example 96 to obtain the titled compound.
yield: 65.5%
m.p.: 189~191° C.

EXAMPLE 182)

N-Hydroxy-N'-(4,5-dimethyl-2-methoxyphenyl-1-yl)-[4-(3,5-difluorophenyl)piperazin-1-yl] carboxyimidamide Methyl N-(4,5-dimethyl-2-methoxyphenyl-1-yl)-[4-(3,5-difluorophenyl)-piperazin-1-yl]imninothiolate was reacted by the same way with the example 96 to obtain the titled compound.
yield: 60.0%
m.p.: 179~181° C.

EXAMPLE 183)

N-Hydroxy-N'-(4,5-dimethyl-2-methoxyphenyl-1-yl)-[4-(3-chlorophenyl)piperazin-1-yl] carboxyimidamide Methyl N-(4,5-dimethyl-2-methoxyphenyl-1-yl)-[4-(3-chlorophenyl)-piperazin-1-yl]iminothiolate was reacted by the same way with the example 96 to obtain the titled compound.
yield: 58.7%
m.p.: 174~176° C.

EXAMPLE 184)

N-Hydroxy-N'-(4,5-dimethyl-2-methoxyphenyl-1-yl)-[4-(3-bromophenyl)piperazin-1-yl] carboxyimidamide Methyl N-(4,5-dimethyl-2-methoxyphenyl-1-yl)-[4-(3-bromophenyl)-piperazin-1-yl]iminothiolate was reacted by the same way with the example 96 to obtain the titled compound.
yield: 61.2%
m.p.: 178~180° C.

EXAMPLE 185)

N-Hydroxy-N'-(4,5-dimethyl-2-methoxyphenyl-1-yl)-[4-(2-methylthiophenyl)piperazin-1-yl] carboxyimidamide Methyl N-(4,5-dimethyl-2-methoxyphenyl-1-yl)-[4-(2-methylthiophenyl)piperazin-1-yl]iminothiolate was reacted by the same way with the example 96 to obtain the titled compound.

yield: 60.5%
m.p.: 194~196° C.

EXAMPLE 186)

N-Methoxy-N'-(5,6-dimethyl-2-methoxypyridin-3-yl)-(4-phenylpiperazin-1-yl)carboxyimidamide To N-hydroxy-N'-(5,6-dimethyl-2-methoxypyridin-3-yl)-(4-phenylpiperazin-1-yl)carboxyimidamide (0.5 g, 1.41 mmol) dissolved in dimethylformamide (15 ml), sodium hydride (60%, 57.8 mg, 1.45 mmol) and methyl iodide (0.20 g, 1.41 mmol) were added and stirred for 4 hours and then water (20 ml) was added thereto to stop reaction. The resulting mixture was extracted with ethylether. The organic layer was concentrated under the reduced pressure to remove the solvent and purified by column chromatography to obtain the titled compound.
yield: 89.1%

EXAMPLE 187)

N-Methoxy-N'-(5,6-dimethyl-2-methoxypyridin-3-yl)-[4-(4-methylphenyl)piperazin-1-yl]carboxyimidamide N-Hydroxy-N'-(5,6-dimethyl-2-methoxypyridin-3-yl)-[4-(4-methylphenyl)piperazin-1-yl]carboxyimidamide was reacted by the same way with the example 186 to obtain the titled compound.
yield: 92.2%

EXAMPLE 188)

N-Methoxy-N'-(5,6-dimethyl-2-methoxypyridin-3-yl)-[4-(3,5-dimethylphenyl)piperazin-1-yl]carboxyimidamide N-Hydroxy-N'-(5,6-dimethyl-2-methoxypyridin-3-yl)-[4-(3,5-dimethylphenyl)piperazin-1-yl]carboxyimidamide was reacted by the same way with the example 186 to obtain the titled compound.
yield: 90.0%

EXAMPLE 189)

N-Methoxy-N'-(5,6-dimethyl-2-methoxypyridin-3-yl)-[4-(3,5-dimethoxyphenyl)piperazin-1-yl]carboxyimidamide N-Hydroxy-N'-(5,6-dimethyl-2-methoxypyridin-3-yl)-[4-(3,5-dimethoxyphenyl)piperazin-1-yl]carboxyimidamide same way with the example 186 to obtain the titled compound.
yield: 92.2%

EXAMPLE 190)

N-Methoxy-N'-(5,6-dimethyl-2-methoxypyridin-3-yl)-[4-(3,5-difluorophenyl)piperazin-1-yl]carboxyimidamide N-Hydroxy-N'-(5,6-dimethyl-2-methoxypyridin-3-yl)-[4-(3,5-difluorophenyl)piperazin-1-yl]carboxyimidamide was reacted by the same way with the example 186 to obtain the titled compound.
yield: 85.2%

EXAMPLE 191)

N-Methoxy-N'-(5,6-dimethyl-2-methoxypyridin-3-yl)-[4-(2-methylthiophenyl)piperazin-1-yl]carboxyimidamide N-Hydroxy-N'-(5,6-dimethyl-2-methoxypyridin-3-yl)-[4-(2-methylthiophenyl)piperazin-1-yl]carboxyimidamide was reacted by the same way with the example 186 to obtain the titled compound.
yield: 89.2%

EXAMPLE 192)

N-Methoxy-N'-(5,6-dimethyl-2-methoxypyridin-3-yl)-[4-(3,5-dinitrophenyl)piperazin-1-yl]carboxyimidamide N-Hydroxy-N'-(5,6-dimethyl-2-methoxypyridin-3-yl)-[4-(3,5-dinitrophenyl)piperazin-1-yl]carboxyimidamide was reacted by the same way with the example 186 to obtain the titled compound.
yield: 79.5%

EXAMPLE 193)

N-Methoxy-N'-(5-ethyl-6-methyl-2-methoxypyridin-3-yl)-[4-(3,5-dichlorophenyl)piperazin-1-yl]carboxyimidamide N-Hydroxy-N'-(5-ethyl-6-methyl-2-methoxypyridin-3-yl)-[4-(3,5-dichlorophenyl)piperazin-1-yl]carboxyimidamide was reacted by the same way with the example 186 to obtain the titled compound.
yield: 84.2%
m.p.: 163~165° C.

EXAMPLE 194)

N-Methoxy-N'-(6-ethyl-5-methoxycarbonyl-2-methoxypyridin-3-yl)-[4-(3,5-difluorophenyl)piperazin-1-yl]carboxyimidamide N-Hydroxy-N'-(6-ethyl-5-methoxycarbonyl-2-methoxypyridin-3-yl)-[4-(3,5-difluorophenyl)piperazin-1-yl]carboxyimid-amide was reacted by the same way with the example 186 to obtain the titled compound.
yield: 91.3%

EXAMPLE 195)

N-Methoxy-N'-(6-ethyl-5-methoxycarbonyl-2-methoxypyridin-3-yl)-[4-(3,5-diethylisophthal-1-yl)piperazin-1-yl]carboxyimidamide N-Hydroxy-N'-(6-ethyl-5-methoxycarbonyl-2-methoxypyridin-3-yl)-[4-(3,5-diethylisophthal-1-yl)piperazin-1-yl]carboxyimidamide was reacted by the same way with the example 186 to obtain the titled compound.
yield: 94.0%

EXAMPLE 196)

N-Methoxy-N'-(6-ethyl-5-hydroxymethyl-2-methoxypyridin-3-yl)-{4-[3,5-bis(hydroxymethyl)phenyl-1-yl]piperzain-1-yl}carboxyimidamide N-methoxy-N'-(6-ethyl-5-methoxycarbonyl-2-methoxypyridin-3-yl)-[4-(3,5-diethylisophthal-1-yl)piperazin-1-yl]carboxyimidamide was reacted by the same way with the example 186 to obtain the titled compound.
yield: 68.0%

EXAMPLE 197)

N-Methoxy-N'-(4,5-dimethyl-2-methoxyphenyl-1-yl)-[4-(4-methylphenyl)piperazin-1-yl]carboxyimidamide N-Hydroxy-N'-(4,5-dimethyl-2-methoxyphenyl-1-yl)-[4-(4-methylphenyl)piperazin-1-yl]carboxyimidamide was reacted by the same way with the example 186 to obtain the titled compound.

yield: 86.7%

EXAMPLE 198)

N-Methoxy-N'-(4,5-dimethyl-2-methoxyphenyl-1-yl)-[4-(3,5-dimethylphenyl)piperazin-1-yl]carboxyimidamide N-Hydroxy-N'-(4,5-dimethyl-2-methoxyphenyl-1-yl)-[4-(3,5-dimethylphenyl)piperazin-1-yl]carboxyimidamide was reacted by the same way with the example 186 to obtain the titled compound.

yield: 87.0%

EXAMPLE 199)

Methyl N-(5,6-dimethyl-2-methoxypyridin-3-yl)-(4-phenylpiperazin-1-yl)-iminothiolate To 1-[(5,6-dimethyl-2-methoxypyridin-3-yl)aminocarbonyl]-4-phenylpiperazine (0.5 g, 1.40 mmol) dissolved in dimethylformamide(15 ml), sodium hydride (60%, 56.1 mg, 1.40 mmol) and methyl iodide (0.20 g, 1.41 mmol) were added. The resulting mixture was stirred for 2 hours and then water (20 ml) was added thereto to stop reaction. The resulting mixture was purified by column chromatography to obtain the titled compound.

yield: 92.4%

EXAMPLE 200)

Methyl N-(5,6-dimethyl-2-methoxypyridin-3-yl)-[4-(4-et-hylphenyl)piperazin-1-yl]iminothiolate 1-[(5,6-Dimethyl-2-methoxypyridin-3-yl)aminothiocarbonyl]-4-(4-methylphenyl)piperazine was reacted by the same way with the example 199 to obtain the titled compound.

yield: 95.2%

EXAMPLE 201)

Methyl N-(5,6-dimethyl-2-methoxypyridin-3-yl)-[4-(4-n-butylphenyl)piperazin-1-yl]iminothiolate 1-[(5,6-Dimethyl-2-methoxypyridin-3-yl)aminothiocarbonyl]-4-(4-n-butylphenyl)piperazine was reacted by the same way with the example 199 to obtain the titled compound.

yield: 93.4%

EXAMPLE 202)

Methyl N-(5,6-dimethyl-2-methoxypyridin-3-yl)-[4-(3,5-dimethylphenyl)piperazin-1-yl]iminothiolate 1-[(5,6-Dimethyl-2-methoxypyridin-3-yl)aminothiocarbonyl]-4-(3,5-dimethylphenyl)piperazine was reacted by the same way with the example 199 to obtain the titled compound.

yield: 97.2%

EXAMPLE 203)

Methyl N-(5,6-dimethyl-2-methoxypyridin-3-yl)-[4-(2-methoxyphenyl)piperazin-1-yl]iminothiolate 1-[(5,6-Dimethyl-2-methoxypyridin-3-yl)aminothiocarbonyl]-4-(2-methoxyphenyl)piperazine was reacted by the same way with the example 199 to obtain the titled compound.

yield: 97.4%

EXAMPLE 204)

Methyl N-(5.6-dimethyl-2-methoxypyridin-3-yl)-[4-(3,5-dimethoxyphenyl)piperazin-1-yl]iminothiolate 1-[(5,6-Dimethyl-2-methoxypyridin-3-yl)aminothiocarbonyl]-4-(3,5-dimethoxyphenyl)piperazine was reacted by the same way with the example 199 to obtain the titled compound.

yield: 95.2%

EXAMPLE 205)

Methyl N-(5,6-dimethyl-2-methoxypyridin-3-yl)-[4-(3,5-di-fluorophenyl)piperazin-1-yl]iminothiolate 1-[(5,6-Dimethyl-2-methoxypyridin-3-yl)aminothiocarbonyl]-4-(3,5-difluorophenyl)piperazine was reacted by the same way with the example 199 to obtain the titled compound.

yield: 90.1%

EXAMPLE 206)

Methyl N-(5,6-dimethyl-2-methoxypyridin-3-yl)-[4-(3,5-di-chlorophenyl)piperazin-1-yl]iminothiolate 1-[(5,6-Dimethyl-2-methoxypyridin-3-yl)aminothiocarbonyl]-4-(3,5-di-chlorophenyl)piperazine was reacted by the same way with the example 199 to obtain the titled compound.

yield: 92.5%

EXAMPLE 207)

Methyl N-(5,6-dimethyl-2-methoxypyridin-3-yl)-[4-(3-bromophenyl)piperazin-1-yl]iminothiolate 1-[(5,6-Dimethyl-2-methoxypyridin-3-yl)aminothiocarbonyl]-4-(3-bromophenyl)piperazine was reacted by the same way with the example 199 to obtain the titled compound.

yield: 89.5%

EXAMPLE 208)

Methyl N-(5,6-dimethyl-2-methoxypyridin-3-yl)-[4-(3,5-di-nitrophenyl)piperazin-1-yl]iminothiolate 1-[(5,6-Dimethyl-2-methoxypyridin-3-yl)aminothiocarbonyl]-4-(3,5-dinitrophenyl)piperazine was reacted by the same way with the example 199 to obtain the titled compound.

yield: 92.9%

EXAMPLE 209)

Methyl N-(5,6-dimethyl-2-methoxypyridin-3-yl)-[4-(3,5-di-ethylisophthal-1-yl)piperazin-1-yl]iminothiolate 1-[(5,6-Dimethyl-2-methoxypyridin-3-yl)aminothiocarbonyl]-4-(3,5-diethylisophthal-1-yl)piperazine was reacted by the same way with the example 199 to obtain the titled compound.

yield: 92.9%

EXAMPLE 210)

Methyl N-(5-ethyl-2-methoxy-6-methylpyridin-3-yl)-(4-phenyl)piperazin-1-yl]iminothiolate 1-[(5-Ethyl-2-methoxy-6-methylpyridin-3-yl) aminothiocarbonyl]-4-phenylpiperazine was reacted by the same way with the example 199 to obtain the titled compound.

yield: 92.2%

EXAMPLE 211)

Methyl N-(5-ethyl-2-methoxy-6-methylpyridin-3-yl)-[4-(2-methoxyphenyl)piperazin-1-yl]iminothiolate 1-[(5-Ethyl-2-methoxy-6-methylpyridin-3-yl) aminothiocarbonyl]-4-(2-methoxyphenyl)piperazine was reacted by the same way with the example 199 to obtain the titled compound.

yield: 87.2%

EXAMPLE 212)

Methyl N-(5-ethyl-2-methoxy-6-methylpyridin-3-yl)-[4-(3,5-dimethoxyphenyl)piperazin-1-yl]iminothiolate 1-[(5-Ethyl-2-methoxy-6-methylpyridin-3-yl) aminothiocarbonyl]-4-(3,5-dimethoxyphenyl)piperazine was reacted by the same way with the example 199 to obtain the titled compound.

yield: 92.4%

EXAMPLE 213)

Methyl N-(5-ethyl-2-methoxy-6-methylpyridin-3-yl)-[4-(2-ethylphenyl)piperazin-1-yl]iminothiolate 1-[(5-Ethyl-2-methoxy-6-methylpyridin-3-yl) aminothiocarbonyl]-4-(2-ethylphenyl)piperazin was reacted by the same way with the example 199 to obtain the titled compound.

yield: 93.6%

EXAMPLE 214)

Methyl N-(5-ethyl-2-methoxy-6-methylpyridin-3-yl)-[4-(3,5-dimethylphenyl)piperazin-1-yl]iminothiolate 1-[(5-Ethyl-2-methoxy-6-methylpyridin-3-yl) aminothiocarbonyl]-4-(3,5-dimethylphenyl)piperazine was reacted by the same way with the example 199 to obtain the titled compound.

yield: 96.2%

EXAMPLE 215)

Methyl N-(5-ethyl-2-methoxy-6-methylpyridin-3-yl)-[4-(3,5-difluorophenyl)piperazin-1-yl]iminothiolate 1-[(5-Ethyl-2-methoxy-6-methylpyridin-3-yl) aminothiocarbonyl]-4-(3,5-difluorophenyl)piperazine was reacted by the same way with the example 199 to obtain the titled compound.

yield: 92.5%

EXAMPLE 216)

Methyl N-(5-ethyl-2-methoxy-6-methylpyridin-3-yl)-[4-(3,5-dichlorophenyl)piperazin-1-yl]iminothiolate 1-[(5-Ethyl-2-methoxy-6-methylpyridin-3-yl) aminothiocarbonyl]-4-(3,5-dichlorophenyl)piperazine was reacted by the same way with the example 199 to obtain the titled compound.

yield: 93.2%

EXAMPLE 217)

Methyl N-(5-ethyl-2-methoxy-6-methylpyridin-3-yl)-[4-(2-phenylphenyl)piperazin-1-yl]iminothiolate 1-[(5-Ethyl-2-methoxy-6-methylpyridin-3-yl) aminothiocarbonyl]-4-(2-phenylphenyl)piperazine was reacted by the same way with the example 199 to obtain the titled compound.

yield: 91.4%

EXAMPLE 218)

Methyl N-(5-ethyl-2-methoxy-6-methylpyridin-3-yl)-[4-(3,5-dinitrophenyl)piperazin-1-yl]iminothiolate 1-[(5-Ethyl-2-methoxy-6-methylpyridin-3-yl) aminothiocarbonyl]-4-(3,5-dinitrophenyl)piperazine was reacted by the same way with the example 199 to obtain the titled compound.

yield: 94.2%

EXAMPLE 219)

Methyl N-(5-ethyl-2-methoxy-6-methylpyridin-3-yl)-[4-(2-methylthiophenyl)piperazin-1-yl]iminothiolate 1-[(5-Ethyl-2-methoxy-6-methylpyridin-3-yl) aminothiocarbonyl]-4-(2-methylthiophenyl)piperazine was reacted by the same way with the example 199 to obtain the titled compound.

yield: 90.5%

EXAMPLE 220)

Methyl N-(5-methoxycarbonyl-2-methoxy-6-methylpyridin-3-yl)-[4-(3,5-dimethoxyphenyl) piperazin-1-yl]iminothiolate 1-[(5-Methoxycarbonyl-2-methoxy-6-methylpyridin-3-yl)aminothiocarbonyl]-4-(3,5-dimethoxyphenyl)piperazine was reacted by the same way with the example 199 to obtain the titled compound.

yield: 93.2%

EXAMPLE 221)

Methyl N-(5-methoxycarbonyl-2-methoxy-6-methylpyridin-3-yl)-[4-(3,5-dimethylphenyl) piperazin-1-yl]iminothiolate 1-[(5-Methoxycarbonyl-2-methoxy-6-methylpyridin-3-yl)aminothiocarbonyl]-4-(3,5-dimethylphenyl)piperazine was reacted by the same way with the example 199 to obtain the titled compound.

yield: 92.9%

EXAMPLE 222)

Methyl N-(5-methoxycarbonyl-2-methoxy-6-methylpyridin-3-yl)-[4-(3,5-difluorophenyl) piperazin-1-yl]iminothiolate 1-[(5-Methoxycarbonyl-2-methoxy-6-methylpyridin-3-yl)aminothiocarbonyl]-4-(3,5-difluorophenyl)piperazine

EXAMPLE 223)

Methyl N-(5-methoxycarbonyl-2-methoxy-6-methylpyridin-3-yl)-[4-(2-methoxyphenyl)piperazin-1-yl]iminothiolate 1-[(5-Methoxycarbonyl-2-methoxy-6-methylpyridin-3-yl)aminothiocarbonyl]-4-(2-methoxyphenyl)piperazine was reacted by the same way with the example 199 to obtain the titled compound.

yield: 90.2%

EXAMPLE 224)

Methyl N-(5-methoxycarbonyl-2-methoxy-6-methylpyridin-3-yl)-(4-phenylpiperazin-1-yl)iminothiolate 1-[(5-Methoxycarbonyl-2-methoxy-6-methylpyridin-3-yl)aminothiocarbonyl]-4-phenylpiperazine was reacted by the same way with the example 199 to obtain the titled compound.

yield: 93.5%

EXAMPLE 225)

Methyl N-(5-methoxycarbonyl-2-methoxy-6-methylpyridin-3-yl)-[4-(4-methylphenyl)piperazin-1-yl]iminothiolate 1-[(5-Methoxycarbonyl-2-methoxy-6-methylpyridin-3-yl)aminothiocarbonyl]-4-(4-methylphenyl)piperazine with the example 199 to obtain the titled compound.

yield: 97.5%

EXAMPLE 226)

Methyl N-(5-methoxycarbonyl-2-methoxy-6-methylpyridin-3-yl)-[4-(2-chlorophenyl)piperazin-1-yl]iminothiolate 1-[(5-Methoxycarbonyl-2-methoxy-6-methylpyridin-3-yl)aminothiocarbonyl]-4-(2-chlorophenyl)piperazine with the example 199 to obtain the titled compound.

yield: 95.5%

EXAMPLE 227)

Methyl N-(2-methoxy-5-methylcarbonyl-6-methylpyridin-3-yl)-[4-(3,5-dimethylphenyl)piperazin-1-yl]iminothiolate 1-[(5-Methoxycarbonyl-2-methoxy-6-methylpyridin-3-yl)aminothiocarbonyl]-4-(3,5-dimethylphenyl)piperazine way with the example 199 to obtain the titled compound.

yield: 96.2%

EXAMPLE 228)

Methyl N-(2-methoxy-5-methylcarbonyl-6-methylpyridin-3-yl)-[4-(3,5-dimethoxyphenyl)piperazin-1-yl]iminothiolate 1-[(5-Methoxycarbonyl-2-methoxy-6-methylpyridin-3-yl)aminothiocarbonyl]-4-(3,5-dimethoxyphenyl)piperazine way with the example 199 to obtain the titled compound.

yield: 95.4%

EXAMPLE 229)

Methyl N-(2-methoxy-5-methylcarbonyl-6-methylpyridin-3-yl)-(4-phenylpiperazin-1-yl)iminothiolate 1-[(5-Methoxycarbonyl-2-methoxy-6-methylpyridin-3-yl)aminothiocarbonyl]-4-phenylpiperazine was reacted by the same way with the example 199 to obtain the titled compound.

yield: 90.1%

EXAMPLE 230)

Methyl N-(2-methoxy-5-methylcarbonyl-6-methylpyridin-3-yl)-[4-(4-methylphenyl)piperazin-1-yl]iminothiolate 1-[(5-Methoxycarbonyl-2-methoxy-6-methylpyridin-3-yl)aminothiocarbonyl]-4-(4-methylphenyl)piperazine was reacted by the same way with the example 199 to obtain the titled compound.

yield: 92.2%

EXAMPLE 231)

Methyl N-(2-methoxy-5-methylcarbonyl-6-methylpyridin-3-yl)-[4-(3,5-difluorophenyl)piperazin-1-yl]iminothiolate 1-[(5-Methoxycarbonyl-2-methoxy-6-methylpyridin-3-yl)aminothiocarbonyl]-4-(3,5-difluorophenyl)piperazine was reacted by the same way with the example 199 to obtain the titled compound.

yield: 93.1%

EXAMPLE 232)

Methyl N-(2-methoxy-5-methylcarbonyl-6-methylpyridin-3-yl)-[4-(2-methylthiophenyl)piperazin-1-yl]iminothiolate 1-[(5-Methoxycarbonyl-2-methoxy-6-methylpyridin-3-yl)aminothiocarbonyl]-4-(2-methylthiophenyl)piperazine was reacted by the same way with the example 199 to obtain the titled compound.

yield: 90.0%

EXAMPLE 233)

Methyl N-(6-ethyl-5-methoxycarbonyl-2-methoxypyridin-3-yl)-[4-(4-methylphenyl)piperazin-1-yl]iminothiolate 1-[(6-Ethyl-5-methoxycarbonyl-2-methoxypyridin-3-yl)aminothiocarbonyl]-4-(4-methylphenyl)piperazine was reacted by the same way with the example 199 to obtain the titled compound.

yield: 91.1%

EXAMPLE 234)

Methyl N-(6-ethyl-5-methoxycarbonyl-2-methoxypyridin-3-yl)-[4-(2-ethylphenyl)piperazin-1-yl]iminothiolate 1-[(6-Ethyl-5-methoxycarbonyl-2-methoxypyridin-3-yl)aminothiocarbonyl]-4-(2-ethylphenyl)piperazine was reacted by the same way with the example 199 to obtain the titled compound.

yield: 90.4%

(Note: top of page 61 begins with: "was reacted by the same way with the example 199 to obtain the titled compound. yield: 88.5%")

EXAMPLE 235)

Methyl N-(6-ethyl-5-methoxycarbonyl-2-methoxypyridin-3-yl)-[4-(3,5-dimethylphenyl)piperazin-1-yl]iminothiolate 1-[(6-Ethyl-5-methoxycarbonyl-2-methoxypyridin-3-yl)aminothiocarbonyl]-4-(3,5-dimethylphenyl)piperazine was reacted by the same way with the example 199 to obtain the titled compound.

yield: 95.5%

EXAMPLE 236)

Methyl N-(6-ethyl-5-methoxycarbonyl-2-methoxypyridin-3-yl)-[4-(3,5-dimethoxyphenyl)piperazin-1-yl]iminothiolate 1-[(6-Ethyl-5-methoxycarbonyl-2-methoxypyridin-3-yl)aminothiocarbonyl]-4-(3,5-dimethoxyphenyl)piperazine was reacted by the same way with the example 199 to obtain the titled compound.

yield: 95.4%

EXAMPLE 237)

Methyl N-(6-ethyl-5-methoxycarbonyl-2-methoxypyridin-3-yl)-[4-(3,5-dichlorophenyl)piperazin-1-yl]iminothiolate 1-[(6-Ethyl-5-methoxycarbonyl-2-methoxypyridin-3-yl)aminothiocarbonyl]-4-(3,5-dichlorophenyl)piperazine was reacted by the same way with the example 199 to obtain the titled compound.

yield: 90.5%

EXAMPLE 238)

Methyl N-(6-ethyl-5-methoxycarbonyl-2-methoxypyridin-3-yl)-[4-(2-methylthiophenyl)piperazin-1-yl]iminothiolate 1-[(6-Ethyl-5-methoxycarbonyl-2-methoxypyridin-3-yl)aminothiocarbonyl]-4-(2-methylthiophenyl)piperazine was reacted by the same way with the example 199 to obtain the titled compound.

yield: 92.0%

EXAMPLE 239)

Methyl N-(6-ethyl-5-methoxycarbonyl-2-methoxypyridin-3-yl)-[4-(3,5-diethylisophthalate-1-yl)piperazine-1-yl]iminothi-olate 1-[(6-Ethyl-5-methoxycarbonyl-2-methoxypyridin-3-yl)aminothiocarbonyl]-4-(3,5-diethylisophthalate-1-yl)piperazine was reacted by the same way with the example 199 to obtain the titled compound.

yield: 93.2%

EXAMPLE 240)

Methyl N-(6-ethyl-5-methoxycarbonyl-2-methoxypyridin-3-yl)-[4-(3,5-difluorophenyl)piperazin-1-yl]iminothiolate 1-[(6-Ethyl-5-methoxycarbonyl-2-methoxypyridin-3-yl)aminothiocarbonyl]-4-(3,5-difluorophenyl)piperazine was reacted by the same way with the example 199 to obtain the titled compound.

yield: 95.2%

EXAMPLE 241)

Methyl N-(2-methoxyquinolin-3-yl)-[4-(3,5-dimethoxyphenyl)piperazin-1-yl]-iminothiolate 1-[(2-Methoxyquinolin-3-yl)aminothiocarbonyl]-4-(3,5-dimethoxyphenyl)piperazine was reacted by the same way with the example 199 to obtain the titled compound.

yield: 90.3%

EXAMPLE 242)

Methyl N-(2-methoxyquinolin-3-yl)-[4-(3,5-dimethylphenyl)piperazin-1-yl]-iminothiolate 1-[(2-Methoxyquinolin-3-yl)aminothiocarbonyl]-4-(3,5-dimethylphenyl)piperazine was reacted by the same way with the example 199 to obtain the titled compound.

yield: 91.1%

EXAMPLE 243)

Methyl N-(2-methoxyquinolin-3-yl)-[4-(3,5-difluorophenyl)piperazin-1-yl]iminothiolate 1-[(2-Methoxyquinolin-3-yl )aminothiocarbonyl]-4-(3,5-difluorophenyl)piperazine was reacted by the same way with the example 199 to obtain the titled compound.

yield: 94.2%

EXAMPLE 244)

Methyl N-(2-methoxyquinolin-3-yl)-[4-(2-methoxyphenyl)piperazin-1-yl]iminothiolate 1-[(2-Methoxyquinolin-3-yl)aminothiocarbonyl]-4-(2-methoxyphenyl)piperazine was reacted by the same way with the example 199 to obtain the titled compound.

yield: 92.4%

EXAMPLE 245)

Methyl N-(2-methoxyquinolin-3-yl)-[4-(3-chlorophenyl)piperazine-1-yl]-iminothiolate 1-[(2-Methoxyquinolin-3-yl)aminothiocarbonyl]-4-(3-chlorophenyl)piperazine was reacted by the same way with the example 199 to obtain the titled compound.

yield: 90.3%

EXAMPLE 246)

Methyl N-(4,5-dimethyl-2-methoxyphenyl-1-yl)-(4-phenyl-piperazin-1-yl)-iminothiolate 1-[(4,5-Dimethyl-2-methoxyphenyl-1-yl)aminothiocarbonyl]-4-phenylpiperazine was reacted by the same way with the example 199 to obtain the titled compound.

yield: 95.4%

EXAMPLE 247)

Methyl N-(4,5-dimethyl-2 methoxyphenyl-1-yl)-[4-(4-methylphenyl)piperazin-1-yl]iminothiolate 1-[(4,5-Dimethyl-2-methoxyphenyl-1-yl)aminothiocarbonyl]-4-(4-methylphenyl)piperazine was reacted by the same way with the example 199 to obtain the titled compound.

yield: 94.4%

EXAMPLE 248)

Methyl N-(4,5-dimethyl-2-methoxyphenyl-1-yl)-[4-(2-ethylphenyl)piperazin-1-yl]iminothiolate 1-[(4,5-Dimethyl-2-methoxyphenyl-1-yl)aminothiocarbonyl]-4-(2-ethylphenyl)piperazine was reacted by the same way with the example 199 to obtain the titled compound.

yield: 96.2%

EXAMPLE 249)

Methyl N-(4,5-dimethyl-2-methoxyphenyl-1-yl)-[4-(3,5-dimethylphenyl)piperazin-1-yl]iminothiolate 1-[(4,5-Dimethyl-2-methoxyphenyl-1-yl)aminothiocarbonyl]-4-(3,5-dimethylphenyl)piperazine was reacted by the same way with the example 199 to obtain the titled compound.

yield: 96.8%

EXAMPLE 250)

Methyl N-(4,5-dimethyl-2-methoxyphenyl-1-yl)-[4-(3,5-dimethoxyphenyl)piperazin-1-yl]iminothiolate 1-[(4,5-Dimethyl-2-methoxyphenyl-1-yl)aminothiocarbonyl]-4-(3,5-dimethoxyphenyl)piperazine was reacted by the same way with the example 199 to obtain the titled compound.

yield: 95.7%

EXAMPLE 251)

Methyl N-(4,5-dimethyl-2-methoxyphenyl-1-yl)-[4-(3,5-difluorophenyl)piperazin-1-yl]iminothiolate 1-[(4,5-Dimethyl-2-methoxyphenyl-1-yl)aminothiocarbonyl]-4-(3,5-difluorophenyl)piperazine was reacted by the same way with the example 199 to obtain the titled compound.

yield: 90.4%

EXAMPLE 252)

Methyl N-(4,5-dimethyl-2-methoxyphenyl-1-yl)-[4-(3-chlorophenyl)piperazin-1-yl]iminothiolate 1-[(4,5-Dimethyl-2-methoxyphenyl-1-yl)aminothiocarbonyl]-4-(3-chlorophenyl)piperazine was reacted by the same way with the example 199 to obtain the titled compound.

yield: 94.2%

EXAMPLE 253)

Methyl N-(4,5-dimethyl-2-methoxyphenyl-1-yl)-[4-(3-bromophenyl)piperazin-1-yl]iminothiolate 1-[(4,5-Dimethyl-2-methoxyphenyl-1-yl)aminothiocarbonyl]-4-(3-bromophenyl)piperazine was reacted by the same way with the example 199 to obtain the titled compound.

yield: 94.4%

EXAMPLE 254)

Methyl N-(4,5-dimethyl-2-methoxyphenyl-1-yl)-[4-(2-methylthiophenyl)piperazin-1-yl]iminothiolate 1-[(4,5-Dimethyl-2-methoxyphenyl-1-yl)aminothiocarbonyl]-4-(2-methylthiophenyl)piperazine was reacted by the same way with the example 199 to obtain the titled compound.

yield: 93.5%

Physical data of the compounds prepared in the above examples are as follows

EXAMPLE 1

$^1$H NMR(CDCl$_3$): δ2.37 (3H,s), 2.39(3H,s), 3.27(4H,t), 3.74(4H,t), 3.97(3H,s), 6.97(2H,m), 7.31(2H,t)

EXAMPLE 2

$^1$H NMR(CDCl$_3$): δ2.36(3H,s), 2.40(3H,s), 3.13(4H,t), 3.75(4H,t), 3.89(3H,s), 3.97(3H,s), 6.95(3H,m), 7.05(2H,m)

EXAMPLE 3

$^1$H NMR(CDCl$_3$): δ2.37(3H,s), 2.39(3H,s), 3.25(4H,t), 3.71(4H,t), 3.79(6H,s), 3.97(3H,s), 6.10(3H,m)

EXAMPLE 4

$^1$H NMR(CDCl$_3$): δ1.26(3H,t), 2.37(3H,s), 2.41(3H,s), 2.74(2H,q), 2.94(4H,t), 3.68(4H,t), 3.97(3H,s), 6.72(1H, brs), 7.08(2H,m), 7.19(1H,t), 7.25(1H,s)

EXAMPLE 5

$^1$H NMR(CDCl$_3$): δ0.92(3H,t), 1.35(2H,m), 1.57(2H,m), 2.37(3H,s), 2.39(3H,s), 2.56(2H,t), 3.25(4H,t), 3.78(4H,t), 3.97(3H,s), 6.95(2H,brs), 7.14(2H,m)

EXAMPLE 6

$^1$H NMR(CDCl$_3$): δ1.23(6H,d), 2.38(3H,s), 2.42(3H,s), 2.95(4H,t), 3.53(1H,m), 3.72(4H,t), 3.98(3H,s), 7.11(1H,m), 7.29(1H,m)

EXAMPLE 7

$^1$H NMR(CDCl$_3$): δ2.30(6H,s), 2.37(3H,s), 2.40(3H,s), 3.25(4H,t), 3.75(4H,t), 3.97(3H,s), 6.62(3H,m)

EXAMPLE 8

$^1$H NMR(CDCl$_3$): δ2.21(6H,s), 2.22(6H,s), 2.38(3H,s), 2.43(3H,s), 3.17(4H,t), 3.67(4H,t), 4.00(3H,s), 6.84(1H,s)

EXAMPLE 9

$^1$H NMR(CDCl$_3$): δ2.37(3H,s), 2.40(3H,s), 3.14(4H,t), 3.73(4H,t), 3.98(3H,s), 6.99(2H,m), 7.07(2H,m)

EXAMPLE 10

$^1$H NMR(CDCl$_3$): δ2.37(3H,s), 2.39(3H,s), 3.26(4H,t), 3.70(4H,t), 3.98(3H,s), 6.85(1H,m), 7.01(1H,d), 7.05(1H,s), 7.13(1H,t)

EXAMPLE 11

$^1$H NMR(CDCl$_3$): δ2.37(3H,s), 2.39(3H,s), 3.27(4H,t), 3.69(4H,t), 3.98(3H,s), 6.75(2H,s), 6.84(1H,s)

EXAMPLE 12

$^1$H NMR(CDCl$_3$): δ2.37(3H,s), 2.39(3H,s), 3.27(4H,t), 3.69(4H,t), 3.97(3H,s), 6.30(1H,t), 6.37(2H,d)

EXAMPLE 13

$^1$H NMR(CDCl$_3$): δ2.38(3H,s), 2.40(3H,s), 3.31(4H,s), 3.73(4H,t), 3.98(3H,s), 7.09(1H,d), 7.13(2H,m), 7.38(1H,t)

EXAMPLE 14

$^1$H NMR(CDCl$_3$): δ2.38(3H,s), 2.42(3H,s), 2.43(3H,s), 3.05(4H,t), 3.73(4H,t), 3.99(3H,s), 7.05(1H,brs), 7.13(1H,s)

EXAMPLE 15

$^1$H NMR(CDCl$_3$): δ2.39(3H,s), 2.45(3H,s), 3.57(4H,t), 3.88(4H,t), 4.08(3H,s), 7.98(2H,s), 8.45(1H,s)

EXAMPLE 16

$^1$H NMR(CDCl$_3$): δ2.38(3H,s), 2.40(3H,s), 3.26(4H,t), 3.70(4H,t), 3.98(3H,s), 6.35(1H,s), 6.42(2H,s)

EXAMPLE 17

$^1$H NMR(CDCl$_3$): δ2.38(3H,s), 2.40(3H,s), 2.54(3H,s), 3.46(4H,t), 3.74(4H,t), 3.99(3H,s), 6.88(2H,d), 7.90(2H,d)

EXAMPLE 18

$^1$H NMR(CDCl$_3$): δ2.39(3H,s), 2.40(3H,s), 2.91(4H,t), 3.22(3H,s), 3.46(4H,t), 3.85(3H,s), 3.95(3H,s), 6.89(3H,m), 7.02(1H,m)

EXAMPLE 19

$^1$H NMR(CDCl$_3$): δ2.39(3H,s), 2.40(3H,s), 3.01(4H,t), 3.21(3H,s), 3.40(4H,t), 3.75(6H,s), 3.92(3H,s), 6.03(3H,s)

EXAMPLE 20

$^1$H NMR(CDCl$_3$): δ2.26(6H,s), 2.39(3H,s), 2.40(3H,s), 2.99(4H,t), 3.22(3H,s), 3.40(4H,t), 3.93(3H,s), 6.52(3H,m)

EXAMPLE 21

$^1$H NMR(CDCl$_3$): δ2.40(3H,s), 2.41(3H,s), 3.03(4H,t), 3.21(3H,s), 3.38(4H,t), 3.93(3H,s), 6.68(2H,s), 6.81(1H,s)

EXAMPLE 22

$^1$H NMR(CDCl$_3$): δ2.40(3H,s), 2.41(3H,s), 3.03(4H,t), 3.21(3H,s), 3.39(4H,t), 3.93(3H,s), 6.27(3H,m)

EXAMPLE 23

$^1$H NMR(CDCl$_3$): δ2.40(9H,s), 2.87(4H,t), 3.22(3H,s), 3.46(4H,t), 3.96(3H,s), 7.02(1H,brs), 7.11(3H,s)

EXAMPLE 24

$^1$H NMR(CDCl$_3$): δ2.43(6H,s), 3.24(3H,s), 3.27(4H,t), 3.45(4H,t), 3.95(3H,s), 7.89(2H,d), 8.40(1H,s)

EXAMPLE 25

$^1$H NMR(CDCl$_3$): δ2.38(3H,s), 2.39(3H,s), 2.95(4H,t), 3.21(3H,s), 3.37(4H,t), 3.92(3H,s), 5.62(1H,s), 5.65(2H,s)

EXAMPLE 26

$^1$H NMR(CDCl$_3$): δ1.65(3H,t), 2.39(3H,s), 2.40(3H,s), 2.96(4H,t), 3.35(4H,t), 3.74(2H,q), 3.75(6H,s), 3.92(3H,s), 6.02(3H,s)

EXAMPLE 27

$^1$H NMR(CDCl$_3$): δ1.17(3H,t), 2.25(6H,s), 2.39(3H,s), 2.40(3H,s), 2.95(4H,t), 3.36(4H,t), 3.74(2H,q), 3.92(3H,s), 6.50(3H,m)

EXAMPLE 28

$^1$H NMR(CDCl$_3$): δ2.32(3H,s), 2.34(3H,s), 3.34(4H,t), 3.78(6H,s), 3.98(3H,s), 4.07(4H,t), 6.12(3H,m)

EXAMPLE 29

$^1$H NMR(CDCl$_3$): δ1.26(3H,t), 2.35(3H,s), 2.37(3H,s), 2.74(2H,q), 3.02(4H,t), 3.97(3H,s), 4.02(4H,t), 7.09(2H,q), 7.19(1H,t), 7.55(1H,s)

EXAMPLE 30

$^1$H NMR(CDCl$_3$): δ2.29(6H,s), 2.32(3H,s), 2.35(3H,s), 3.31(4H,t), 3.98(3H,s), 4.04(4H,t), 6.59(3H,brs)

EXAMPLE 31

$^1$H NMR(CDCl$_3$): δ2.32(3H,s), 2.35(3H,s), 3.33(4H,t), 3.98(3H,s), 4.06(4H,t), 6.82(1H,d), 7.01(2H,m), 7.13(1H,t)

EXAMPLE 32

$^1$H NMR(CDCl$_3$): δ2.44(3H,s), 2.49(3H,s), 3.48(4H,t), 4.05(3H,s), 4.25(4H,t), 6.98(3H,m)

EXAMPLE 33

$^1$H NMR(CDCl$_3$): δ2.35(3H,s), 2.36(3H,s), 2.43(3H,s), 3.12(4H,t), 3.97(3H,s), 4.05(4H,t), 6.87(1H,d), 7.05(1H,brs), 7.13(2H,t)

EXAMPLE 34

$^1$H NMR(CDCl$_3$): δ1.26(6H,m), 2.30(6H,s), 2.70(2H,t), 2.78(2H,t), 3.25(4H,t), 3.74(4H,t), 3.99(3H,s), 6.65(3H,m)

EXAMPLE 35

$^1$H NMR(CDCl$_3$): δ1.24(6H,m), 2.69(2H,t), 2.78(2H,t), 3.24(4H,t), 3.71(4H,t), 3.78(6H,s), 3.98(3H,s), 6.07(1H,s), 6.11(2H,brs)

EXAMPLE 36

$^1$H NMR(CDCl$_3$): δ3.34(4H,t), 3.88(4H,t), 4.15(3H,s), 7.05(3H,m), 7.35(3H,m), 7.43(2H,m), 7.70(1H,brs)

EXAMPLE 37

$^1$H NMR(CDCl$_3$): δ3.17(4H,t), 3.83(4H,t), 3.90(3H,s), 4.16(3H,s), 6.99(4H,m), 7.49(2H,m), 7.75(2H,m)

EXAMPLE 38

$^1$H NMR(CDCl$_3$): δ3.22(4H,t), 3.30(4H,t), 3.79(6H,s), 4.11(3H,s), 7.20(1H,d), 7.33(2H,m), 7.50(2H,m), 7.62(1H,d), 7.76(1H,m), 7.83(1H,m)

EXAMPLE 39

$^1$H NMR(CDCl$_3$): δ1.28(3H,t), 2.78(2H,q), 3.02(4H,t), 3.89(4H,t), 4.15(3H,s), 7.13(2H,m), 7.21(1H,t), 7.28(1H,m), 7.43(3H,m), 7.70(1H,d)

EXAMPLE 40

$^1$H NMR(CDCl$_3$): δ1.24(6H,d), 2.98(4H,t), 3.56(1H,m), 3.82(4H,t), 4.15(3H,s), 7.16(3H,m), 7.30(1H,d), 7.43(2H,brs), 7.69(2H,d)

EXAMPLE 41

$^1$H NMR(CDCl$_3$): δ0.93(3H,t), 1.35(2H,m), 1.57(2H,m), 2.56(2H,t), 3.35(4H,t), 3.88(4H,t), 4.15(3H,s), 7.19(3H,brs), 7.43(3H,brs), 7.70(2H,brs)

EXAMPLE 42

$^1$H NMR(CDCl$_3$): δ2.30(6H,s), 3.26(4H,t), 3.78(4H,t), 4.14(3H,s), 6.60(3H,m), 7.30(2H,m), 7.50(1H,s), 7.55(1H,m)

EXAMPLE 43

$^1$H NMR(CDCl$_3$): δ2.21(6H,s), 2.34(6H,s), 3.20(4H,t), 3.83(4H,t), 4.17(3H,s), 6.85(1H,s), 7.46(2H,m), 7.61(1H,brs), 7.72(1H,d)

EXAMPLE 44

$^1$H NMR(CDCl$_3$): δ3.20(4H,t), 3.91(4H,t), 4.15(3H,s), 7.07(4H,m), 7.42(3H,m), 7.70(1H,d)

EXAMPLE 45

¹H NMR(CDCl₃): δ3.30(4H,t), 3.90(4H,t), 4.16(3H,s), 6.95(1H,d), 7.05(1H,d), 7.15(2H,m), 7.42(2H,m), 7.53(1H,s), 7.69(1H,d)

EXAMPLE 46

¹H NMR(CDCl₃): δ3.27(4H,t), 3.78(4H,t), 4.16(3H,s), 6.39(3H,m), 7.52(2H,m), 7.74(2H,m)

EXAMPLE 47

¹H NMR(CDC₃): δ3.34(4H,t), 3.90(4H,t), 4.16(3H,s), 7.15(3H,m), 7.40(3H,m), 7.52(1H,brs), 7.70(1H,d)

EXAMPLE 48

¹H NMR(CDCl₃): δ3.55(4H,t), 3.98(4H,t), 4.19(3H,s), 7.46(3H,m), 7.73(1H,m), 8.00(2H,s), 8.44(1H,s)

EXAMPLE 49

¹H NMR(CDCl₃): δ3.25(4H,t), 3.73(4H,t), 4.13(3H,s), 5.68(1H,brs), 5.79(2H,brs), 7.49(2H,m), 7.74(2H,m)

EXAMPLE 50

¹H NMR(CDCl₃): δ2.54(3H,s), 3.49(4H,t), 3.92(4H,t), 4.16(3H,s), 6.95(2H,d), 7.43(2H,m), 7.51(1H,brs), 7.71(1H,d), 7.92(2H,d)

EXAMPLE 51

¹H NMR(CDCl₃): δ2.47(3H,s), 3.30(4H,t), 4.04(4H,t), 4.19(3H,s), 7.20(3H,brs), 7.47(2H,m), 7.60(2H,m), 7.76(1H,m)

EXAMPLE 52

¹H NMR(CDCl₃): δ2.92(4H,t), 3.57(4H,t), 4.11(3H,s), 7.15(1H,d), 7.12(1H,t), 7.30(4H,m), 7.41(4H,m), 7.54(1H,m), 7.64(3H,m)

EXAMPLE 53

¹H NMR(CDCl₃): δ3.19(4H,t), 3.38(3H,s), 3.68(4H,t), 3.78(6H,s), 4.07(3H,s), 6.09(3H,brm), 7.50(2H,m), 7.80(2H,m)

EXAMPLE 54

¹H NMR(CDCl₃): δ3.08(4H,t), 3.39(3H,s), 3.73(4H,t), 3.88(3H,s), 4.09(3H,s), 6.92(4H,m), 7.50(2H,m), 7.80(2H,m)

EXAMPLE 55

¹H NMR(CDCl₃): δ2.30(6H,s), 3.19(4H,t), 3.39(3H,s), 3.70(4H,t), 4.08(3H,s), 6.59(3H,brs), 7.52(2H,s), 7.80(2H,m)

EXAMPLE 56

¹H NMR(CDCl₃): δ3.20(4H,t), 3.39(3H,s), 3.66(4H,t), 4.07(3H,s), 6.35(3H,m), 7.52(2H,m), 7.82(2H,m)

EXAMPLE 57

¹H NMR(CDCl₃): δ3.41(3H,s), 3.43(4H,t), 3.71(4H,t), 4.09(3H,s), 7.55(2H,m), 7.79(1H,m), 7.88(1H,m), 7.96(2H,s), 8.44(1H,s)

EXAMPLE 58

¹H NMR(CDCl₃): δ3.13(4H,t), 3.37(3H,s), 3.65(4H,t), 3.94(3H,s), 5.59(2H,m), 5.61(1H,s), 7.50(2H,m), 7.77(1H,m), 7.82(1H,m)

EXAMPLE 59

¹H NMR(CDCl₃): δ1.33(3H,t), 3.15(4H,t), 3.65(4H,t), 3.77(6H,s), 3.91(2H,q), 4.08(3H,s), 6.09(3H,brs), 7.52(2H,m), 7.80(2H,m)

EXAMPLE 60

¹H NMR(CDCl₃): δ1.34(3H,t), 2.28(6H,s), 3.12(4H,t), 3.62(4H,t), 3.91(2H,q), 4.08(3H,s), 6.55(3H,brs), 7.51(2H,m), 7.80(2H,m)

EXAMPLE 61

¹H NMR(CDCl₃): δ1.33(3H,t), 3.15(4H,t), 3.61(4H,t), 3.91(2H,q), 4.08(3H,s), 6.77(2H,s), 6.87(1H,s), 7.53(2H,m), 7.78(1H,m), 7.85(1H,m)

EXAMPLE 62

¹H NMR(CDCl₃): δ1.43(6H,d), 2.98(4H,t), 3.48(4H,d), 3.74(6H,s), 4.06(3H,s), 4.71(1H,m), 5.99(2H,s), 6.01(1H,s), 7.53(2H,m), 7.77(1H,m), 7.84(1H,m)

EXAMPLE 63

¹H NMR(CDCl₃): δ3.49(4H,t), 3.96(3H,s), 4.15(3H,s), 4.31(4H,t), 7.06(3H,m), 7.44(3H,m), 7.71(2H,d)

EXAMPLE 64

¹H NMR(CDCl₃): δ3.40(4H,tI, 3.80(6H,s), 4.15(3H,s), 4.30(4H,t), 6.16(3H,brs), 6.84(1H,d), 7.23(1H,t), 7.44(2H,brs), 7.70 (1H,brs)

EXAMPLE 65

¹H NMR(CDCl₃): δ1.27(3H,t), 2.76(2H,q), 3.05(4H,t), 4.15(3H,s), 4.39(4H,t), 7.10(2H,m), 7.19(1H,s), 7.40(3H,m), 7.75(1H,m), 8.01(1H,s)

EXAMPLE 66

¹H NMR(CDCl₃): δ2.31(6H,s), 3.36(4H,t), 4.14(3H,s), 4.38(4H,t), 6.64(3H,brs), 7.45(2H,m), 7.72(2H,m)

EXAMPLE 67

¹H NMR(CDCl₃): δ3.34(4H,t), 4.16(3H,s), 4.38(4H,t), 6.85(1H,d), 7.01(1H,d), 7.06(1H,s), 7.15(1H,m), 7.42(3H,m), 7.68(1H,brs)

EXAMPLE 68

¹H NMR(CDCl₃): δ3.42(4H,t), 4.16(3H,s), 4.30(4H,t), 6.39(3H,m), 7.20(1H,t), 7.43(1H,m), 7.69(2H,m)

EXAMPLE 69

¹H NMR(CDCl₃): δ2.46(3H,s), 3.20(4H,t), 4.15(3H,s), 4.30(4H,t), 6.90(1H,m), 7.15(3H,m), 7.45(1H,m), 7.65(1H,t), 7.73(1H,m), 8.01(1H,d)

EXAMPLE 70

¹H NMR(CDCl₃): δ2.56(3H,s), 3.60(4H,t), 4.15(3H,s), 4.30(4H,t), 6.96(2H,d), 7.44(1H,m), 7.59(1H,m), 7.74(2H,m), 7.95(2H,m)

EXAMPLE 71

¹H NMR(CDC₃): δ0.92(3H,t), 1.35(2H,m), 1.57(2H,m), 2.56(2H, t), 3.34(4H,t), 4.11(4H,t), 4.19(3H,s), 6.91(2H,m), 7.14(2H,m), 7.60(1H,t), 7.68(1H,t), 7.98(1H,d), 8.02(1H,d)

EXAMPLE 72

¹H NMR(CDCl₃): δ1.52(3H,t), 3.32(4H,t), 3.79(6H,s), 3.80(4H,t), 4.60(2H,q), 6.14(3H,m), 7.44(2H,brs), 7.69(2H,brs)

EXAMPLE 73

¹H NMR(CDCl₃): δ1.50(3H,t), 3.26(4H,t), 3.86(4H,t), 4.11(2H,q), 4.62(2H,q), 6.95(2H,m), 7.07(1H,brs), 7.55(3H,m), 7.80(2H,m)

EXAMPLE 74

¹H NMR(CDCl₃): δ1.52(3H,t), 2.30(6H,s), 3.30(4H,t), 3.80(4H,t), 4.61(2H,q), 6.62(3H,brs), 7.48(2H,m), 7.76(2H,m)

EXAMPLE 75

¹H NMR(CDCl₃): δ1.52(3H,t), 2.27(3H,s), 2.29(3H,s), 2.98(4H,t), 3.78(4H,t), 4.60(2H,q), 6.94(2H,m), 7.10(1H,m), 7.30(1H,brs), 7.47(2H,brs), 7.74(1H,brs)

EXAMPLE 76

¹H NMR(CDCl₃): δ1.28(3H,t), 1.52(3H,t), 2.79(2H,q), 3.06(4H,t), 3.89(4H,t), 4.61(2H,q), 7.14(2H,m), 7.22(1H,t), 7.28(1H,d), 7.44(2H,m), 7.69(2H,m)

EXAMPLE 77

¹H NMR(CDCl₃): δ1.54(3H,t), 3.36(4H,t), 3.91(4H,t), 4.63(2H,q), 6.88(2H,s), 6.90(1H,s), 7.47(2H,m), 7.59(1H,brs), 7.71(1H,m)

EXAMPLE 78

¹H NMR(CDCl₃): δ1.52(3H,t), 3.30(4H,t), 3.83(4H,t), 4.60(2H,q), 6.90(1H,d), 7.03(1H,d), 7.10(1H,s), 7.15(1H,t), 7.43(2H,brs), 7.69(1H,brs)

EXAMPLE 79

¹H NMR(CDCl₃): δ1.52(3H,t), 3.33(4H,t), 3.77(4H,t), 3.78(4H,t), 4.68(2H,q), 6.31(1H,t), 6.40(2H,d), 7.47(2H,m), 7.54(1H,m), 7.72(1H,t)

EXAMPLE 80

¹H NMR(CDCl₃): δ1.52(3H,t), 2.44(3H,s), 3.13(4H,t), 3.89(4H,t), 4.61(2H,q), 7.15(4H,brs), 7.45(2H,m), 7.69(2H,brm)

EXAMPLE 81

¹H NMR(CDCl₃): δ1.44(3H,t), 3.22(4H,t), 3.38(3H,s), 3.71(4H,t), 3.78(6H,s), 4.53(2H,q), 6.09(1H,brs), 6.13(2H,brs), 7.50 (2H,m), 7.75(1H,m), 7.82(1H,m)

EXAMPLE 82

¹H NMR(CDCl₃): δ1.43(3H,t), 3.22(4H,t), 3.38(3H,s), 3.66(4H,t), 4.54(2H,q), 6.76(2H,s), 6.86(1H,s), 7.51(2H,m), 7.76(1H,m), 7.83(1H,m)

EXAMPLE 83

¹H NMR(CDCl₃): δ1.34(3H,t), 1.44(3H,t), 3.15(4H,t), 3.62(4H,t), 3.77(6H,s), 3.91(2H,q), 4.53(2H,q), 6.06(3H,brs), 7.51(2H,m), 7.75(1H,m), 7.81(1H,m)

EXAMPLE 84

¹H NMR(CDCl₃): δ1.33(3H,t), 1.44(3H,t), 3.16(4H,t), 3.59(4H,t), 3.91(2H,q), 4.54(2H,q), 6.74(2H,s), 6.85(1H,s), 7.52(2H,m), 7.76(1H,m), 7.82(1H,m)

EXAMPLE 85

¹H NMR(CDCl₃): δ1.34(3H,t), 1.45(3H,t), 2.28(6H,s), 3.15(4H,t), 3.63(4H,t), 3.91(2H,q), 4.53(2H,q), 6.56(3H,brs), 7.50(2H,m), 7.75(1H,d), 7.82(1H,d)

EXAMPLE 86

¹H NMR(CDCl₃): δ2.30(6H,s), 3.27(4H,t), 3.73(4H,t), 4.03(3H,s), 6.60(3H,brs), 7.13(1H,s), 7.33(2H,t), 7.45(1H,s), 7.67(1H,m), 7.75(1H,m)

EXAMPLE 87

¹H NMR(CDCl₃): δ3.20(4H,t), 3.40(4H,t), 3.75(6H,s), 3.99(3H,s), 6.10(3H,brs), 7.12(1H,s), 7.31(2H,t), 7.44(1H,s), 7.65(1H,m), 7.70(1H,m)

EXAMPLE 88

¹H NMR(CDCl₃): δ3.32(4H,t), 3.73(4H,t), 4.03(3H,s), 6.32(1H,t), 6.41(2H,d), 7.13(1H,s), 7.34(2H,t), 7.43(1H,s), 7.67(1H,m), 7.75(1H,m)

EXAMPLE 89

¹H NMR(CDCl₃): δ3.34(4H,t), 3.77(4H,t), 4.03(3H,s), 6.84(1H,m), 6.92(2H,m), 7.13(1H,s), 7.34(2H,m), 7.43(1H,s), 7.68(1H,m), 7.75(1H,m)

EXAMPLE 90

¹H NMR(CDCl₃): δ2.20(6H,s), 2.85(4H,t), 3.18(3H,s), 3.32(4H,t), 3.99(3H,s), 6.39(2H,s), 6.47(1H,s), 7.20(1H,s), 7.35(1H,t), 7.43(1H,t), 7.53(1H,s), 7.69(1H,d), 7.73(1H,d)

EXAMPLE 91

¹H NMR(CDCl₃): δ2.91(4H,t), 3.18(3H,s), 3.33(4H,t), 4.00(3H,s), 6.24(3H,brm), 7.21(1H,s), 7.37(1H,t), 7.45(1H,t), 7.53(1H,s), 7.70(1H,d), 7.74(1H,d)

EXAMPLE 92

¹H NMR(CDCl₃): δ3.03(4H,t), 3.18(3H,s), 3.52(4H,t), 4.01(3H,s), 6.82(3H,brm), 7.12(1H,brs), 7.37(1H,m), 7.46(1H,m), 7.56(1H,m), 7.72(2H,m)

EXAMPLE 93

¹H NMR(CDCl₃): δ2.88(4H,t), 3.18(3H,s), 3.33(4H,t), 3.71(6H,s), 3.99(3H,s), 5.92(2H,brs), 5.97(1H,brs), 7.20(1H,s), 7.36(1H,t), 7.43(1H,t), 7.52(1H,s), 7.69(1H,d), 7.73(1H,d)

EXAMPLE 94

¹H NMR(CDCl₃): δ1.34(3H,t), 2.21(6H,s), 2.88(4H,t), 3.32(4H,t), 3.91(2H,q), 3.99(3H,s), 6.39(2H,s), 6.47(1H,s), 7.20(1H,s), 7.35(1H,t), 7.46(1H,t), 7.56(1H,s), 7.71(1H,d), 7.73(1H,d)

EXAMPLE 95

¹H NMR(CDCl₃): δ1.35(3H,t), 2.90(4H,t), 3.33(4H,t), 3.70(6H,s), 3.92(2H,q), 3.99(3H,s), 5.92(2H,brs), 5.97(1H,brs), 7.25 (1H,s), 7.36(1H,t), 7.43(1H,t), 7.52(1H,s), 7.72(1H,d), 7.73(1H,d)

EXAMPLE 96

¹H NMR(CDCl₃): δ2.14(3H,s), 2.33(3H,s), 3.19(4H,s), 3.20(4H,s), 3.98(3H,s), 6.84(1H,s), 6.87(1H,t), 6.93(2H,d), 7.25(1H,d), 7.55(1H,s)

EXAMPLE 97

¹H NMR(CDCl₃): δ2.13(3H,s), 2.27(3H,s), 2.32(3H,s), 3.13(4H,d), 3.19(4H,d), 3.98(3H,s), 6.81(1H,s), 6.83(2H,d), 7.07(2H,d), 7.54(1H,s)

EXAMPLE 98

¹H NMR(CDCl₃): δ0.91(3H,t), 1.30(2H,m), 1.54(2H,m), 2.13(3H,s), 2.32(3H,s), 2.53(2H,t), 3.14(4H,d), 3.19(4H,d), 3.98(3H,s), 6.80(1H,s), 6.85(2H,d), 7.08(2H,d), 7.55(1H,s)

EXAMPLE 99

¹H NMR(CDCl₃): δ2.13(3H,s), 2.27(6H,s), 2.32(3H,s), 3.12(4H,s), 3.13(4H,s), 3.89(3H,s), 6.56(3H,s), 6.81(1H,s), 7.54(1H,s)

EXAMPLE 100

¹H NMR(CDCl₃): δ2.16(3H,s), 2.33(3H,s), 3.08(4H,t), 3.25(4H,t), 3.85(3H,s), 3.98(3H,s), 6.87(1H,t), 6.93(2H,d), 7.02(1H,m), 7.57(1H,s)

EXAMPLE 101

¹H NMR(CDCl₃): δ2.14(3H,s), 2.32(3H,s), 3.17(8H,s), 3.77(6H,s), 3.98(3H,s), 6.04(1H,s), 6.08(2H,s), 6.81(1H,s), 7.53(1H,s)

EXAMPLE 102

¹H NMR(CDCl₃): δ2.15(3H,s), 2.33(3H,s), 3.17(8H,s), 3.98(3H,s), 6.28(1H,t), 6.35(2H,d), 6.78(1H,s), 7.50(1H,s)

EXAMPLE 103

¹H NMR(CDCl₃): δ2.16(3H,s), 2.39(3H,s), 3.18(4H,s), 3.20(4H,s), 3.98(3H,s), 6.69(3H,s), 6.78(1H,s), 7.45(1H,s)

EXAMPLE 104

¹H NMR(CDCl₃): δ2.15(3H,s), 2.33(3H,s), 3.18(8H,s), 3.98(3H,s), 6.78(1H,s), 6.82(1H,d), 6.97(1H,d), 7.03(1H,s), 7.11(1H,t), 7.51(1H,s)

EXAMPLE 105

¹H NMR(CDCl₃): δ2.16(3H,s), 2.34(3H,s), 3.20(4H,s), 3.37(4H,s), 3.90(3H,s), 6.78(1H,s), 7.47(1H,s), 7.97(2H,s), 8.42(1H,s)

EXAMPLE 106

¹H NMR(CDCl₃); δ1.40(6H,t), 2.17(3H,s), 2.30(3H,s), 3.29(4H,s), 3.33(4H,s), 3.98(3H,s), 4.38(4H,q), 7.41(1H,s), 7.72(2H,s), 8.16(1H,s)

EXAMPLE 107

¹H NMR(CDCl₃): δ2.14(3H,s), 2.33(3H,s), 3.21(8H,s), 3.98(3H,s), 4.66(4H,s), 6.82(1H,s), 6.88(3H,s), 7.52(1H,s)

EXAMPLE 108

¹H NMR(CDCl₃): δ1.19(3H,t), 2.36(3H,s), 2.52(2H,q), 3.07(4H,s), 3.30(4H,s), 3.84(3H,s), 3.97(3H,s), 6.85-7.03 (5H,m), 7.51(1H,s)

EXAMPLE 109

¹H NMR(CDCl₃): δ1.14(3H,t), 2.36(3H,s), 2.50(2H,q), 3.17(8H,d), 3.77(6H,s), 3.98(3H,s), 6.04(1H,s), 6.07(2H,s), 6.80(1H,s), 7.56(1H,s)

EXAMPLE 110

¹H NMR(CDCl₃): δ1.22(6H,m), 2.36(3H,s), 2.54(2H,q), 2.68(2H,q), 2.90(4H,s), 3.20(4H,s), 3.98(3H,s), 6.80(1H,s), 7.08(2H,m), 7.17(1H,t), 7.22(1H,d), 7.62(1H,s)

EXAMPLE 111

¹H NMR(CDCl₃): δ1.14(3H,t), 2.36(3H,s), 2.50(2H,q), 3.18(4H,s), 3.25(4H,s), 3.98(3H,s), 6.89(4H,m), 7.27(2H,m), 7.52(1H,s)

EXAMPLE 112

¹H NMR(CDCl₃): δ1.20(3H,t), 2.36(3H,s), 2.38(3H,s), 2.54(2H,q), 3.00(4H,s), 3.27(4H,s), 3.97(3H,s), 7.00(1H,brs) 7.01(1H,s), 7.10(3H,s), 7.55(1H,s)

EXAMPLE 113

¹H NMR(CDCl₃): δ1.14(3H,t), 2.27(6H,s), 2.36(3H,s), 2.49(2H,q), 3.17(4H,s), 3.18(4H,s), 3.98(3H,s), 6.55(3H,s), 6.81(1H,s), 7.57(1H,s)

EXAMPLE 114

¹H NMR(CDCl₃): δ1.15(3H,t), 2.36(3H,s), 2.50(2H,q), 3.17(8H,s), 3.98(3H,s), 6.28(1H,t), 6.35(2H,d), 6.65(1H,brs), 6.78(1H,s), 7.52(1H,s)

EXAMPLE 115

¹H NMR(CDCl₃): δ1.15(3H,t), 2.36(3H,s), 2.50(2H,q), 3.17(8H,s), 3.98(3H,s), 6.17(1H,brs), 6.74(3H,m), 6.82(1H,s), 7.51(1H,s)

EXAMPLE 116

¹H NMR(CDCl₃): δ1.15(3H,t), 2.32(3H,s), 2.48(2H,q), 2.84(4H,s), 2.94(4H,s), 3.94(3H,s), 6.73(1H,s), 7.00(1H,s), 7.09(1H,t), 7.24(2H,m), 7.29(1H,t), 7.35(2H,t), 7.51(1H,s), 7.58(2H,d)

EXAMPLE 117

¹H NMR(CDCl₃): δ1.15(3H,t), 2.37(3H,s), 2.51(2H,q), 3.28(4H,s), 3.39(4H,s), 3.98(3H,s), 6.84(1H,brs), 7.47(1H,s), 7.96(2H,s), 8.42(1H,s)

EXAMPLE 118

¹H NMR(CDCl₃): δ2.69(3H,s), 3.20(8H,s), 3.77(6H,s), 3.80(3H,s), 4.06(3H,s), 6.04(1H,s), 6.09(2H,s), 6.93(1H,s), 8.39(1H,s)

EXAMPLE 119

¹H NMR(CDCl₃): δ2.28(6H,s), 2.70(3H,s), 3.20(8H,s), 3.80(3H,s), 4.06(3H,s), 6.56(3H,s), 6.94(1H,s), 8.40(1H,s)

EXAMPLE 120

¹H NMR(CDCl₃): δ2.69(3H,s), 3.19(4H,d), 3.22(4H,d), 3.80(3H,s), 4.07(3H,s), 6.29(1H,t), 6.36(2H,d), 6.75(1H,brs), 6.93(1H,s), 8.36(1H,s)

EXAMPLE 121

¹H NMR(CDCl₃): δ2.70(3H,s), 3.13(4H,s), 3.28(4H,s), 3.83(3H,s), 3.86(3H,s), 4.06(3H,s), 6.94(5H,m), 8.42(1H,s)

EXAMPLE 122

¹H NMR(CDCl₃): δ2.70(3H,s), 3.23(8H,s), 3.78(3H,s), 4.07(3H,s), 6.89(1H,t), 6.94(2H,d), 6.99(1H,brs), 7.27(2H,d), 8.38(1H,s)

EXAMPLE 123

$^1$H NMR(CDCl$_3$): δ2.27(3H,s), 2.69(3H,s), 3.17(4H,d), 3.22(4H,d), 3.78(3H,s), 4.06(3H,s), 6.84(2H,d), 6.98(1H, brs), 7.09(1H,d), 8.38(1H,s)

EXAMPLE 124

$^1$H NMR(CDCl$_3$): δ2.70(3H,s), 3.22(8H,s), 3.80(3H,s), 4.06(3H,s), 6.78(1H,d), 6.84(1H,d), 6.88(1 H,s), 6.98(1H, brs), 7.17(1H,t), 8.35(1H,s)

EXAMPLE 125

$^1$H NMR(CDCl$_3$): δ2.39(3H,s), 3.17(8H,s), 3.76(6H,s), 4.00(3H,s), 4.59(2H,s), 6.03(1H,s), 6.07(2H,d), 6.88(1H,s), 7.79(1H,s)

EXAMPLE 126

$^1$H NMR(CDCl$_3$): δ2.27(6H,s), 2.40(3H,s), 3.18(8H,s), 4.01(3H,s), 4.59(2H,s), 6.55(3H,s), 6.87(1H,s), 7.80(2H,s)

EXAMPLE 127

$^1$H NMR(CDCl$_3$): δ2.40(3H,s), 3.19(8H,s), 4.00(3H,s), 4.61(2H,s), 6.27(1H,t), 6.35(2H,d), 6.86(1H,s), 7.79(1H,s)

EXAMPLE 128

$^1$H NMR(CDCl$_3$): δ2.40(3H,s), 3.08(4H,s), 3.31(4H,s), 3.84(3H,s), 3.99(3H,s), 4.61(2H,s), 6.92(5H,m), 7.77(1H,s)

EXAMPLE 129

$^1$H NMR(CDCl$_3$): δ2.39(3H,s), 3.20(8H,d), 4.00(3H,s), 4.58(2H,s), 6.90(4H,m), 7.27(2H,d), 7.79(1H,s)

EXAMPLE 130

$^1$H NMR(CDCl$_3$): δ2.17(3H,s), 2.39(3H,s), 3.13(4H,d), 3.22(4H,d), 3.99(3H,s), 4.58(2H,s), 6.82(2H,d), 7.00(1H, brs), 7.06(2H,d), 7.78(1H,s)

EXAMPLE 131

$^1$H NMR(CDCl$_3$): δ2.39(3H,s), 3.19(8H,d), 4.00(3H,s), 4.60(2H,s), 6.76(1H,d), 6.82(1H,d), 6.85(1H,s), 6.95(1H, brs), 7.16(1H,t), 7.77(1H,s)

EXAMPLE 132

$^1$H NMR(CDCl$_3$): δ2.27(6H,s), 2.50(3H,s), 2.64(3H,s), 3.19(8H,d), 4.07(3H,s), 6.55(2H,s), 6.56(1H,s), 6.88(1H,s), 7.39(1H,brs), 8.19(1H,s)

EXAMPLE 133

$^1$H NMR(CDCl$_3$): δ2.50(3H,s), 2.64(3H,s), 3.16(4H,s), 3.25(4H,s), 3.76(6H,s), 4.06(3H,s), 6.05(1H,s), 6.07(2H,s), 7.05(1H,brs), 8.13(1H,s)

EXAMPLE 134

$^1$H NMR(CDCl$_3$): δ2.50(3H,s), 2.65(3H,s), 3.20(4H,s), 3.26(4H,s), 4.06(3H,s), 6.91(4H,m), 7.27(2H,m), 8.15(1H,s)

EXAMPLE 135

$^1$H NMR(CDCl$_3$): δ2.18(3H,s), 2.42(3H,s), 2.57(3H,s), 3.15(4H,s), 3.30(4H,s), 4.07(3H,s), 6.84(2H,d), 7.07(3H,d), 8.13(1H,s)

EXAMPLE 136

$^1$H NMR(CDCl$_3$): δ2.52(3H,s), 2.66(3H,s), 3.22(4H,s), 3.28(4H,s), 4.07(3H,s), 6.30(3H,m), 8.07(1H,s)

EXAMPLE 137

$^1$H NMR(CDCl$_3$): δ2.39(3H,s), 2.58(3H,s), 2.66(3H,s), 3.04(4H,s), 3.33(4H,s), 4.07(3H,s), 7.02(1H,d), 7.10(3H,s), 8.14(1H,s)

EXAMPLE 138

$^1$H NMR(CDCl$_3$): δ1.40(3H,d), 2.26(6H,s), 2.39(3H,s), 3.19(8H,s), 3.99(3H,s), 5.04(1H,q), 6.54(3H,s), 6.86(1H,s), 7.93(1H,s)

EXAMPLE 139

$^1$H NMR(CDCl$_3$) δ1.40(3H,d), 2.39(3H,s), 3.20(8H,m), 3.76(6H,s), 3.99(3H,s), 5.03(1H,q), 6.03(1H,s), 6.06(2H,s), 7.04(1H,brs), 7.89(1H,s)

EXAMPLE 140

$^1$H NMR(CDCl$_3$): δ1.40(3H,d), 2.39(3H,s), 3.19(4H,m), 3.30(4H,s), 3.97(3H,s), 5.08(1H,q), 6.89(3H,m), 7.24(2H,m), 7.87(1H,s)

EXAMPLE 141

$^1$H NMR(CDCl$_3$): δ1.40(3H,d), 2.26(3H,s), 2.39(3H,s), 3.15(4H,s), 3.35(4H,s), 3.97(3H,s), 5.02(1H,q), 6.82(2H,d), 7.06(2H,d), 7.84(1H,s)

EXAMPLE 142

$^1$H NMR(CDCl$_3$): δ1.40(3H,d), 2.39(3H,s), 3.20(4H,m), 3.28(4H,s), 3.98(3H,s), 5.04(1H,q), 6.27(3H,m), 7.85(1H,s)

EXAMPLE 143

$^1$H NMR(CDCl$_3$): δ1.45(3H,d), 2.38(3H,s), 2.39(3H,s), 3.02(4H,m), 3.31(4H,s), 3.98(3H,s), 5.07(1H,q), 7.03(1H, brs), 7.09(4H,s), 7.91(1H,s)

EXAMPLE 144

$^1$H NMR(CDCl$_3$): δ2.18(3H,s), 2.27(6H,s), 2.41(3H,s), 3.19(4H,brs), 3.22(4H,brs), 4.00(3H,s), 6.55(2H,s), 6.56(1H,s), 7.50 (1H,s)

EXAMPLE 145

$^1$H NMR(CDCl$_3$): δ2.18(3H,s), 2.41(3H,s), 3.16(4H,brs), 3.25(4H,s), 3.76(6H,s), 4.00(3H,s), 6.05(1H,s), 6.03(2H,s), 7.49(1H,s)

EXAMPLE 146

$^1$H NMR(CDCl$_3$): δ2.18(3H,s), 2.40(3H,s), 3.18(4H,brs), 3.27(4H,brs), 4.00(3H,s), 6.27(3H,m), 7.50(1H,s)

EXAMPLE 147

$^1$H NMR(CDCl$_3$): δ2.18(3H,s), 2.39(3H,s), 2.40(3H,s), 3.04(4H,s), 3.33(4H,s), 4.01(3H,s), 7.02(1H,d), 7.10(3H,s), 7.50(4H,s)

EXAMPLE 148

$^1$H NMR(CDCl$_3$): δ2.10(3H,s), 2.31(3H,s), 3.20(4H,s), 3.37(4H,s), 3.95(3H,s), 7.42(1H,s), 7.96(2H,s), 8.40(1H,s)

EXAMPLE 149

$^1$H NMR(CDCl$_3$): δ2.09(3H,s), 2.26(3H,s), 2.31(3H,s), 3.11(4H,brs), 3.25(4H,brs), 4.00(3H,s), 6.80(2H,d), 7.06(2H,d), 7.42 (1H,s)

EXAMPLE 150

¹H NMR(CDCl₃): δ1.74(3H,d), 2.28(9H,s), 3.12(2H,brs), 3.27(4H,brs), 3.65(4H,brs), 4.02(3H,s), 4.15(1H,q), 6.54(3H,s), 8.37 (1H,s)

EXAMPLE 151

¹H NMR(CDCl₃): δ1.74(3H,d), 2.28(3H,s), 3.05(2H,brs), 3.26(4H,m), 3.67(4H,m), 3.82(6H,s), 4.01(3H,s), 4.15(1H,q), 6.06(1H,s), 6.09(2H,s), 8.37(1H,s)

EXAMPLE 152

¹H NMR(CDCl₃): δ1.74(3H,d), 2.28(3H,s), 3.15(2H,brs), 3.22(4H,s), 3.29(4H,s), 4.00(3H,s), 4.15(1H,q), 6.30(3H,m), 8.37(1H,s)

EXAMPLE 153

¹H NMR(CDCl₃): δ1.74(3H,d), 2.28(3H,s), 2.39(3H,s), 3.10(2H,brs), 3.04(4H,s), 3.34(4H,s), 4.07(3H,s), 4.15(1H,q), 7.02(1H,d), 7.10(3H,s), 8.37(1H,s)

EXAMPLE 154

¹H NMR(CDCl₃): δ1.74(3H,d), 2.28(3H,s), 3.07(2H,brs), 3.20(4H,s), 3.35(4H,s), 3.90(3H,s), 4.15(1H,q), 7.97(2H,s), 8.35(1H,s), 8.42(1H,s)

EXAMPLE 155

¹H NMR(CDCl₃): δ1.74(3H,d), 2.28(3H,s), 3.11(2H,brs), 3.20(8H,s), 4.00(3H,s), 4.15(1H,q), 6.17(1H,s), 6.74(2H,m), 8.37(1H,s)

EXAMPLE 156

¹H NMR(CDCl₃): δ1.26(3H,t), 2.28(3H,s), 3.08(2H,q), 3.17(4H,s), 3.24(4H,s), 3.78(3H,s), 4.07(3H,s), 6.85(2H,d), 7.00(1H,brs), 7.07(2H,d), 8.05(1H,s)

EXAMPLE 157

¹H NMR(CDCl₃): δ1.25(6H,m), 2.70(2H,q), 2.95(4H,t), 3.08(2H,q), 3.26(4H,brs), 3.90(3H,s), 4.07(3H,s), 7.08(2H,m), 7.18(1H,t), 7.24(1H,d), 8.40(1H,s)

EXAMPLE 158

¹H NMR(CDCl₃): δ1.26(3H,t), 2.27(6H,s), 3.08(2H,q), 3.20(8H,s), 3.79(3H,s), 4.07(3H,s), 4.22(3H,s), 6.56(1H,s), 6.57(2H,s), 6.94(1H,s), 8.38(1H,s)

EXAMPLE 159

¹H NMR(CDCl₃): δ1.26(3H,t), 3.07(2H,q), 3.21(8H,s), 3.77(6H,s), 3.79(3H,s), 4.07(3H,s), 6.05(1H,s), 6.09(2H,s), 6.95(1H,s), 8.37(1H,s)

EXAMPLE 160

¹H NMR(CDCl₃): δ1.27(3H,t), 3.07(2H,q), 3.24(8H,s), 3.81(3H,s), 4.08(3H,s), 6.75(2H,d), 6.83(2H,s), 7.05(1H,brs), 8.29 (1H,s)

EXAMPLE 161

¹H NMR(CDCl₃): δ1.27(3H,t), 2.40(3H,s), 3.07(6H,m), 3.28(4H,brs), 3.88(3H,s), 4.07(3H,s), 7.05(2H,m), 7.12(3H,m), 8.38 (1H,s)

EXAMPLE 162

¹H NMR(CDCl₃): δ1.27(3H,t), 1.40(6H,t), 3.07(2H,q), 3.26(4H,s), 3.34(4H,s), 3.77(3H,s), 4.08(3H,s), 4.39(4H,q), 7.00(1H,brs), 7.70(2H,s), 8.17(1H,s), 8.35(1H,s)

EXAMPLE 163

¹H NMR(CDCl₃): δ1.27(3H,t), 3.07(2H,q), 3.22(8H,d), 3.80(3H,s), 4.08(3H,s), 6.29(1H,t), 6.36(2H,d), 6.99(1H,brs), 8.32(1H,s)

EXAMPLE 164

¹H NMR(CDCl₃): δ1.25(3H,t), 2.27(3H,s), 2.69(2H,q), 3.14(4H,d), 3.22(4H,d), 4.01(3H,s), 4.60(2H,s), 6.82(2H,d), 6.96(1H,brs), 7.06(2H,d), 7.78(1H,s)

EXAMPLE 165

¹H NMR(CDCl₃): δ1.21(3H,t), 1.26(3H,t), 2.67(4H,m), 2.91(4H,t), 3.27(4H,s), 4.01(3H,s), 4.66(2H,s), 7.06(2H,m), 7.16(1H,t), 7.21(1H,d), 7.82(1H,s)

EXAMPLE 166

¹H NMR(CDCl₃): δ1.26(3H,t), 2.27(6H,s), 2.69(2H,q), 3.19(8H,d), 4.02(3H,s), 4.60(2H,s), 6.55(3H,s), 6.90(1H,s), 7.80(1H,s)

EXAMPLE 167

¹H NMR(CDCl₃): δ1.26(3H,t), 2.69(2H,q), 3.19(8H,s), 3.76(6H,s), 4.02(3H,s), 4.60(2H,s), 6.03(1H,s), 6.08(2H,d), 6.88(1H,s), 7.79(1H,s)

EXAMPLE 168

¹H NMR(CDCl₃): δ1.26(3H,t), 2.69(2H,q), 3.20(8H,s), 4.01(3H,s), 4.62(2H,s), 6.73(2H,s), 6.84(1H,s), 6.95(1H,brs), 7.77(1H,s)

EXAMPLE 169

¹H NMR(CDCl₃): δ1.26(3H,t), 2.39(3H,s), 2.70(2H,q), 3.03(4H,d), 3.28(4H,s), 4.01(3H,s), 4.65(2H,s), 7.03(2H,m), 7.10(3H,m), 7.80(1H,s)

EXAMPLE 170

¹H NMR(CDCl₃): δ1.20(3H,t), 2.61(2H,q), 3.09(4H,s), 3.23(4H,s), 3.97(3H,s), 4.45(4H,s), 4.46(2H,s), 6.77(1H,s), 6.81(2H,s), 6.99(1H,brs), 7.90(1H,s)

EXAMPLE 171

¹H NMR(CDCl₃): δ1.25(3H,t), 2.68(2H,q), 3.21(4H,s), 3.22(4H,s), 4.01(3H,s), 4.62(2H,s), 6.27(1H,t), 6.33(2H,d), 7.05(1H,brs), 7.76(1H,s)

EXAMPLE 172

¹H NMR(CDCl₃): δ3.24(8H,s), 3.76(6H,s), 4.15(3H,s), 6.00(1H,s), 6.08(2H,d), 7.31(1H,t), 7.35(1H,s), 7.43(1H,t), 7.57(1H,d), 7.71(1H,d), 8.06(1H,s)

EXAMPLE 173

¹H NMR(CDCl₃): δ2.28(6H,s), 3.25(4H,s), 3.26(4H,s), 4.18(3H,s), 6.33(1H,brs), 6.56(1H,s), 6.58(2H,d), 7.33(1H,t), 7.47 (1H,t), 7.57(1H,d), 7.78(1H,d), 8.05(1H,s)

EXAMPLE 174

¹H NMR(CDCl₃): δ3.26(8H,s), 4.18(3H,s), 6.29(1H,t), 6.36(2H,d), 7.25(1H,brs), 7.34(1H,t), 7.49(1H,t), 7.50(1H,d), 7.79 (1H,d), 8.02(1H,s)

EXAMPLE 175

¹H NMR(CDCl₃): δ3.16(4H,s), 3.36(4H,s), 3.84(3H,s), 4.18(3H,s), 6.86(1H,d), 6.95(2H,m), 7.02(1H,m), 7.34(1H,t), 7.48(1H,t), 7.60(1H,d), 7.78(1H,d), 8.04(1H,s)

EXAMPLE 176

¹H NMR(CDCl₃): δ3.25(4H,d), 3.32(4H,s), 4.18(3H,s), 6.77(1H,d), 6.85(2H,m), 7.17(1H,t), 7.35(1H,t), 7.50(1H,t), 7.59(1H,d), 7.79(1H,d), 7.99(1H,s)

EXAMPLE 177

¹H NMR(CDCl₃): δ2.14(3H,s), 2.20(3H,s), 3.18(4H,d), 3.23(4H,d), 3.84(3H,s), 6.65(1H,s), 6.87(1H,t), 6.91(2H,d), 6.93(1H,brs), 7.25(2H,m), 7.36(1H,s)

EXAMPLE 178

¹H NMR(CDCl₃): δ2.14(3H,s), 2.20(3H,s), 2.27(3H,s), 3.12(4H,d), 3.22(4H,d), 3.84(3H,s), 6.64(1H,s), 6.83(2H,d), 6.96(1H,brs), 7.07(2H,d), 7.35(1H,s)

EXAMPLE 179

¹H NMR(CDCl₃): δ1.21(3H,t), 2.20(3H,s), 2.21(3H,s), 2.67(2H,q), 2.90(4H,t), 3.26(4H,s), 3.85(3H,s), 6.65(1H,s), 7.07(3H,m), 7.17(1H,t), 7.21(1H,d), 7.36(1H,s)

EXAMPLE 180

¹H NMR(CDCl₃): δ2.14(3H,s), 2.20(3H,s), 2.27(6H,s), 3.16(4H,d), 3.20(4H,d), 3.85(3H,s), 6.54(1H,s), 6.56(2H,s), 6.64(1H,s), 6.89(1H,brs), 7.37(1H,s)

EXAMPLE 181

¹H NMR(CDCl₃): δ2.14(3H,s), 2.20(3H,s), 3.17(4H,s), 3.19(4H,s), 3.77(6H,s), 3.85(3H,s), 6.03(1H,s), 6.08(2H,d), 6.64(1H,s), 6.90(1H,brs), 7.36(1H,s)

EXAMPLE 182

¹H NMR(CDCl₃): δ2.14(3H,s), 2.20(3H,s), 3.22(8H,s), 3.85(3H,s), 6.28(1H,t), 6.36(2H,d), 6.64(1H,s), 6.89(1H,brs), 7.36(1H,s)

EXAMPLE 183

¹H NMR(CDCl₃): δ2.15(3H,s), 2.20(3H,s), 3.17(4H,d), 3.21(4H,d), 3.85(3H,s), 6.65(1H,s), 6.78(1H,d), 6.81(1H,d), 6.86(1H,s), 6.94(1H,brs), 7.16(1H,t), 7.33(1H,s)

EXAMPLE 184

¹H NMR(CDCl₃): δ2.15(3H,s), 2.20(3H,s), 3.17(4H,d), 3.21(4H,d), 3.85(3H,s), 6.65(1H,s), 6.81(1H,d), 6.96(2H,brd), 7.02 (1H,s), 7.10(1H,t), 7.33(1H,s)

EXAMPLE 185

¹H NMR(CDCl₃): δ2.19(3H,s), 2.21(3H,s), 2.39(3H,s), 3.00(4H,d), 3.28(4H,s), 3.85(3H,s), 6.64(1H,s), 6.99(1H,brs), 7.03 (1H,d), 7.10(3H,m), 7.36(1H,s)

EXAMPLE 186

¹H NMR(CDCl₃): δ2.14(3H,s), 2.33(3H,s), 3.19(4H,s), 3.20(4H,s), 3.78(3H,s), 3.98(3H,s), 6.84(1H,s), 6.87(1H,t), 6.93(2H,m), 7.24(1H,d), 7.56(1H,s)

EXAMPLE 187

¹H NMR(CDCl₃): δ2.13(3H,s), 2.27(3H,s), 2.32(3H,s), 3.13(4H,d), 3.19(4H,d), 3.77(3H,s), 3.98(3H,s), 6.81(1H,s), 6.83(2H,d), 7.07(2H,d), 7.54(1H,s)

EXAMPLE 188

¹H NMR(CDCl₃): δ2.13(3H,s), 2.28(9H,s), 3.17(4H,brs), 3.78(3H,s), 3.98(3H,s), 6.56(3H,s), 6.70(1H,s), 7.53(1H,s)

EXAMPLE 189

¹H NMR(CDCl₃): δ2.14(3H,s), 2.32(3H,s), 3.17(8H,s), 3.77(9H,s), 3.98(3H,s), 6.04(1H,s), 6.08(2H,s), 6.81(1H,s), 7.53(1H,s)

EXAMPLE 190

¹H NMR(CDCl₃): δ2.15(3H,s), 2.33(3H,s), 3.17(8H,s), 3.78(3H,s), 3.98(3H,s), 6.28(1H,t), 6.35(2H,d), 6.78(1H,s), 7.50(1H,s)

EXAMPLE 191

¹H NMR(CDCl₃): δ2.15(3H,s), 2.34(3H,s), 2.38(3H,s), 3.00(4H,s), 3.28(4H,s), 3.78(3H,s), 3.90(3H,s), 7.01(1H,s), 7.10(3H,s), 7.55(1H,s)

EXAMPLE 192

¹H NMR(CDCl₃): δ2.16(3H,s), 2.34(3H,s), 3.20(4H,s), 3.37(4H,s), 3.78(3H,s), 3.90(3H,s), 6.78(1H,s), 7.47(1H,s), 7.97(2H,s), 8.42(1H,s)

EXAMPLE 193

¹H NMR(CDCl₃): δ1.15(3H,t), 2.37(3H,s), 2.50(2H,q), 3.18(4H,brs), 3.23(4H,brs), 3.82(3H,s), 3.97(3H,s), 6.72(2H,s), 6.88 (1H,s), 7.45(1H,s)

EXAMPLE 194

¹H NMR(CDCl₃): δ1.26(3H,t), 3.07(2H,q), 3.22(8H,s), 3.79(3H,s), 3.86(3H,s), 4.07(3H,s), 6.29(1H,t), 6.36(2H,d), 8.29(1H,s)

EXAMPLE 195

¹H NMR(CDCl₃): δ1.26(3H,t), 1.40(6H,t), 3.06(2H,q), 3.27(4H,brs), 3.38(4H,brs), 3.77(3H,s), 3.81(3H,s), 4.07(3H,s), 4.38 (4H,q), 7.76(2H,s), 8.17(1H,s), 8.30(1H,s)

EXAMPLE 196

¹H NMR(CDCl₃): δ1.24(3H,t), 2.67(2H,q), 3.21(8H,s), 3.78(3H,s), 4.01(3H,s), 4.59(2H,s), 4.63(4H,s), 6.84(2H,m), 6.88(2H,s), 7.78(1H,s)

EXAMPLE 197

¹H NMR(CDCl₃): δ2.14(3H,s), 2.20(3H,s), 2.27(3H,s), 3.13(4H,brs), 3.24(4H,brs), 3.78(3H,s), 3.84(3H,s), 6.64 (1H,s), 6.84 (2H,brs), 7.07(2H,d), 7.27(1H,brs)

EXAMPLE 198

¹H NMR(CDCl₃): δ2.14(3H,s), 2.20(3H,s), 2.25(6H,s), 3.16(4H,brs), 3.22(4H,brs), 3.79(3H,s), 3.83(3H,s), 6.54 (2H,s), 6.64 (1H,s), 6.81(1H,brs), 7.27(1H,brs)

EXAMPLE 199

¹H NMR(CDCl₃): δ2.11(3H,brs), 2.16(3H,s), 2.36(3H,s), 3.24(4H,t), 3.80(4H,s), 3.92(3H,s), 6.85(1H,brs), 6.89(1H,t), 6.95(2H,d), 7.28(2H,t)

EXAMPLE 200

¹H NMR(CDCl₃): δ2.11(3H,brs), 2.16(3H,s), 2.28(3H,s), 2.36(3H,s), 3.19(4H,t), 3.80(4H,brs), 3.92(3H,s), 6.86(3H,brd), 7.08 (2H,d)

EXAMPLE 201

¹H NMR(CDCl₃): δ0.92(3H,t), 1.35(2H,m), 1.55(2H,m), 2.10(3H,brs), 2.16(3H,s), 2.36(3H,s), 2.54(2H,t), 3.20(4H,t), 3.80 (4H,brs), 3.92(3H,s), 6.87(3H,brd), 7.09(2H,d)

EXAMPLE 202

$^1$H NMR(CDCl$_3$): δ2.10(3H,brs), 2.16(3H,s), 2.89(6H,s), 2.36(3H,s), 3.21(4H,t), 3.78(4H,brs), 3.92(3H,s), 6.56(1H,s), 6.59 (2H,s), 6.84(3H,brs)

EXAMPLE 203

$^1$H NMR(CDCl$_3$): δ2.10(3H,brs), 2.16(3H,s), 2.36(3H,s), 3.22(4H,t), 3.79(7H,brs), 3.92(3H,s), 6.84(1H,brs), 6.95(4H,s)

EXAMPLE 204

$^1$H NMR(CDCl$_3$): δ2.10(3H,brs), 2.16(3H,s), 2.36(3H,s), 3.24(4H,brs), 3.78(1OH,s), 3.92(3H,s), 6.05(1H,s), 6.11(2H,s), 6.84 (3H,brs)

EXAMPLE 205

$^1$H NMR(CDCl$_3$): δ2.10(3H,brs), 2.16(3H,s), 2.36(3H,s), 3.24(4H,t), 3.78(4H,t), 6.28(1H,t), 6.39(2H,d), 6.84(1H,s)

EXAMPLE 206

$^1$H NMR(CDCl$_3$): δ2.10(3H,s), 2.16(3H,s), 2.36(3H,s), 3.25(4H,t), 3.78(4H,t), 3.92(3H,s), 6.77(2H,s), 6.84(2H,s)

EXAMPLE 207

$^1$H NMR(CDCl$_3$): δ2.10(3H,brs), 2.17(3H,s), 2.36(3H,s), 3.25(4H,brs), 3.79(4H,brs), 3.92(3H,s), 6.84(2H,m), 7.00 (1H,d), 7.06 (1H,brs), 7.13(1H,t)

EXAMPLE 208

$^1$H NMR(CDCl$_3$): δ2.12(3H,s), 2.17(3H,s), 2.37(3H,s), 3.50(4H,t), 3.88(4H,brs), 3.93(3H,s), 6.87(1H,brs), 8.00 (2H,d), 8.43 (1H,s)

EXAMPLE 209

$^1$H NMR(CDCl$_3$): δ1.41(6H,t), 2.11(3H,s), 2.15(3H,s), 2.37(3H,s), 3.36(4H,brs), 3.83(4H,brs), 3.92(3H,s), 4.40 (4H,q), 6.85 (1H,brs), 7.78(2H,s), 8.18(1H,s)

EXAMPLE 210

$^1$H NMR(CDCl$_3$): δ1.67(3H,t), 2.10(3H,s), 2.39(3H,s), 2.51(2H,q), 3.25(4H,t), 3.80(4H,t), 3.92(3H,s), 6.90(2H,t), 6.95(2H,d), 7.29(2H,t)

EXAMPLE 211

$^1$H NMR(CDCl$_3$): δ1.17(3H,t), 2.10(3H,brs), 2.39(3H,s), 2.52(2H,q), 3.13(4H,brs), 3.84(4H,brs), 3.88(3H,s), 3.93 (3H,s), 6.89 (2H,brd), 6.93(2H,m), 7.04(1H,m)

EXAMPLE 212

$^1$H NMR(CDCl$_3$): δ1.16(3H,t), 2.09(3H,s), 2.39(3H,s), 2.51(2H,q), 3.23(4H,t), 3.79(10H,s), 3.92(3H,s), 6.05(1H,s), 6.11(2H,d), 6.87(1H,s)

EXAMPLE 213

$^1$H NMR(CDCl$_3$): δ1.18(3H,t), 1.25(3H,t), 2.11(3H,brs), 2.40(3H,s), 2.52(2H,q), 2.72(2H,q), 2.96(4H,brs), 3.79(4H,brs), 3.94 (3H,s), 6.88(1H,brs), 7.09(2H,m), 7.18(1H,t), 7.24(1H,d)

EXAMPLE 214

$^1$H NMR(CDCl$_3$): δ1.16(3H,t), 2.09(3H,s), 2.29(6 H,s), 2.39(3 H,s), 2.51(2 H,q), 3.22(4 H,t), 3.78(4 H,t), 3.92(3H,s), 6.56(1H,s), 6.59(2H,s), 6.87(1H,s)

EXAMPLE 215

$^1$H NMR(CDCl$_3$): δ1.16(3H,t), 2.11(3H,brs), 2.40(3H,s), 2.51(2H,q), 3.27(4H,s), 3.80(4H,s), 3.92(3H,s), 6.28(1H,t), 6.39(2H,d), 6.84(1H,s)

EXAMPLE 216

$^1$H NMR(CDCl$_3$): δ1.17(3H,t), 2.12(3H,brs), 2.40(3H,s), 2.52(2H,q), 3.27(4H,s), 3.80(4H,s), 3.92(3H,s), 6.77(2H,d), 6.84(1H,s), 6.90(1H,brs)

EXAMPLE 217

$^1$H NMR(CDCl$_3$): δ1.15(3H,t), 2.03(3H,brs), 2.38(3H,s), 2.50(2H,q), 2.90(4H,brs), 3.51(4H,brs), 3.90(3H,s), 6.82 (1H,d), 7.03 (1H,d), 7.10(1H,t), 7.27(3H,m), 7.39(2H,t), 7.61(2H,d)

EXAMPLE 218

$^1$H NMR(CDCl$_3$): δ1.15(3H,t), 2.13(3H,brs), 2.41(3H,s), 2.52(2H,q), 3.52(4H,brs), 3.93(7H,s), 6.87(1H,brs), 7.99 (2H,d), 8.44 (1H,s)

EXAMPLE 219

$^1$H NMR(CDCl$_3$): δ1.17(3H,t), 2.10(3H,brs), 2.39(3H,s), 2.42(3H,s), 2.52(2H,q), 3.06(4H,s), 3.83(4H,s), 3.93(3H,s), 6.88(1H,brs), 7.05(1H,m), 7.12(3H,s)

EXAMPLE 220

$^1$H NMR(CDCl$_3$): δ2.10(3H,brs), 2.73(3H,s), 3.23(4H, brs), 3.86(10H,s), 3.89(3H,s), 6.05(1H,s), 6.11(2H,s), 7.62 (1H,brs)

EXAMPLE 221

$^1$H NMR(CDCl$_3$) δ2.10(3H,brs), 2.29(6H,s), 2.73(3H,s), 3.23(4H,brs), 3.82(4H,brs), 3.86(3H,s), 3.99(3H,s), 6.57 (3H,m), 7.62 (1H,brs)

EXAMPLE 222

$^1$H NMR(CDCl$_3$): δ2.10(3H,s), 2.73(3H,s), 3.27(4H,t), 3.83(4H,s), 3.86(3H,s), 4.00(3H,s), 6.30(1H,t), 6.40(2H,d), 7.64(1H,brs)

EXAMPLE 223

$^1$H NMR(CDCl$_3$): δ2.10(3H,brs), 2.73(3H,s), 3.14(4H, brs), 3.86(7H,s), 3.89(3H,s), 4.00(3H,s), 6.89(1H,d), 6.95 (2H,m), 7.04(1H,brm), 7.62(1H,brs)

EXAMPLE 224

$^1$H NMR(CDCl$_3$): δ2.11(3H,brs), 2.73(3H,s), 3.26(4H,t), 3.85(7H,s), 4.00(3H,s), 6.91(1H,t), 6.95(2H,d), 7.30(2H,t), 7.63(1H,brs)

EXAMPLE 225

$^1$H NMR(CDCl$_3$): δ2.10(3H,s), 2.27(3H,s), 2.72(3H,s), 3.20(4H,t), 3.83(4H,s), 3.85(3H,s), 4.00(3H,s), 6.87(2H,d), 7.09(3H,d), 7.63(1H,brs)

EXAMPLE 226

$^1$H NMR(CDCl$_3$): δ2.11(3H,brs), 2.73(3H,s), 3.27(4H, brs), 3.86(7H,s), 4.00(3H,s), 6.81(1H,d), 6.85(1H,d), 6.90 (1H,s), 7.19(1H,t), 7.63(1H,brs)

EXAMPLE 227

$^1$H NMR(CDCl$_3$): δ2.12(3H,brs), 2.29(6H,s), 2.53(3H,s), 2.67(3H,s), 3.24(4H,brs), 3.83(4H,brs), 4.00(3H,s), 6.58 (1H,s), 6.60 (2H,s), 7.47(1H,brs)

EXAMPLE 228

$^1$H NMR(CDCl$_3$): δ2.12(3H,brs), 2.53(3H,s), 2.68(3H,s), 3.25(4H,t), 3.79(6H,s), 3.82(4H,brs), 4.00(3H,s), 6.06(1H,s), 6.12(2H,d), 7.46(1H,brs)

EXAMPLE 229

$^1$H NMR(CDCl$_3$): δ2.12(3H,s), 2.53(3H,s), 2.68(3H,s), 3.26(4H,t), 3.77(4H,t), 4.00(3H,s), 6.89(3H,d), 7.19(2H,d), 7.46(1H,s)

EXAMPLE 230

$^1$H NMR(CDCl$_3$): δ2.12(3H,brs), 2.12(3H,s), 2.53(3H,s), 2.68(3H,s), 3.22(4H,s), 3.85(3H,brs), 4.00(3H,s), 6.87(2H,d), 7.10 (2H,d), 7.45(1H,s)

EXAMPLE 231

$^1$H NMR(CDCl$_3$): δ2.12(3H,s), 2.55(3H,s), 2.68(3H,s), 3.32(4H,brs), 3.86(4H,brs), 4.01(3H,s), 6.38(3H,m), 7.47 (1H,brs)

EXAMPLE 232

$^1$H NMR(CDCl$_3$): δ2.12(3H,s), 2.43(3H,s), 2.54(3H,s), 2.68(3H,s), 3.07(4H,brs), 3.86(4H,brs), 4.00(3H,s), 7.06 (1H,m), 7.13 (3H,m), 7.46(1H,brs)

EXAMPLE 233

$^1$H NMR(CDCl$_3$) δ1.28(3H,t), 2.13(3H,brs), 2.29(3H,s), 3.11(2H,q), 3.21(4H,brs), 3.85(7H,brs), 4.00(3H,s), 6.89 (2H,brs), 7.08 (2H,d), 7.62(1H,brs)

EXAMPLE 234

$^1$H NMR(CDCl$_3$): δ1.24(3H,t), 1.28(3H,t), 2.12(3H,brs), 2.72(2H,q), 2.96(4H,brs), 3.10(2H,q), 3.81(4H,brs), 3.86 (3H,s), 4.00 (3H,s), 7.09(2H,m), 7.19(1H,t), 7.24(1H,d), 7.60(1H,brs)

EXAMPLE 235

$^1$H NMR(CDCl$_3$): δ1.28(3H,t), 2.10(3H,brs), 2.29(6H,s), 3.11(2H,q), 3.23(4H,brs), 3.82(4H,brs), 3.85(3H,s), 4.00 (3H,s), 6.57 (1H,s), 6.59(2H,s), 7.59(1H,brs)

EXAMPLE 236

$^1$H NMR(CDCl$_3$): δ1.28(3H,t), 2.10(3H,brs), 3.10(2H,q), 3.24(4H,brs), 3.79(6H,s), 3.81(4H,brs), 3.85(3H,s), 4.00 (3H,s), 6.06 (1H,s), 6.11(2H,s), 7.59(1H,brs)

EXAMPLE 237

$^1$H NMR(CDCl$_3$): δ1.28(3H,t), 2.10(3H,brs), 3.11(2H,q), 3.28(4H,brs), 3.82(4H,brs), 3.85(3H,s), 4.00(3H,s), 6.77 (2H,d), 6.85 (1H,s), 7.60(1H,brs)

EXAMPLE 238

$^1$H NMR(CDCl$_3$): δ1.28(3H,t), 2.10(3H,brs), 2.43(3H,s), 3.06(6H,m), 3.86(7H,brs), 4.01(3H,s), 7.06(1H,s), 7.12(3H,s), 7.60 (1H,brs)

EXAMPLE 239

$^1$H NMR(CDCl$_3$): δ1.28(3H,t), 1.43(6H,t), 2.11(3H,brs), 3.12(2H,q), 3.37(4H,brs), 3.86(7H,brs), 4.01(3H,s), 4.41(4H,q), 7.60 (1H,brs), 7.79(2H,s), 8.18(1H,s)

EXAMPLE 240

$^1$H NMR(CDCl$_3$): δ1.28(3H,t), 2.10(3H,brs), 3.10(2H,q), 3.28(4H,brs), 3.82(4H,brs), 3.86(3H,s), 4.00(3H,s), 6.30 (1H,t), 6.39 (2H,d), 7.60(1H,brs)

EXAMPLE 241

$^1$H NMR(CDCl$_3$): δ2.07(3H,s), 3.27(4H,t), 3.79(6H,s), 3.86(4H,t), 4.10(3H,s), 6.06(1H,m), 6.12(2H,d), 7.32(1H,t), 7.36(1H,s), 7.48(1H,t), 7.61(1H,d), 7.80(1H,d)

EXAMPLE 242

$^1$H NMR(CDCl$_3$): δ2.07(3H,s), 2.30(6H,s), 3.25(4H,s), 3.86(4H,s), 4.10(3H,s), 6.58(1H,s), 6.60(2H,s), 7.32(1H,t), 7.36(1H,s), 7.49(1H,d), 7.80(1H,d)

EXAMPLE 243

$^1$H NMR(CDCl$_3$): δ2.09(3H,brs), 3.27(4H,s), 3.87(4H,s), 4.10(3H,s), 6.29(1H,t), 6.39(2H,d), 7.32(1H,t), 7.37(1H,s), 7.49(1H,t), 7.80(1H,d)

EXAMPLE 244

$^1$H NMR(CDCl$_3$): δ2.09(3H,brs), 3.15(4H,t), 3.89(4H,s), 4.11(3H,s), 6.89(1H,d), 6.96(2H,m), 7.04(1H,m), 7.32(1H,t), 7.38(1H,brs), 7.48(1H,t), 7.62(1H,d), 7.80(1H,d)

EXAMPLE 245

$^1$H NMR(CDCl$_3$): δ2.10(3H,brs), 3.29(4H,t), 3.88(4H,brs), 4.10(3H,s), 6.82(1H,dd), 6.88(1H,d), 6.92(1H,s), 7.20 (1H,t), 7.33(1H,t), 7.40(1H,brs), 7.49(1H,t), 7.62(1H,d), 7.80(1H,d)

EXAMPLE 246

$^1$H NMR(CDCl$_3$): δ2.14(3H,brs), 2.17(3H,s), 2.22(3H,s), 3.25(4H,t), 3.78(7H,s), 6.60(1H,brs), 6.66(1H,s), 6.89(1H,t), 6.95(2H,t), 7.29(2H,t)

EXAMPLE 247

$^1$H NMR(CDCl$_3$): δ2.14(3H,brs), 2.17(3H,s), 2.22(3H,s), 2.28(3H,s), 3.19(4H,t), 3.77(7H,s), 6.60(1H,brs), 6.66(1H,s), 6.86(2H,d), 7.08(2H,d)

EXAMPLE 248

$^1$H NMR(CDCl$_3$): δ1.25(3H,t), 2.14(3H,brs), 2.18(3H,s), 2.23(3H,s), 2.72(2H,q), 2.96(4H,brs), 3.75(4H,brs), 3.79 (3H,s), 6.60 (1H,brs), 6.67(1H,s), 7.08(2H,t), 7.18(1H,t), 7.24(1H,m)

EXAMPLE 249

$^1$H NMR(CDCl$_3$): δ2.12(3H,s), 2.16(3H,s), 2.22(3H,s), 2.29(6H,s), 3.21(4H,t), 3.74(4H,t), 3.77(3H,s), 6.55(1H,s), 6.59(3H,s), 6.65(1H,s)

EXAMPLE 250

$^1$H NMR(CDCl$_3$): δ2.12(3H,s), 2.16(3H,s), 2.22(3H,s), 3.23(4H,t), 3.74(4H,t), 3.77(3H,s), 3.78(6H,s), 6.04(1H,s), 6.12(2H,d), 6.59(1H,s), 6.65(1H,s)

EXAMPLE 251

$^1$H NMR(CDCl$_3$): δ2.11(3H,s), 2.16(3H,s), 2.22(3H,s), 3.25(4H,t), 3.74(4H,t), 3.77(3H,s), 6.28(1H,t), 6.39(2H,d), 6.59(1H,s), 6.66(1H,s)

EXAMPLE 252

$^1$H NMR(CDCl$_3$): δ2.14(3H,brs), 2.17(3H,s), 2.22(3H,s), 3.25(4H,t), 3.76(4H,brs), 3.78(3H,s), 6.61(1H,brs), 6.66 (1H,s), 6.83 (2H,m), 6.90(1H,s), 7.18(1H,t)

EXAMPLE 253

$^1$H NMR(CDCl$_3$): δ2.14(3H,brs), 2.17(3H,s), 2.23(3H,s), 3.25(4H,t), 3.78(7H,s), 6.61(1H,brs), 6.66(1H,s), 6.85(1H, d), 6.98 (1H,d), 7.06(1H,s), 7.12(1H,t)

EXAMPLE 254

$^1$H NMR(CDCl$_3$) δ2.14(3H,brs), 2.17(3H,s), 2.22(3H,s), 2.42(3H,s), 3.06(4H,t), 3.78(7H,s), 6.60(1H,brs), 6.66(1H, s), 7.06 (1H,m), 7.12(3H,s)

Antitumor activities of the compounds of the present invention were tested in vitro against 5 kinds of human tumor cell lines and a leukemia tumor cell line. The method and result of the in vitro tests is as follows.

Experimental 1

In vitro antitumor effect against human tumor cell lines.

A. Tumor Cell Line:
- A549 (human non-small lung cell)
- SKOV-3 (human ovarian)
- HCT-15 (human colon)
- XF 498 (human CNS)
- SKMEL-2 (human melanoma)

B. SRB Assay Method a. Human solid tumor cell lines, A549(non-small lung cell), SKMEL-2(melanoma), HCT-15(colon), SKOV-3 (ovarian), XF-498(CNS) were cultured at 37° C. in 5% CO$_2$ incubators using RPMI 1640 media containing 10% FBS, while they were transfer-cultured successively once or twice per week. Cell cultures were dissolved in a solution of 0.25% trypsin and 3 mM CDTA PBS(−) and then cells were separated from media which the cells were sticked on.

b. 5×10$^3$~2×10$^4$ cells were added into each well of 96-well plate and cultured in 5% CO$_2$ incubator, at 37° C., for 24 hours.

c. Each sample drug was dissolved in a little DMSO and diluted with the used medium to a prescribed concentration for experiments, wherein the final concentration of DMSO was controlled below 0.5%.

d. Medium of each well cultured for 24 hours as above b. was removed by aspiration. Each 200 μl of drug samples prepared in c. was added into each well and the wells were cultured for 48 hours. Tz(time zero) plates were collected at the point of time drugs were added.

e. According to the SRB assay method, cell fixing with TCA, staining with 0.4% SRB solution, washing with 1% acetic acid and elution of dye with 10 mM Tris solution were carried out on Tz plates and culture-ended plates, whereby OD values were measured at 520 nm.

C. Calculation of Result a. Time zero(Tz) value was determined with measuring the SRB protein amounts of the Tz plates collected at the point of time drugs were added.

b. Control value(C) was determined with the OD values of wells untreated with a drug.

c. Drug-treated test value(T) was determined with the OD values of drug-treated wells.

d. Effects of drugs were estimated with growth stimulation, net growth inhibition, net killing etc., being calculated from Tz, C and T.

e. If T≧Tz, cellular response function was calculated by 100×(T−Tz)/(C−Tz), and if T<Tz, by 100×(T−Tz)/Tz. The results are shown in the next table 1.

Reference

1) P. Skehan, R. Strong, D Scudiero, A. Monks, J. B. Mcmahan, D. T. Vistica, J. Warren, H. Bokesh, S. Kenny and M. R. Boyd:Proc. Am. Assoc. Cancer Res., 30, 612(1989)

2) L. V. Rubinstein, R. H. Shoemaker, K. D. Paull, R. M. simon, S. Tosini, P. Skehan, D. Scudiero, A. Monks and M. R. boyd.; J. Natl. Cancer Inst., 82, 1113(1990)

3) P. Skehan, R. Strong, D. Scudiero, A. monks, J. B. Mcmahan, D. T. Vistica, J. Warren, H. Bokesh, S. Kenny and M. R. Boyd.; J, Natl. Cancer Ins., 82, 1107(1990)

D. Results

It was found that all the tested compounds of the present invention have superior antitumor activities to the control, cisplatin.

TABLE 1

| Example No. | ED$_{50}$ = μg/ml | | | | |
|---|---|---|---|---|---|
| | A 549 | SK-OV-3 | SK-MEL-2 | XF-498 | HCT 15 |
| 2 | 0.032 | 0.088 | 0.029 | 0.084 | 0.019 |
| 3 | 0.0016 | 0.0064 | 0.0015 | 0.0022 | 0.0020 |
| 4 | 0.047 | 0.251 | 0.042 | 0.089 | 0.038 |
| 7 | 0.0024 | 0.0072 | 0.0023 | 0.0027 | 0.0028 |
| 12 | 0.008 | 0.069 | 0.008 | 0.017 | 0.001 |
| 14 | 0.204 | 0.677 | 0.283 | 0.340 | 0.067 |
| 15 | 0.079 | 0.184 | 0.038 | 0.096 | 0.071 |
| 19 | 0.0064 | 0.143 | 0.043 | 0.093 | 0.080 |
| 20 | 0.323 | 0.904 | 0.211 | 0.970 | 0.295 |
| 21 | 0.038 | 0.093 | 0.024 | 0.097 | 0.008 |
| 28 | 0.0001 | 0.0006 | <0.0001 | 0.0001 | 0.0001 |
| 30 | 0.0006 | 0.0007 | <0.0001 | 0.0005 | 0.0007 |
| 34 | 0.0023 | 0.0038 | 0.0003 | 0.0021 | 0.0021 |
| 35 | 0.0001 | 0.0007 | <0.0001 | 0.0001 | 0.0001 |
| 37 | 0.01 | 0.02 | 0.02 | 0.003 | 0.009 |
| 38 | 0.00003 | 0.00009 | 0.00004 | 0.00011 | 0.00013 |
| 39 | 0.10 | 0.33 | 0.07 | 0.14 | 0.06 |
| 40 | 0.41 | 1.01 | 0.37 | 0.81 | 0.39 |
| 42 | 0.0018 | 0.0043 | 0.0012 | 0.0057 | 0.0026 |
| 45 | 0.0001 | 0.0002 | <0.0001 | 0.0002 | 0.0001 |
| 46 | 0.002 | 0.007 | 0.003 | 0.001 | 0.002 |
| 48 | 0.001 | 0.007 | 0.0003 | 0.004 | 0.002 |
| 51 | 0.37 | 0.68 | 0.28 | 0.63 | 0.18 |
| 53 | 0.17 | 0.21 | 0.93 | 0.27 | 0.05 |
| 55 | 0.34 | 0.49 | 0.22 | 0.41 | 0.33 |
| 64 | 0.019 | 0.057 | 0.011 | 0.014 | 0.032 |
| 66 | 0.005 | 0.008 | 0.002 | 0.008 | 0.003 |
| 68 | 0.38 | 0.86 | 0.34 | 0.47 | 0.31 |
| 72 | 0.0001 | 0.0007 | <0.0001 | 0.0001 | 0.0001 |
| 74 | 0.0020 | 0.038 | 0.003 | 0.024 | 0.028 |
| 86 | 0.04 | 0.08 | 0.03 | 0.04 | 0.06 |
| 87 | 0.01 | 0.03 | 0.66 | 0.08 | 0.008 |
| 89 | 0.04 | 0.20 | 0.03 | 0.04 | 0.05 |
| 90 | 0.38 | 0.35 | 0.90 | 0.68 | 0.20 |
| 99 | 0.012 | 0.008 | 0.006 | 0.010 | 0.003 |
| 101 | 0.0003 | 0.0003 | 0.0003 | 0.0002 | 0.0001 |
| 107 | 0.032 | 0.013 | 0.005 | 0.008 | 0.009 |
| 118 | 0.057 | 0.032 | 0.019 | 0.017 | 0.0002 |
| 120 | 0.64 | 0.73 | 0.28 | 0.82 | 0.30 |
| 125 | 0.0009 | 0.0008 | 0.0001 | 0.0001 | 0.0001 |
| 127 | 0.013 | 0.011 | 0.005 | 0.006 | 0.002 |
| 132 | 0.011 | 0.007 | 0.001 | 0.002 | 0.001 |
| 133 | 0.0001 | 0.0001 | 0.0001 | 0.0001 | 0.0001 |
| 138 | 0.074 | 0.030 | 0.016 | 0.018 | 0.006 |
| 139 | 0.0007 | 0.0007 | 0.0002 | 0.0003 | 0.0004 |
| 159 | 0.029 | 0.010 | 0.002 | 0.006 | 0.0006 |
| 172 | 0.07 | 0.08 | 0.02 | 0.03 | 0.02 |
| 173 | 0.40 | 0.86 | 0.15 | 0.21 | 0.18 |
| 176 | 0.0012 | 0.0009 | 0.0003 | 0.0001 | 0.0001 |
| 177 | 0.0006 | 0.0008 | 0.0003 | 0.0004 | 0.0001 |
| 180 | 0.28 | 0.16 | 0.31 | 0.24 | 0.16 |
| 181 | 0.13 | 0.06 | 0.11 | 0.04 | 0.02 |
| 182 | 0.292 | 0.081 | 0.033 | 0.103 | 0.006 |
| Cisplatin | 0.91 | 1.32 | 0.87 | 0.77 | 3.17 |

Experimental 2

In vitro antitumor effects against animal leukemia cells.

A. Material:
Tumor cell line: P388 (mouse lymphoid neoplasma cell)

B. Method: Dye Exclusion Assay.

1) Concentrations of P388 cells being cultured in RPMI 1640 media containing 10% FBS were regulated to 1×10$^6$ cells/ml.

2) Sample drugs of respective concentrations diluted in the ratio of log doses were added into each cell culture and cultured at 37° C., for 48 hours, in 50% CO$_2$ incubator, and then viable cell numbers were measured by dye exclusion test using trypan blue.

3) Concentrations of sample compounds showing 50% cell growth inhibition compared with the control(IC$_{50}$) were determined and listed in the table 2 below.

Reference
1) P. Skehan, R. Strong, D. Scudiero, A. Monks, J. B. Mcmahan, D. T. Vistica, J. Warren, H. Bokesh, S. Kenney and M. R. Boyd.: Proc. Am. Assoc. Cancer Res., 30, 612(1989).
2) L. V. Rubinstein, R. H. Shoemaker, K. D. Paull, R. M. Simon, S. Tosini, P. Skehan, D. Scudiero, A. Monks, J. Natl. Cancer Inst., 82, 1113(1990)
3) P. Skehan, R. Strong, D. Scudiero, J. B. Mcmahan, D. T. Vistica, J. Warren, H. Bokesch, S. Kenney and M. R. Boyd.: J. Natl. Cancer Inst., 82, 1107(1990)

C. Results

As the results of measurement of antitumor activities of compounds of the present invention against P388 mouse leukemia cells, it was found that all the compounds tested have equal to or higher antitumor activities than those of the control drug, mitomycin C.

| Example No. | P388 |
|---|---|
| 2 | 0.3 |
| 3 | 0.01 |
| 7 | 0.02 |
| 11 | 0.02 |
| 12 | 0.1 |
| 15 | 0.70 |
| 19 | 0.2 |
| 20 | 1.2 |
| 21 | 0.8 |
| 28 | 0.04 |
| 30 | 0.07 |
| 34 | 0.14 |
| 35 | 0.01 |
| 37 | 0.3 |
| 38 | 0.01 |
| 42 | 0.03 |
| 45 | 0.15 |
| 46 | 0.2 |
| 48 | 0.39 |
| 64 | 0.34 |
| 66 | 0.2 |
| 72 | 0.10 |
| 74 | 0.68 |
| 99 | 0.04 |
| 101 | 0.002 |
| 107 | 0.04 |
| 118 | 0.3 |
| 138 | 0.1 |
| 139 | 0.03 |
| 173 | 0.4 |
| 180 | 0.05 |
| 181 | 0.03 |
| 182 | 0.2 |
| Mitomycin C | 1.1 |

Experimental 3
Acute toxicity test (LD$_{50}$):
A. Method: Litchfield-Wilcoxon method.

6 weeks old ICR mice (male 30±2.0 g) were fed freely with solid feed and water at room temperature, 23±1° C. at humidity 60±5%. Sample drugs were injected into abdominal cavities of mice, while each group comprises 6 mice. Observed during 14 days, external appearances and life or death were recorded, and then, visible pathogenies were observed from dead animals by dissection. LD$_{50}$ value was calculated by Litchfiled-wilcoxon method.

B. Result
The results are shown at the next table 3.

TABLE 3

| | LD$_{50}$(mg/kg) | | |
|---|---|---|---|
| Example No. | p.o. | i.v. | i.p. |
| 7 | | 75 | |
| 38 | 410 | 97 | |
| 99 | | >200 | |
| 104 | | 212 | |
| Cisplatin | | | 9.7 |

As described above, it was found that the compounds of the present invention are more safer than cisplatin, whereby the present compounds may solve problems of known drugs by the prior art such as restriction of dosage, toxicity, etc.

What is claimed:

1. A compound of formula (I):

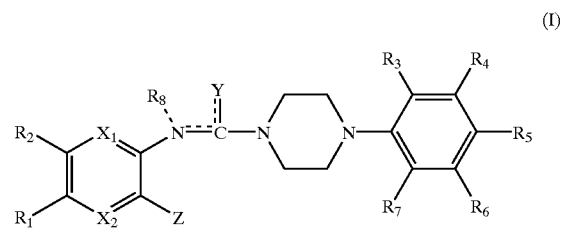

(I)

wherein R$_1$ and R$_2$ are independently hydrogen, C$_1$–C$_4$ alkyl, C$_1$–C$_4$ alkylcarboxyl, C$_1$–C$_4$ alkylcarbonyl, C$_1$–C$_4$ alkoxy, C$_1$–C$_4$ hydroxyalkyl, C$_1$–C$_4$ aminoalkyl or C$_1$–C$_4$ hydroxyiminoalkyl, or R$_1$ and R$_2$ are fused to form C$_3$–C$_4$ unsaturated ring;

R$_3$, R$_4$, R$_5$, R$_6$ and R$_7$ are independently hydrogen, halogen, hydroxy, nitro, amino, C$_1$–C$_4$ alkyl, C$_1$–C$_4$ alkylcarboxyl, C$_1$–C$_4$ alkylcarbonyl, C$_1$–C$_4$ alkoxy or C$_1$–C$_4$ thioalkoxy;

R$_8$ is C$_1$–C$_4$ alkyl;

Y is oxygen, sulphur, amino, hydroxy amino, C$_1$–C$_4$ alkylamino, C$_1$–C$_4$ alkoxyamino, or C$_1$–C$_4$ thioalkyl;

Z is C$_1$–C$_4$ alkoxy, C$_1$–C$_4$ alkyl, C$_1$–C$_4$ alkylamino or C$_1$–C$_4$ thioalkoxy;

X$_1$ is CH or nitrogen and X$_2$ is nitrogen provided that if X$_1$ is CH, Y is amino, hydroxy amino, C$_1$–C$_4$ alkylamino, C$_1$–C$_4$ alkoxyamino or C$_1$–C$_4$ thioalkyl; and —N=C— and —C=Y— may form a single bond or a double bond provided that if —N=C— forms a single bond, —C=Y— forms a double bond, and if —C=Y— forms a single bond, —N=C— forms a double bond and R$_8$ is nonexistent; or pharmaceutically acceptable acid addition salts thereof.

2. A process for the preparation of a compound of formula (Ia) or a pharmaceutically acceptable acid addition salt thereof comprising reacting a compound of formula (2) with a —C(=Y)— group-providing agent in an organic solvent to obtain a compound of formula (3) and successively reacting the compound of formula (3) with a compound of formula (4) to give the compound of formula (5), and reacting the compound of formula (5) with an alkylating agent in the presence of a base to give the compound of formula (Ia):

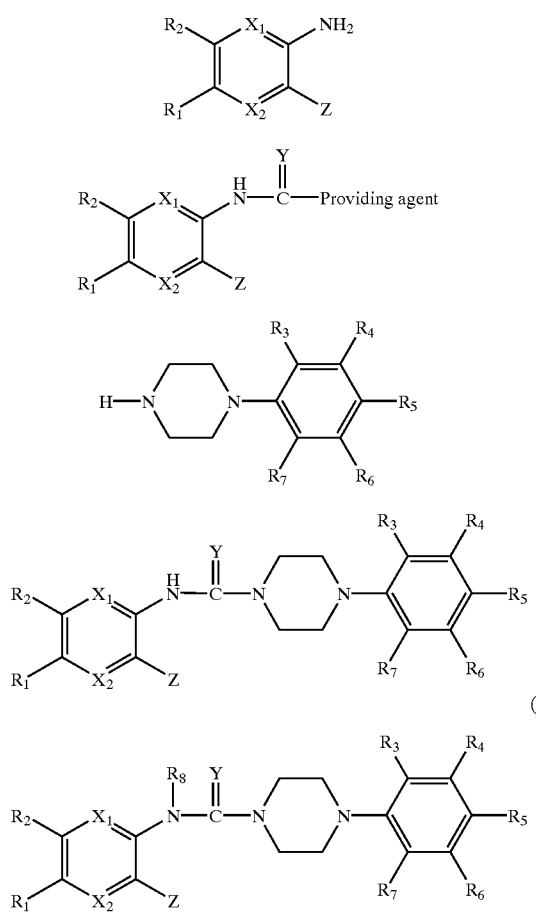

wherein $R_1$, $R_2$, $R_3$, $R_4$, $R_5$, $R_6$, $R_7$, $R_8$, $X_2$, and Z are as defined in claim 1, $X_1$ is nitrogen and Y is oxygen or sulphur.

3. A process for the preparation of compound of formula (Ib) or a pharmaceutically acceptable acid addition salt thereof comprising reacting a compound of formula (II) with an alkylating agent in the presence of a base to give a compound of formula (I') and reacting the compound of formula (I') with a substituted or unsubstituted amine in the presence of a base to give the compound of formula (Ib):

wherein $R_1$, $R_2$ $R_3$, $R_4$, $R_5$, $R_6$, $R_7$, $X_2$, and Z are as defined in claim 1, R' is $C_1$–$C_4$ alkyl, $X_1$ is CH, and Y is amino, hydroxy amino, $C_1$–$C_4$ alkylamino, $C_1$–$C_4$ alkoxyamino or $C_1$–$C_4$ thioalkyl.

* * * * *